(12) United States Patent
Carrier et al.

(10) Patent No.: US 10,501,756 B2
(45) Date of Patent: Dec. 10, 2019

(54) GENE-THERAPY VECTORS FOR TREATING CARDIOMYOPATHY

(71) Applicants: UNIVERSITÄTSKLINIKUM HAMBURG-EPPENDORF, Hamburg (DE); RUPRECHT-KARLS-UNIVERSITÄT HEIDELBERG, Heidelberg (DE); Sorbonne Université, Paris (FR); ASSOCIATION INSTITUT DE MYOLOGIE, Paris (FR)

(72) Inventors: Lucie Carrier, Hamburg (DE); Thomas Eschenhagen, Hamburg (DE); Thomas Voit, London (GB); Giulia Mearini, Hamburg (DE); Oliver Mueller, Dossenheim (DE); Doreen Stimpel, Hamburg (DE); Julia Mourot-Filiatre, Brasilia (BR)

(73) Assignees: UNIVERSITÄTSKLINIKUM HAMBURG-EPPENDORF, Hamburg (DE); RUPRECHT-KARLS-UNIVERSITÄT HEIDELBERG, Heidelberg (DE); SORBONNE UNIVERSITÉ, Paris (FR); ASSOCIATION INSTITUTE DE MYOLOGIE, Paris (FR)

( * ) Notice: Subject to any disclaimer, the term of this patent is extended or adjusted under 35 U.S.C. 154(b) by 0 days.

(21) Appl. No.: 14/785,188

(22) PCT Filed: Apr. 17, 2014

(86) PCT No.: PCT/EP2014/057984
§ 371 (c)(1),
(2) Date: Oct. 16, 2015

(87) PCT Pub. No.: WO2014/170470
PCT Pub. Date: Oct. 23, 2014

(65) Prior Publication Data
US 2016/0108430 A1   Apr. 21, 2016

(30) Foreign Application Priority Data

Apr. 17, 2013 (EP) .................................. 13164212
Dec. 18, 2013 (EP) .................................. 13198201

(51) Int. Cl.
*A61K 48/00* (2006.01)
*C12N 15/86* (2006.01)
*A61K 35/34* (2015.01)
*C07K 14/47* (2006.01)
*C12N 5/074* (2010.01)
*C12N 5/077* (2010.01)
*C12N 7/00* (2006.01)

(52) U.S. Cl.
CPC .............. *C12N 15/86* (2013.01); *A61K 35/34* (2013.01); *A61K 48/0058* (2013.01); *C07K 14/4716* (2013.01); *C12N 5/0657* (2013.01); *C12N 5/0696* (2013.01); *C12N 7/00* (2013.01); *C12N 2506/45* (2013.01); *C12N 2750/14143* (2013.01); *C12N 2799/025* (2013.01); *C12N 2830/007* (2013.01); *C12N 2830/008* (2013.01)

(58) Field of Classification Search
CPC .................................................. A61K 48/0058
See application file for complete search history.

(56) References Cited

U.S. PATENT DOCUMENTS

| 5,591,624 A | 1/1997 | Barber et al. |
| 8,933,048 B2 * | 1/2015 | Stelzer ............... A61K 31/7088 424/93.1 |
| 2002/0127548 A1 | 9/2002 | Siedman et al. |
| 2004/0086876 A1 | 5/2004 | Seidman et al. |
| 2005/0276804 A1 | 12/2005 | Smith et al. |
| 2007/0292438 A1 | 12/2007 | Anderson et al. |
| 2013/0072549 A1 | 3/2013 | Stelzer et al. |

FOREIGN PATENT DOCUMENTS

| DE | 102011018586 A1 * | 10/2012 | ............. C12N 15/85 |
| DE | 102011018586 A1 | 10/2012 | |
| EP | 13164212.6 | 4/2013 | |
| EP | 13198201.9 | 12/2013 | |
| WO | 96/37626 A1 | 11/1996 | |
| WO | WO-2008093323 A2 * | 8/2008 | ............. C07K 14/47 |
| WO | 2012/162705 A2 | 11/2012 | |
| WO | 2012/162705 A3 | 11/2012 | |
| WO | 2013/009825 A1 | 1/2013 | |
| WO | 2014170470 A1 | 10/2014 | |

OTHER PUBLICATIONS

Mearini et al. (2013, Molecular Therapy-Nucleic Acids, vol. 2, e102, pp. 1-9).*

(Continued)

*Primary Examiner* — Thaian N Ton
*Assistant Examiner* — David A. Montanari
(74) *Attorney, Agent, or Firm* — Hovey Williams LLP

(57) ABSTRACT

The present invention relates to a gene therapy vector which is useful in the treatment or prevention of hypertrophic cardiomyopathy in a subject in need thereof. The gene therapy vector of the invention comprises a nucleic acid sequence encoding a cardiac sarcomeric protein and a cardiomyocyte-specific promoter which is operably linked to said nucleic acid sequence. The invention furthermore relates to a cell which comprises the gene therapy vector. Pharmaceutical compositions which comprise the gene therapy vector and/or a cell comprising said vector are also provided. In another aspect, the invention relates to a method for treating or preventing hypertrophic cardiomyopathy in a subject by introducing the gene therapy vector of the invention into a subject in need of treatment.

5 Claims, 8 Drawing Sheets
Specification includes a Sequence Listing.

(56) References Cited

OTHER PUBLICATIONS

Seidman et al., 2011, Circ. Res., vol. 108(6), pp. 1-15.*
Marian AJ (2010, Eur. J. Clin. Invest., vol. 40(4), pp. 360-369.*
Kotterman et al. (2014, Nature Genetics, vol. 15, pp. 445-451).*
Chamberlain et al. (2017, Current Opinion in Cardiology, vol. 32(3), pp. 275-282).*
Hannah-Shmouni et al. (2015, Canadian J. Cardiology, vol. 31, pp. 1338-1350).*
Chute JP, Current Opin. Hematology, vol. 13, pp. 399-406.*
Li et al. (2010, J. Cerebral Blood Flow and Metabolism, vol. 30, pp. 653-662).*
Parr et al. (2007, Bone Marrow Transplant, vol. 40, pp. 609-619).*
Hansen et al.: "Development of a Drug Screening Platform Based on Engineered Heart Tissue" Circ Res vol. 107, 2010, pp. 35-44 (10 pages).
Stoehr et al.: "Contractile abnormalities and altered drug response in engineered heart tissue from Mybpc3-targeted knock-in mice" J Mol Cell Cardiol vol. 63, 2013, pp. 189-198 (10 pages).
Vandenburgh et al.: "Drug-screening platform based on the contractility of tissue-engineered muscle" Muscle Nerve vol. 37, 2008, pp. 438-447 (10 pages).
Sands: "Percutaneous intravenous injection in neonatal mice" Lab Anim Sci vol. 49, 1999, pp. 328-330 (3 pages).
Yang L et al.: "Human caradiovascular progenitor cells develop from a KDR+ embryonic-stem-cell-derived population" Nature vol. 22, 2008, pp. 524-528 (6 pages).
Flavigny J et al.: "COOH-terminal Truncated Cardiac Myosin-binding Protein C Mutants Resulting from Familial Hypertrophic Cardiomyopathy Mutations Exhibit Altered Expression and/or Incorporation in Fetal Rat Cardiomyocytes" J Mol Biol vol. 294, 1999, pp. 443-456 (14 pages).
Sarikas et al.: "Impairment of the ubiquitin—proteasome system by truncated cardiac myosin binding protein C mutants" Cardiovasc Res vol. 66, 2005, pp. 33-44 (12 pages).
He T et al.: "A simplified system for generating recombinant adenoviruses" Proc Natl Acad Sci U S A vol. 95, 1998, pp. 2509-2514 6 (6 pages).
International Search Report and Written Opinion dated Jul. 11, 2014 in Corresponding PCT/EP2014/057984 (13 pages).
Extended Search Report dated Mar. 25, 2014 in Corresponding EP 13 19 8201 (8 pages).
International Preliminary Report on Patentability dated Oct. 20, 2015 in Corresponding PCT/EP2014/057984 (7 pages).
Van Dijk et al.: "Contractile Dysfunction Irrespective of the Mutant Protein in Human Hypertrophic Cardiomyopathy With Normal Systolic Function" Circ Heart Fail vol. 5, 2012, pp. 36-46 (17 pages).
Dong, et al., "Characterization of Genome Integrity for Oversized Recombinant AAV Vector," Molecular Therapy, Jan. 2010, vol. 18, issue 1, pp. 87-92.
Search Report in related European Patent Application No. 14719704. 0-1410, dated Oct. 25, 2016, 5 pages.
Khajetoorians et al.: "Replacement of Mybpc3 Mutation by 5'-transsplicing in a Knockin Mouse Model: A Step Towards Causal Therapy of Hypertrophic Cardiomyopathy", Circulation Research vol. 111, No. 12, Dec. 1, 2012, e2 (9 pages).
Prasad et al: "Robust cardiomyocyte-specific gene expression following systemic injection of AAV: in vivo gene delivery follows a Poisson distribution", Gene Therapy, vol. 18, No. 1, Aug. 12, 2010 (Aug. 12, 2010), pp. 43-52 (10 pages).
Mearini, Giulia et al: "Repair of Mybpc3 mRNA by 5'-trans-splicing in a Mouse Model of Hypertrophic Cardiomyopathy", Molecular Therapy-Nucleic Acids, vol. 2, No. 7, Jul. 2, 2013 (Jul. 2, 2013), p. e102 (10 pages).
Ralph Knoell: "Myosin binding protein C: implications for signal-transduction", Journal of Muscle Research and Cell Motility, Kluwer Academic Publishers, DO, vol. 33, No. 1, Dec. 16, 2011 (Dec. 16, 2011), pp. 31-42 (12 pages).

Elliott et al.: "Classification of the cardiomyopathies: a position statement from the european society of cardiology working group on myocardial and pericardial diseases" Eur Heart J vol. 29, 2008, pp. 270-276 (7 pages).
Gersch et al.: "2011 ACCF/AHA guidelines for the diagnosis and treatment of hypertrophic cardiomyopathy" J Thorac Cardiovasc Surg vol. 142, 2011, pp. E153-203 (51 pages).
Maron et al.: "Prevalence of Hypertrophic Cardiomyopathy in a General Population of Young Adults" Circulation vol. 92, 1995, pp. 785-789 (17 pages).
Carrier et al.: "The ubiquitin-proteasome system and nonsensemediated mRNA decay in hypertrophic cardiomyopathy" Cardiovasc Res vol. 85, 2010, pp. 330-338 (9 pages).
Schlossarek et al.: "Cardiac myosin-binding protein C in hypertrophic cardiomyopathy: Mechanisms and therapeutic opportunities" J Mol Cell Cardiol vol. 50, 2011, pp. 613-620 (8 pages).
Richard et al.: "Hypertrophic Cardiomyopathy Distribution of Disease Genes, Spectrum of Mutations, and Implications for a Molecular Diagnosis Strategy" Circulation vol. 107, 2003, pp. 2227-2232 (10 pages).
Friedrich et al.: "Evidence for FHL1 as a novel disease gene for isolated hypertrophic cardiomyopathy" Hum Mol Genet vol. 21, 2012, pp. 3237-3254 (18 pages).
Bonne et al.: "Cardiac myosin binding protein-C gene splice acceptor site mutation is associated with familial hypertrophic cardiomyopathy" Nature Genet vol. 11, 1995, pp. 438-440 (3 pages).
Watkins et al.: "Inherited cardiomyopathies" N. Engl J Med. vol. 364, 2011, pp. 1643-1656 (14 pages).
Fougerousse et al.: "Cardiac Myosin Binding Protein C Gene Is Specifically Expressed in Heart During Murine and Human Development" Circ Res vol. 82, 1998, pp. 130-133 (5 pages).
Pohlmann et al.: "Cardiac Myosin-Binding Protein C Is Required for Complete Relaxation in Intact Myocytes" Circ Res vol. 101, 2007, pp. 928-3 (19 pages).
Carrier et al.: "Organization and Sequence of Human Cardiac Myosin Binding Protein C Gene (MYBPC3) and Identification of Mutations Predicted to Produce Truncated Proteins in Familial Hypertrophic Cardiomyopathy" Circ Res vol. 80, 1997, pp. 427-434 (8 pages).
Marston et al.: "Evidence From Human Myectomy Samples That MYBPC3 Mutations Cause Hypertrophic Cardiomyopathy Through Haploinsufficiency" Circ Res vol. 105, 2009, pp. 219-222 (15 pages).
Van Dijk et al.: "Cardiac Myosin-Binding Protein C Mutations and Hypertrophic Cardiomyopathy" Circulation vol. 119, 2009, pp. 1473-1483 (12 pages).
Meurs et al.: "A cardiac myosin binding protein C mutation in the Maine Coon cat with familial hypertrophic cardiomyopathy" Hum Mol Genet vol. 14, 2005, pp. 3587-3593 (7 pages).
Vignier et al.: "Nonsense-Mediated mRNA Decay and Ubiquitin—Proteasome System Regulate Cardiac Myosin-Binding Protein C Mutant Levels in Cardiomyopathic Mice" Circ Res vol. 105, 2009, pp. 239-248 (10 pages).
Jessup et al.: "Calcium Upregulation by Percutaneous Administration of Gene Therapy in Cardiac Disease (CUPID)" Circulation vol. 124, 2011, pp. 304-313 (40 pages).
Merkulov et al.: "In Vivo Cardiac Myosin Binding Protein C Gene Transfer Rescues Myofilament Contractile Dysfunction in Cardiac Myosin Binding Protein C Null Mice" Circ Heart Fail vol. 5, 2012, pp. 635-644 (22 pages).
Schlossarek et al.: "Defective proteolytic systems in Mybpc3-targeted mice with cardiac hypertrophy" Basic Res Cardiol vol. 107, 2012, pp. 1-13 (13 pages).
Schlossarek et al.: "Adrenergic stress reveals septal hypertrophy and proteasome impairment in heterozygous Mybpc3-targeted knock-in mice" J Muscle Res Cell Motil vol. 33, 2012, pp. 5-15 (11 pages).
Sadayappan et al.: "Cardiac Myosin-Binding Protein-C Phosphorylation and Cardiac Function" Circ Res vol. 97, 2005, pp. 1156-1163 (26 pages).
Sadayappan et al.: "Cardiac myosin binding protein c phosphorylation is cardioprotective" Proc Natl Acad Sci U S A vol. 103, 2006, pp. 16918-16923 (6 pages).

(56) References Cited

OTHER PUBLICATIONS

Gorman et al.: "The Rous sarcoma virus long terminal repeat is a strong promoter when introduced into a variety of eukaryotic cells by DNA-mediated transfection" Proc. Natl. Acad. Sci. vol. 79, 1982, p. 6777 (5 pages).
Geisler et al.: "microRNA122-regulated transgene expression increases specificity of cardiac gene transfer upon intravenous delivery of AAV9 vectors" Gene Therapy vol. 18, 2011, pp. 199-209 (11 pages).
Dominguez et al.: "Intravenous scAAV9 delivery of a codon-optimized SMN1 sequence rescues SMA mice" Hum Mol Genet vol. 20, 2011, pp. 681-693 (13 pages).
Wu et al.: "Adeno-associated Virus Serotypes: Vector Toolkit for Human Gene Therapy" Mol Therapy vol. 14, 2006, pp. 316-327 (12 pages).
Bowles et al.: "Phase 1 Gene Therapy for Duchenne Muscular Dystrophy Using a Translational Optimized AAV Vector" Mol Therapy vol. 20, 2012, pp. 443-455 (13 pages).
Wu et al.: "Effect of Genome Size on AAV Vector Packaging" Mol Therapy vol. 18, 2010, pp. 80-86 (7 pages).
Katz et al.: "Gene delivery technologies for cardiac applications" Gene Therapy vol. 19, 2012, pp. 659-669 (24 pages).
Jaski et al.: "Calcium Upregulation by Percutaneous Administration of Gene Therapy in Cardiac Disease (CUPID Trial), a First-in-Human Phase ½ Clinical Trial" J Card Fail vol. 15, 2009, pp. 171-181 (11 pages).
Gao et al.: "Transendocardial Delivery of AAV6 Results in Highly Efficient and Global Cardiac Gene Transfer in Rhesus Macaques" Human Gene Therapy vol. 22, 2011, pp. 979-984 (7 pages).
Okita et al.: "Generation of germline-competent induced pluripotent stem cells" Nature vol. 448, 2007, pp. 313-317 (6 pages).
Yu et al.: "Induced Pluripotent Stem Cell Lines Derived from Human Somatic Cells" Science vol. 318, 2007, pp. 1917-1920 (4 pages).
Maekawa et al.: "Direct reprogramming of somatic cells is promoted by maternal transcription factor Glis1" Nature vol. 474, 2011, pp. 225-229 (6 pages).
Aasen et al.: "Efficient and rapid generation of induced pluripotent stem cells from human keratinocytes" Nat Biotech vol. 11, 2008, pp. 1276-1284 (9 pages).
Aasen et al.: "Isolation and cultivation of human keratinocytes from skin or plucked hair for the generation of induced pluripotent stem cells" Nat Protocol vol. 5, 2010, pp. 371-382 (12 pages).
Staerk et al.: "Reprogramming of Human Peripheral Blood Cells to Induced Pluripotent Stem Cells" Cell Stem Cell vol. 7, 2010, pp. 20-24 (5 pages).
Seki et al.: "Generation of induced pluripotent stem cells from a small amount of human peropheral blood using a combination of activated T cells and Sendai virus" Nat Protocol vol. 7, 2012, pp. 718-728 (11 pages).
Muller et al.: "Improved cardiac gene transfer by transcriptional and transductional targeting of adeno-associated viral vectors" Cardiovasc Res vol. 70, 2006, pp. 70-78 (9 pages).
Kaya et al.: "Comparison of IL-10 and MCP-1-7ND gene transfer with AAV9 vectors for protection from murine autoimmune myocarditis" Cardiovasc Res vol. 91, 2011, pp. 116-123 (8 pages).
Grimm et al.: "Helper Virus-Free, Optically Controllable, and Two-Plasmid-Based Production of Adeno-associated Virus Vectors of Serotypes 1 to 6" Mol Therapy vol. 7, 2003, pp. 839-850 (12 pages).
Grieger et al.: "Production and characterization of adeno-associated viral vectors" Nat Protoc vol. 1, 2006, pp. 1412-1428 (17 pages).
Hauswirth et al.: "Production and purification of recombinant adeno-associated virus" Methods Enzymol vol. 316, 2000, pp. 743-761 (19 pages).
Veldwijk et al.: "Development and Optimization of a Real-Time Quantitative PCR-Based Method for the Titration of AAV-2 Vector Stocks" Mol Therapy vol. 6, 2002, pp. 272-278 (7 pages).
Laugwitz et al.: "Postnatal isl1+ cardioblasts enter fully differentiated cardiomyocyte lineages" Nature vol. 433, 2005, pp. 647-653 (8 pages).
Moretti et al.: "Multipotent Embryonic IsI1+ Progenitor Cells Lead to Cardiac, Smooth Muscle, and Endothelial Cell Diversification" Cell vol. 127, 2006, pp. 1151-1165 (15 pages).
Office Action in corresponding Canadian Patent Application Serial No. 2,944,186, dated Aug. 14, 2018.

* cited by examiner

A

B

C

*$P<0.05$ and **$P<0.01$ vs GFP
$P<0.05$ and ##$P<0.01$ vs Ctrl

A

Exogenous *MYBPC3*           Total *MYBPC3*

B

Exogenous cMyBP-C       Total cMyBP-C

C

Exogenous cMyBP-C       Total cMyBP-C

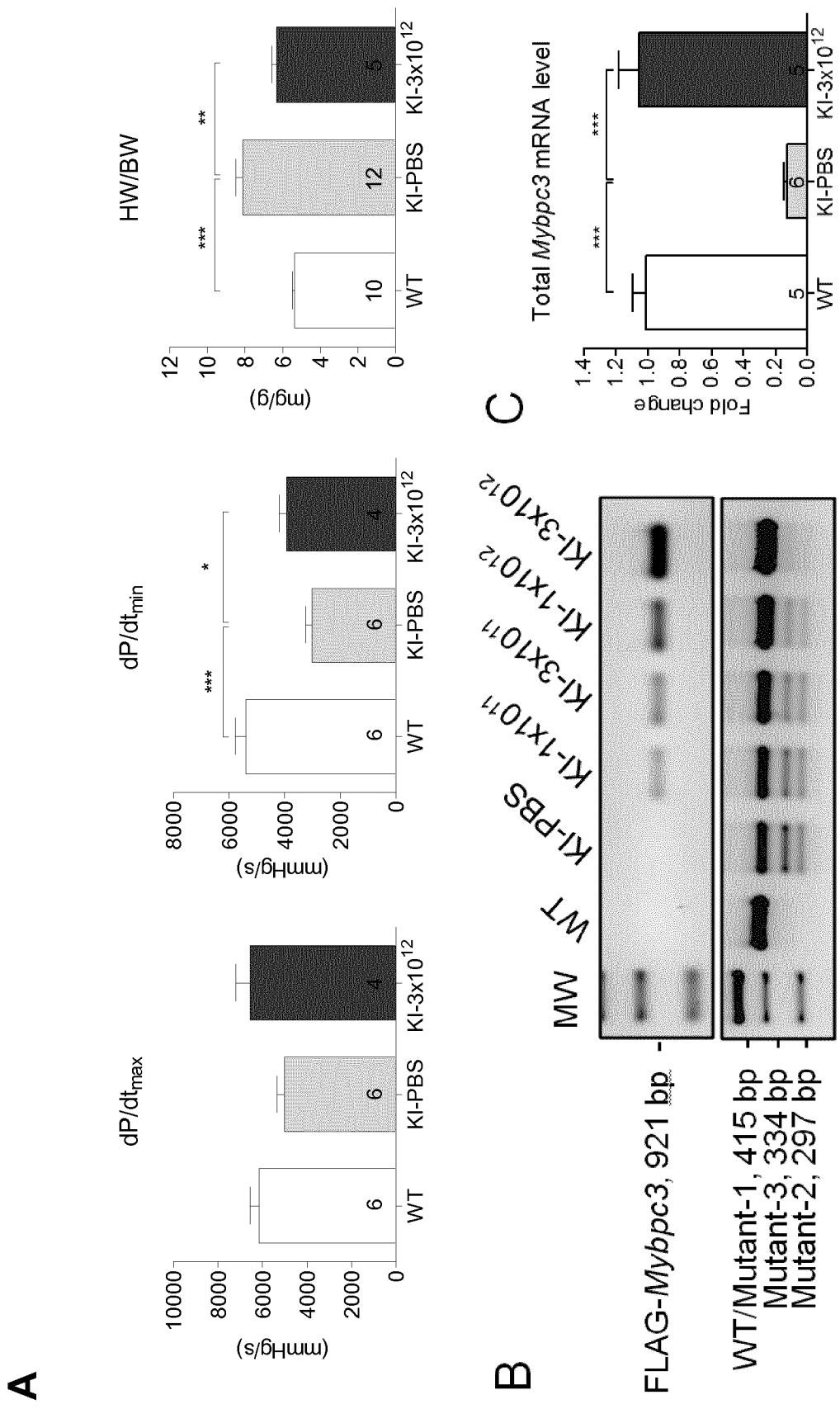
Figure 7.1

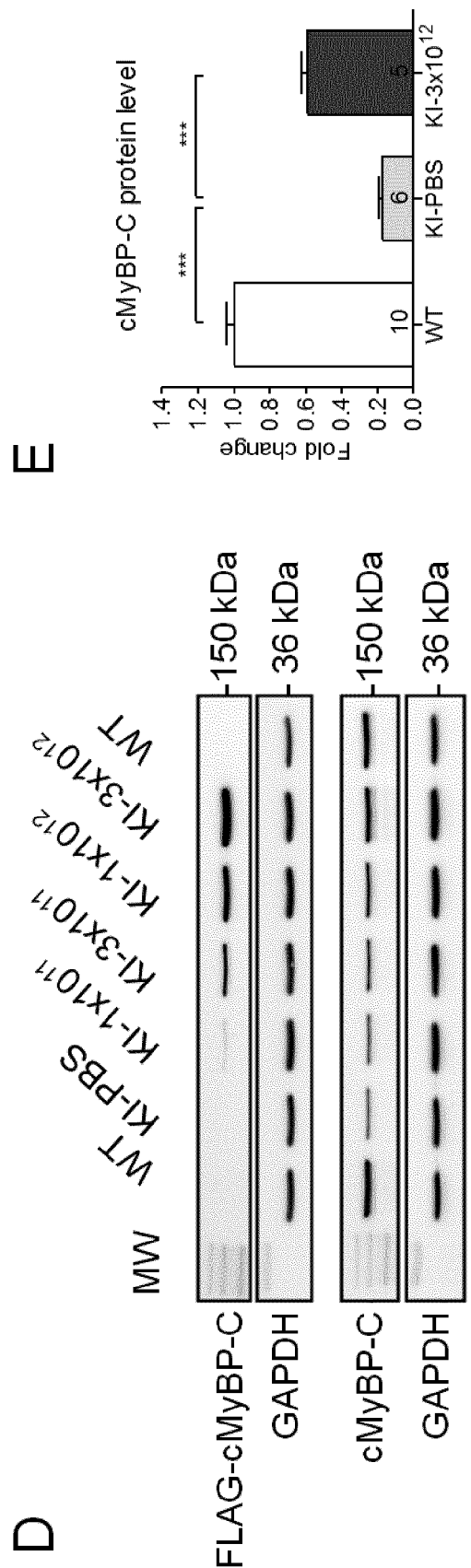
Figure 7.2

GENE-THERAPY VECTORS FOR TREATING CARDIOMYOPATHY

RELATED APPLICATIONS

This application is the National Stage of International Patent Application No. PCT/EP2014/057984, filed Apr. 17, 2014, which is hereby incorporated by reference in its entirety, and which claims priority to European Patent Application No. 13164212.6, filed Apr. 17, 2013, and No. 13198201.9, filed Dec. 18, 2013.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

The present invention relates to a gene therapy vector which is useful in the treatment or prevention of hypertrophic cardiomyopathy in a subject in need thereof. The gene therapy vector of the invention comprises a nucleic acid sequence encoding a cardiac sarcomeric protein and a cardiomyocyte-specific promoter which is operably linked to said nucleic acid sequence. The invention furthermore relates to a cell which comprises the gene therapy vector. Pharmaceutical compositions which comprise the gene therapy vector and/or a cell comprising said vector are also provided. In another aspect, the invention relates to a method for treating or preventing hypertrophic cardiomyopathy in a subject by introducing the gene therapy vector of the invention into a subject in need of treatment.

BACKGROUND OF THE INVENTION

While considerable progress has been made in the prevention of heart diseases that are caused by environmental factors, such as nicotine, hypercholesterolemia or diabetes, and in the symptomatic treatment of heart conditions, there is still a need for methods that improve the treatment of inherited cardiomyopathies. Among the cardiomyopathies that are caused by genetic factors are hypertrophic cardiomyopathy (HCM), dilated cardiomyopathy (DCM), and arrhythmogenic right ventricular cardiomyopathy (ARVC).

HCM is the most prevalent myocardial disease characterized by unexplained left ventricular hypertrophy in the absence of another cardiac or systemic disease that itself would be capable of producing the magnitude of hypertrophy evident in a given patient. HCM is associated with initially normal systolic, but impaired diastolic function (Elliott et al., 2008, Eur Heart J 29:270-276; Gersch et al., 2011, J Thorac Cardiovasc Surg 142:e153-203). HCM has a particularly high prevalence of about 1:500 in the general population (Maron et al., 1995, Circulation 92:785-789), and it is the leading cause of sudden cardiac death in younger people, particularly in athletes. Although HCM is a life-threatening disease, no curative treatment exists to date (Carrier et al., 2010, Cardiovasc Res 85:330-338; Schlossarek et al., 2011, J Mol Cell Cardiol 50:613-20).

HCM is an autosomal-dominant disease which is known to be caused by more than 1000 different mutations in at least 10 genes that encode components of the cardiac sarcomere, such as cardiac myosin binding protein C (MYBPC3), β-myosin heavy chain (MYH7), cardiac troponin T (TNNT2), cardiac troponin I (TNNI3), myosin ventricular essential light chain 1 (MYL3), myosin ventricular regulatory light chain 2 (MYL2), cardiac α actin (ACTC), α-tropomyosin (TPM1), titin (TTN), four-and-a-half LIM protein 1 (FHL1) (Richard et al., 2003, Circulation 107:2227-2232; Schlossarek et al., 2011, J Mol Cell Cardiol 50:613-20; Friedrich et al., 2012, Hum Mol Genet 21:3237-54). Most mutations are missense mutations which encode full-length mutant polypeptides. The most known exceptions are MYBPC3 and FHL1, which exhibit mainly frameshift mutations leading to C-terminal truncated proteins.

The most frequently mutated gene in HCM is MYBPC3 which encodes cardiac myosin binding protein C (cMyBP-C) (Bonne et al., 1995, Nature Genet 11:438-440; Watkins et al., N Engl J Med., 2011, 364:1643-56). cMyBP-C is a major component of the A-band of the sarcomere, where it interacts with myosin, actin and titin (Schlossarek et al., 2011, J Mol Cell Cardiol 50:613-20). In humans and mice cMyBP-C is exclusively detected in the heart (Fougerousse et al, 1998, Circ Res 82:130-133) and is involved in the regulation of cardiac contraction and relaxation (Pohlmann et al., 2007, Circ Res Circ Res 101, 928-38; Schlossarek et al., 2011, J Mol Cell Cardiol 50:613-20). About 70% of the mutations in the MYBPC3 gene result in a frameshift and produce C-terminal truncated proteins (Carrier et al., 1997, Circ Res 80:427-434). Truncated proteins are unstable and have never been detected in myocardial tissue of patients (Marston et al., 2009, Circ Res 105:219-222; van Dijk et al., 2009, Circulation 119:1473-1483; van Dijk et al., 2012, Circ Heart Fail 5:36-46).

Therefore, a reduced level of cMyBP-C protein is one argument that haploinsufficiency is a likely disease mechanism of HCM. An insufficient amount of full-length cMyBP-C could produce an imbalance in the stoichiometry of the thick filament components and alter sarcomeric structure and function. Haploinsufficiency is also involved in mouse and cat models of HCM that carry either missense or frameshift mutations (Meurs et al., 2005, Hum Mol Genet 14:3587-3593; Vignier et al., 2009, Circ Res 105:239-248). In addition, in both cats and mice, there is evidence for the presence of mutant cMyBP-C (full-length or truncated), even at low level. Therefore, a second likely disease mechanism is the generation of toxic polypeptide inducing a dominant-negative effect, most probably by competing with the wild-type (WT) gene product.

Current drug-based treatments of HCM are merely empiric, can alleviate the symptoms but do not treat the genetic cause underlying the disease. Clearly, a gene-based or RNA-based therapy would be the only curative treatment for HCM. Gene therapeutic approaches have successfully been tested in connection with non-genetic cardiac diseases (Jessup et al., 2011, Circulation 124:304-313).

US applications 2005/0276804 and 2007/0292438 disclose that cMyBP-C is associated with genetic cardiac disorders. However, US 2005/0276804 suggests a reduction of retinol binding protein or retinoid to treat these disorders. US 2007/0292438 is limited to the disclosure of different mouse models having disruptions in various genes.

US applications 2004/0086876 and US 2002/0127548 disclose the diagnosis of mutations in the human MYBPC3 gene which are associated with HCM. Further, these applications suggest treating HCM by administration of a nucleic acid which encodes a non-mutated cMyBP-C to the patient.

Merkulov et al., 2012, Circ Heart Fail, 5:635-644 disclose the transfer of the murine Mybpc3 gene into the myocardium of cMyBP-C-deficient (cMyBP-C$^{-/-}$) mice. The authors assume that the absence of cMyBP-C results in dysfunction and hypertrophy. The gene transfer improved systolic and diastolic contractile function and led to reductions in left ventricular wall thickness in the cMyBP-C-deficient (cMyBP-C$^{-/-}$) mice.

Vignier et al., 2009, Circ Res 105:239-248 developed a Mybpc3-targeted knock-in (KI) mouse model carrying a G>A point mutation that results in different mutant mRNAs and proteins originating from abnormal gene transcription and splicing. It was shown that exogenous stress, such as adrenergic stress or aging, leads to a saturation and finally to an impairment of the ubiquitin-proteasome system (UPS) in the KI mice and potentially to a subsequent accumulation of the mutant cMyBP-C polypeptides.

The present inventors found that in subjects suffering from HCM due to a heteroallelic mutation acting in a dominant-negative fashion in a gene encoding a cardiac sarcomeric protein, the introduction of a gene transfer vector which provides the corresponding non-mutated gene not only restores normal levels of the sarcomeric protein, but also minimizes the deleterious effects of toxic mutant polypeptides that are otherwise generated through transcription of mutant allele(s).

A vector-induced expression of an exogenous wild-type (WT) gene under the control of a cardiomyocyte-specific promoter thus overcomes the dominant-negative effect of the mutant protein in a subject which carries a mutated MYBPC3 allele and is not toxic, because, surprisingly, expression of the normal allele via the gene therapy vector effectively reduces the expression of the endogenous mutant allele. This effect is considered to occur as a cardiac cell-autonomous phenomenon due to tight intracellular control of the homeostasis and turnover of sarcomeric proteins.

DESCRIPTION OF THE INVENTION

The invention relates to novel therapeutic approaches for treating or preventing HCM. It is known that mutations in a number of genes which encode cardiac sarcomeric proteins lead to a reduced level of functional full-length sarcomeric protein. This is due to frameshift mutations which produce truncated mutant polypeptides, which are normally degraded by the ubiquitin-proteasome system (UPS). However, under conditions of exogenous stress, the function of the UPS may be disturbed which results in the accumulation of the mutant polypeptides, which can thus be incorporated into the sarcomere and act as a poison peptide in a dominant-negative fashion on the wild-type cMyBP-C, contributing to the pathogenesis of HCM (Vignier et al., 2009, see above). Similar observations have been made for the four-and-a-half LIM protein 1 (Friedrich et al., 2012, Hum Mol Genet 21:3237-3254). A Mybpc3-targeted knock-out, which does not produce any mutant cMyBP-C polypeptides, did not show any impairment of the UPS under the same conditions (Schlossarek et al., 2012, Basic Res Cardiol 107:1-13; Schlossarek et al., 2012, J Muscle Res Cell Motil 33: 5-15.

It is shown herein that gene transfer of wild-type cDNA, which encodes a functional version of a cardiac sarcomeric protein (such as cMyBP-C), via a gene therapy vector into a subject which carries the mutation in the gene of said cardiac sarcomeric protein, not only restores the normal level of the protein in the myocardium (i.e. the muscle tissue of the heart which is constituted by cardiomyocytes), but also prevents the production of toxic mRNAs and/or toxic polypeptides that would otherwise result from expression of the mutated allele encoding the cardiac sarcomeric protein in the genome of said subject. It was also observed that the introduction of high amounts of the gene therapy vector is not associated with a high risk for the patient to be treated, since it was not found to result in excessive amounts of the exogenous wild-type (WT) protein within the cells. Unexpectedly, the expression of cardiac sarcomeric proteins appears to be stochiometrically tightly regulated in the cell which means that it is not possible to provide the exogenous protein in amounts that could be harmful to the patient. Accordingly, the invention provides a simple and safe method for the treatment of HCM in a subject.

The combined effects of providing sufficient levels of normal cDNA resulting in adequate production of the cardiac sarcomeric protein and suppression of the toxic mRNAs/polypeptides result in an effective treatment of HCM. Without wishing to be bound by theory, it is assumed that the exogenous gene expression through the gene therapy vector reduces endogenous expression from the mutated allele by competing for sarcomeric-specific transcription factors.

In a first aspect, the invention therefore provides a gene therapy vector for expressing an exogenous nucleic acid sequence comprising:

(a) a nucleic acid sequence encoding a functional cardiac sarcomeric protein and,
(b) a cardiomyocyte-specific promoter which is operably linked to said nucleic acid sequence.

The gene therapy vector is suitable for use in treating or preventing HCM in a mammalian subject in need of treatment, preferably a human subject. The subject in need of treatment is one that carries a mutation in the corresponding gene encoding said cardiac sarcomeric protein which contributes to HCM. After administration into the subject to be treated, the vector provides for the expression of the encoded cardiac sarcomeric protein in the subject, preferably in the myocardium of said subject.

The cardiac sarcomeric protein to be expressed in the subject is known to be associated with HCM, i.e. mutations in the gene encoding the cardiac sarcomeric protein which lead to expression of a non-functional protein variant, e.g. a full-length or truncated variant or mutant, eventually cause HCM. To date mutations in at least ten different genes encoding cardiac sarcomeric proteins are known to cause HCM. The sarcomere is the basic unit of a muscle and is defined as the segment between two adjacent Z-discs. According to the invention, the sarcomeric protein to be expressed by the gene therapy vector is a cardiac sarcomeric protein which means that the protein naturally occurs in the sarcomere of the cardiac muscle.

The cardiac sarcomeric protein to be expressed in the subject may be a structural or regulatory protein which is present in the cardiac sarcomere. The protein is preferably selected from the group consisting of β-myosin heavy chain (encoded by the gene MYH7, RefSeqGene NG_007884.1), myosin ventricular essential light chain 1 (encoded by the gene MYL3, RefSeqGene NG_007555.2), myosin ventricular regulatory light chain 2 (encoded by the gene MYL2, RefSeqGene NG_007554.1), cardiac α actin (encoded by the gene ACTC1, RefSeqGene NG_007553.1), α-tropomyosin (encoded by the gene TPM1, RefSeqGene NG_007557.1), cardiac troponin T (encoded by the gene TNNT2, RefSeqGene NG_007556.1), cardiac troponin I (encoded by the gene TNNI3, RefSeqGene NG_007866.2), cardiac myosin binding protein C (encoded by the gene MYBPC3, RefSeqGene NG_007667.1), titin (encoded by the gene TTN, RefSeqGene NG_011618.1), and four-and-a-half LIM protein 1 (encoded by the gene FHL1, RefSeqGene NG_015895.1) (Richard et al., 2003, Circulation 107:2227-2232; Friedrich et al., 2012, Hum Mol Genet, 21:3237-54).

It is preferred that the cardiac sarcomeric protein to be expressed by the gene therapy vector of the invention is cardiac myosin-binding protein C (cMyBP-C). The protein can be derived from different species, such as mouse, cat, pig or monkey. In one preferred embodiment of the invention, the cMyBP-C protein to be expressed is a murine cMyBP-C, preferably a murine cMyBP-C having the amino acid sequence depicted in SEQ ID NO:4 (NCBI accession number: NP_032679.2) of the enclosed sequence listing or a sequence having at least 80% sequence identity thereto. The nucleotide sequence encoding the murine cMyBP-C of SEQ ID NO:4 is depicted in SEQ ID NO:3 (NCBI accession number: NM_008653.2).

The present invention particularly envisages the treatment of human patients suffering from HCM. Thus, in another preferred embodiment of the invention, the nucleic acid inserted in the vector which encodes a human cMyBP-C protein is of human origin. Preferably, the human cMyBP-C protein has the amino acid sequence depicted in SEQ ID NO:2 (NCBI accession number: NP_000247.2) or a sequence having at least 80% sequence identity thereto. The nucleotide sequence encoding the human cMyBP-C protein is shown in SEQ ID NO:1 (NM_000256.2).

The protein to be expressed may also be a functional variant of one of the above-mentioned proteins which exhibits a significant amino acid sequence identity compared to the original protein. Preferably, the amino acid identity amounts to at least 60%, 65%, 70%, 75%, 80%, 85%, 90%, 95%, 96%, 97%, 98%, or 99%. Preferably, the amino acid identity of the variant is at least 70%, 80% or 90%. In this context, the term "functional variant" means that the variant of the sarcomeric protein is capable of fulfilling the function of the naturally occurring cardiac sarcomeric protein, e.g. providing structural/functional support.

Functional variants of a cardiac sarcomeric protein may include, for example, proteins which differ from their naturally occurring counterparts by one or more amino acid substitutions, deletions or additions. For example, a variant protein of the human cMyBP-C protein depicted in SEQ ID NO:2 may have an amino acid sequence with 2, 3, 4, 5, 6, or up to 10, 20, 30 or more positions which have been substituted by another amino acid relative to SEQ ID NO:2. For example, the functional variant may e.g. be selected from the group consisting of the naturally occurring Mybpc3 splice variant lacking exons 5 and 6, termed variant 4 (as shown in SEQ ID NO:28).

The amino acid substitutions can be conservative or non-conservative. It is preferred that the substitutions are conservative substitutions, i.e. a substitution of an amino acid residue by an amino acid of similar polarity, which acts as a functional equivalent. Preferably, the amino acid residue used as a substitute is selected from the same group of amino acids as the amino acid residue to be substituted. For example, a hydrophobic residue can be substituted with another hydrophobic residue, or a polar residue can be substituted with another polar residue having the same charge. Functionally homologous amino acids which may be used for a conservative substitution comprise, for example, non-polar amino acids such as glycine, valine, alanine, isoleucine, leucine, methionine, proline, phenylalanine, and tryptophan. Examples of uncharged polar amino acids comprise serine, threonine, glutamine, asparagine, tyrosine and cysteine. Examples of charged polar (basic) amino acids comprise histidine, arginine and lysine. Examples of charged polar (acidic) amino acids comprise aspartic acid and glutamic acid.

Also considered as variants are proteins which differ from their naturally occurring counterparts by one or more (e.g. 2, 3, 4, 5, 10, or 15) additional amino acids. These additional amino acids may be present within the amino acid sequence of the original sarcomeric protein (i.e. as an insertion), or they may be added to one or both termini of the protein. Basically, insertions can take place at any position if the addition of amino acids does not impair the capability of the polypeptide to fulfill the function of the naturally occurring cardiac sarcomeric protein and/or rescue the haploinsufficiency in the treated subject. Moreover, variants of sarcomeric proteins also comprise proteins in which, compared to the original polypeptide, one or more amino acids are lacking. Such deletions may affect any amino acid position provided that it does not impair the ability to fulfill the normal function of the cardiac sarcomeric protein and/or rescue the haploinsufficiency.

Finally, variants of the cardiac sarcomeric proteins also refer to proteins which differ from the naturally occurring protein by structural modifications, such as modified amino acids. According to the invention, modified amino acids are amino acids which have been modified either by natural processes, such as processing or post-translational modifications, or by chemical modification processes known in the art. Typical amino acid modifications comprise phosphorylation, glycosylation, acetylation, 0-Linked N-acetylglucosamination, glutathionylation, acylation, branching, ADP ribosylation, crosslinking, disulfide bridge formation, formylation, hydroxylation, carboxylation, methylation, demethylation, amidation, cyclization and/or covalent or non-covalent bonding to phosphotidylinositol, flavine derivatives, lipoteichonic acids, fatty acids or lipids. Such modifications have been extensively described in the literature, e.g., in Proteins: Structure and Molecular Properties, T. Creighton, $2^{nd}$ edition, W. H. Freeman and Company, New York (1993). In a preferred embodiment of the invention, the nucleic acid sequence encodes a constitutively phosphorylated isoform of human cMyBP-C. It has been shown that these isoforms are particularly cardioprotective (Sadayappan et al. (2005), Circ Res 97:1156-1163; Sadayappan et al., 2006; Proc Natl Acad Sci U S A 103:16918-16923).

The gene therapy vector is preferably for treating or preventing HCM in a subject in need thereof. The subject to be treated with the vectors can be a subject that has been diagnosed with HCM, a subject with an increased risk for developing HCM, or a subject predisposed to develop HCM. In a preferred aspect of the invention, the subject is a human subject diagnosed with HCM as a result of a mutation in at least one of the alleles of a gene encoding a cardiac sarcomeric protein which is known to be associated with HCM.

In another preferred aspect of the invention, the subject which is treated with the vector of the invention carries a gene mutation that impairs the function of said cardiac sarcomeric protein and, as a result of the mutation, produces one or more dysfunctional protein species which originate from the cardiac sarcomeric protein.

In another preferred aspect of the invention, the mutation in the cardiac sarcomeric protein causes haploinsufficiency in said subject. Haploinsufficiency designates a state of a diploid organism, which is characterized by one dysfunctional allele, wherein the remaining functional allele does not produce a sufficient level of the gene product to generate the wild-type phenotype.

The present invention is based on the surprising insight that the phenotype of HCM can be effectively ameliorated or eradicated by administration of a gene therapy vector which provides an intact, exogenous version of the wild-type gene which compensates for the mutated allele in the genome of the subject to be treated. It was unexpectedly found that an accumulation of toxic mRNA and/or polypeptides (both of which derive from the mutated allele) can be effectively prevented. Thus, in one embodiment, the described gene therapy vector is for use in a method of treating or preventing hypertrophic cardiomyopathy in a mammalian subject, wherein said subject produces one or more dysfunctional protein species which originate from the cardiac sarcomeric protein and, optionally, wherein administration of said therapy results in the reduction of one or more of the dysfunctional protein species. "Reduction" refers to a level of one or more of the dysfunctional protein species which is reduced by more than 20%, 30%, 40%, 50%, 60%, 70%, 80%, or 90%, compared to the level before administration. In a preferred embodiment, the level of one or more of the dysfunctional protein species is reduced by more than 20% compared to the level before administration.

Preferably, the "level of one or more of the dysfunctional protein species" is the level of all dysfunctional species of the sarcomeric protein combined, i.e. the overall level of dysfunctional species of the sarcomeric protein.

HCM describes a deterioration of the heart muscle which results in a decreased integrity. This may lead to heart rhythm disorder and ultimately to heart failure. HCM is a genetically and clinically heterogeneous disease of the sarcomere characterized inter alia by a thickening of the muscular walls in the ventricular septum and left ventricle in the absence of another cardiac or systemic disease that itself would be capable of producing the magnitude of hypertrophy evident in a given patient. As a consequence of the wall thickening, the left ventricle outflow tract may be narrowed. Characteristics of HCM are myocyte hypertrophy, myocellular disarray, interstitial fibrosis, small vessel coronary disease, and/or left ventricular outflow obstruction. HCM is associated with initially normal systolic, but impaired diastolic function in majority of cases. Thus, in a preferred embodiment of the invention, the gene therapy vector is for treating or preventing HCM in a subject in need thereof, wherein HCM is characterized by a thickening of the muscular walls in the ventricular septum and/or left ventricle and diastolic dysfunction.

When expressing a cardiac sarcomeric protein, e.g. one of the proteins mentioned above, exogenously in the subject to which the therapeutic vector has been administered, it may turn out that it is not necessary to express the full-length protein to compensate for the dysfunctional mutant protein expressed from the mutated allele. Instead, it may be sufficient to express only a functional fragment of the full-length sarcomeric protein or its variants as defined above. Thus, the present invention also comprises the use of functional fragments of the cardiac sarcomeric protein or their variants for treating or preventing HCM in a subject in need thereof. As used herein, fragments of cardiac sarcomeric proteins of the invention are proteins which differ from the naturally occurring protein by the lack of one or several amino acids at the N-terminus and/or the C-terminus, wherein at least part of the ability to fulfill the normal function of the naturally occurring cardiac sarcomeric protein is retained.

The nucleic acid sequence encoding the cardiac sarcomeric protein is administered to the subject to be treated in the form of a gene therapy vector, i.e. a nucleic acid construct which comprises the coding sequence, including the translation and termination codons, next to other sequences required for providing expression of the exogenous nucleic acid such as promoters, kozak sequences, polyA signals and the like. Gene therapy vectors for expressing an exogenous nucleic acid sequence in a subject are well known in the art.

For example, the gene therapy vector may be part of a mammalian expression system. Useful mammalian expression systems and expression constructs have been described in the prior art. Also, several mammalian expression systems are distributed by different manufacturers and can be employed in the present invention, such as plasmid- or viral vector based systems, e.g. LENTI-Smart™ (InvivoGen), GenScript™ Expression vectors, pAdVAntage™ (Promega), ViraPower™ Lentiviral, Adenoviral Expression Systems (Invitrogen) and adeno-associated viral expression systems (Cell Biolabs).

The gene therapy vector of the invention can be, for example, a viral or non-viral expression vector which is suitable for introducing the exogenous nucleic acid into a cell for subsequent expression of the protein encoded by said nucleic acid. The vector should be specifically adapted to provide expression of the encoded sarcomeric protein in a cardiomyocyte. In a preferred embodiment the vector provides specific expression of the encoded sarcomeric protein in cardiomyocytes. The expression is "specific" when the expression is at least 2-fold higher than in other non-cardiac cell type or cardiac cell which is not a cardiomyocte.

The expression vector can be an episomal vector, i.e. one that is capable of self-replicating autonomously within the host cell, or an integrating vector, i.e. one which stably incorporates into the genome of the cell. The expression in the host cell can be constitutive or regulated (e.g. inducible). Preferably, the functional exogenous cardiac sarcomeric protein is located intracellularly, preferably in the sarcomere of the host cell.

A gene therapy vector of the invention will normally comprise a promoter which is functionally linked to the nucleic acid encoding the sarcomeric protein. The promoter sequence must be compact and ensure a strong expression. Preferably, the promoter provides for an expression of the sarcomeric protein in the myocardium of the patient that has been treated with the gene therapy vector. More preferably, the promoter provides for a specific expression of the sarcomeric protein in the myocardium of the patient. The expression is "specific" when the expression is at least 2-fold higher than in cells do not belong to the myocardium. It is further preferred that substantially no sarcomeric protein is expressed in cells that do not belong to the myocardium. "Substantially no" in this context means that less than 10%, less than 5%, less than 1% of the sarcomeric protein that is expressed from the vector is expressed in cells that do not belong to the myocardium.

Suitable promoters include, for example, the muscle creatine kinase (MCK), the cytomegalovirus enhancer+myosin light chain 2 promoter (CMV-MLC2, or CMV-MLC1.5, CMV-MLC260), the phosphoglycerate kinase (PGK), and the cardiac troponin T promoter (TNNT2), and any other sarcomere-specific promoters. Preferably, these promoters are derived from human genes.

In a particularly preferred embodiment, the gene therapy vector comprises a cardiac-specific promoter which is operably linked to the nucleic acid sequence encoding the cardiac sarcomeric protein. As used herein, a "cardiac-specific promoter" refers to a promoter whose activity in cardiac cells is at least 2-fold higher than in any other non-cardiac cell type. Preferably, a cardiac-specific promoter suitable for being used in the vector of the invention has an activity in cardiac cells which is at least 5-fold, at least 10-fold, at least 15-fold, at least 20-fold, at least 25-fold, or at least 50-fold higher compared to its activity in a non-cardiac cell type.

In a further preferred embodiment, the gene therapy vector comprises a cardiomyocyte-specific promoter which is operably linked to the nucleic acid sequence encoding the cardiac sarcomeric protein. A "cardiomyocyte-specific promoter", as used herein, specifies a promoter whose activity in cardiomyocytes is at least 2-fold higher than in any other non-cardiac cell type or cardiac cell which is not a cardiomyocte. Preferably, a cardiomyocyte-specific promoter suitable for being used in the vector of the invention has an activity in cardiomyocytes which is at least 5-fold, at least 10-fold, at least 15-fold, at least 20-fold, at least 25-fold, or at least 50-fold higher compared to its activity in a non-cardiac cell type or a cardiac cell type which is not a cardiomyocte.

Preferably, the cardiac-specific or cardiomyocyte-specific promoter is a human promoter. As can be seen from the enclosed examples, one promoter that has been proven useful for the vectors of the invention is a cardiac troponin T promoter (TNNT2), such as the human TNNT2 promoter set forth in SEQ ID NO:5. Accordingly, the cardiomyocyte-specific promoter of the invention preferably comprises the sequence of SEQ ID NO:5 or a functional equivalent sequence having at least 80%, more preferably 90%, 95%, 96%, 97%, 98%, 99%, sequence identity thereto. In a preferred embodiment, the gene therapy vector comprises a TNNT2 promoter operably linked to the nucleic acid sequence encoding the cardiac sarcomeric protein. In a further preferred embodiment, the gene therapy vector comprises the human TNNT2 promoter of SEQ ID NO:5 operably linked to the nucleic acid sequence encoding the cardiac sarcomeric protein. Other cardiac-specific promoters include the alpha myosin heavy chain promoter, the myosin light chain 2v promoter, the alpha myosin heavy chain promoter, the alpha-cardiac actin promoter, the alpha-tropomyosin promoter, the cardiac troponin C promoter, the cardiac troponin I promoter, the cardiac myosin-binding protein C promoter, and the sarco/endoplasmic reticulum $Ca^{2+}$-ATPase (SERCA) promoter (e.g. isoform 2 of this promoter (SERCA2)).

Cardiac muscle tissue is striated muscle tissue that has repeating sarcomeres. Thus, in a further embodiment the gene therapy vector comprises a striated muscle promoter, such as the desmin promoter.

The cardiac-specific or cardiomyocyte-specific promoter is operably linked to the nucleic acid sequence encoding the cardiac sarcomeric protein which means that the promoter is combined with the coding nucleic acid so as to enable the expression of said coding nucleic acid under the control of the promoter in cardiac myocytes cells when integrated into the genome of the cell or present as an extragenomic nucleic acid construct in the cell.

As an optional component, the gene therapy vector can include an enhancer element for increasing the expression level of the sarcomeric protein. Examples include the SV40 early gene enhancer and the enhancer of the long terminal repeat (LTR) of Rous Sarcoma Virus (Gorman et al. (1982) Proc. Natl. Acad. Sci. 79:6777). The vector also optionally comprises transcription termination sequences and polyadenylation sequences for improved expression of the human and/or non-human antigen(s). Suitable transcription terminator and polyadenylation signals can, for example, be derived from SV40 (Sambrook et al (1989), Molecular Cloning: A Laboratory Manual). Preferably, a SV40 polyadenylation signal comprising or consisting of the sequence of SEQ ID NO:6 is used in the vector of the invention. Any other element which is known in the art to support efficiency or specificity of expression may be added to the expression vector, such as the Woodchuck hepatitis post-transcriptional regulatory element (wPRE). To increase the cardiac specificity, other elements can be introduced to inactivate the expression of genes in other tissues, such as sequences encoding miRNAs such as miR122 (Geisler et al., 2011, Gene Therapy 18:199-209). To visualize the exogenous gene expression in the heart, other optional elements can be introduced such as tag sequences (myc, FLAG, HA, His, and the like), or fluorochromes such as GFP, YFP, RFP.

To further increase the gene expression level, a chimeric intron can be introduced into the gene therapy vector of the invention. A "chimeric intron" as used herein refers to an intron that comprises parts of at least two different introns which have been derived from two different genes. Particularly preferred chimeric introns for use in the gene therapy vector of the present invention comprise, e.g. intron sequences from the human beta globin gene and human immunoglobulin G (IgG). An exemplary intron is depicted in SEQ ID NO:7. Preferably, the chimeric intron is inserted immediately downstream from the promoter. It has e.g. been shown that insertion of the beta globin/Ig intron immediately downstream of the PGK promoter increases gene expression about 37-fold (Dominguez et al., 2011, Hum Mol Genet 20:681-693).

The gene therapy vector can be constructed and cloned by standard methods known in the art, such as recombinant DNA technology or chemical synthesis. Standard cloning methods are described e.g. in Sambrook et al., 1989, Molecular Cloning: A Laboratory Manual, Cold Spring Harbour Lab Press.

In a particularly preferred aspect, the gene therapy vector is a viral expression vector. Viral vectors for use in the present invention typically comprise a viral genome in which a portion of the native sequence has been deleted in order to introduce a heterogeneous polynucleotide without destroying the infectivity of the virus. Due to the specific interaction between virus components and host cell receptors, viral vectors are highly suitable for efficient transfer of genes into target cells. Suitable viral vectors for facilitating gene transfer into a mammalian cell are well known in the art and can be derived from different types of viruses, for example, from a retrovirus, adenovirus, adeno-associated virus (AAV), orthomyxovirus, paramyxovirus, papovavirus, picornavirus, lentivirus, herpes simplex virus, vaccinia virus, pox virus or alphavirus. For an overview of the different viral vector systems, see Nienhuis et al., Hematology, Vol. 16: Viruses and Bone Marrow, N. S. Young (ed.), 353-414 (1993).

For example, retroviral vectors may be used. Retroviral vectors normally function by transducing and integrating the selected polynucleotide into the genome of the target cell. The retroviral vectors can be derived from any of the subfamilies. For example, vectors from Murine Sarcoma Virus, Bovine Leukemia, Virus Rous Sarcoma Virus, Murine Leukemia Virus, Mink-Cell Focus-Inducing Virus, Reticuloendotheliosis Virus, or Avian Leukosis Virus can be used. The skilled person will be able to combine portions derived from different retroviruses, such as LTRs, tRNA binding sites, and packaging signals to provide a recombinant retroviral vector. These retroviral vectors are then normally used for producing transduction competent retroviral vector particles. For this purpose, the vectors are introduced into suitable packaging cell lines, such as those described in U.S. Pat. No. 5,591,624. Retrovirus vectors can also be constructed for site-specific integration into the DNA of the host cell by incorporating a chimeric integrase enzyme into the retroviral particle. See, for example, WO 96/37626.

According to the invention, it is particularly preferred that the gene therapy vector is an adeno-associated viral (AVV) vector, such as an AAV vector selected from the group consisting of serotype 1, 2, 3, 4, 5, 6, 7, 8, 9, and 10 or chimeric AAV derived thereof, which will be even better suitable for high efficiency transduction in the tissue of interest (Wu et al., 2006, Mol Therapy 14:316-27; Bowles et al., 2012, Mol Therapy 20:443-455). Upon transfection, AAV elicits only a minor immune reaction (if any) in the host. Moreover, in contrast to other vector systems AAV vectors are also able to efficiently pass from the blood into terminally differentiated cardiomyocytes. In this respect the AAV system is superior e.g. to the use of lentivirus. Therefore, AAV is highly suited for gene therapy approaches. For transduction in mice, AAV serotype 6 and AAV serotype 9 are particularly suitable. For gene transfer into a human, AAV serotypes 1, 6, 8 and 9 are preferred. Thus, in a preferred embodiment of the invention, the gene therapy vector is an AAV serotype 6 vector. In a further preferred embodiment, the gene therapy vector is an AAV serotype 8 vector. Finally, it is most preferred that the gene therapy vector is an AAV serotype 9 vector. The AAV serotype 9 vector is particularly well suited for the induction of expression in cells of the myocardium/cardiomyocytes.

It was assumed in the prior art that the capacity of AAV for packaging a therapeutic gene is limited to approximately 4.9 kbp, while longer sequences lead to truncation of AAV particles (Wu et al., 2010, Mol Ther 18:80-86). However, it is demonstrated herein that packaging of an oversized DNA sequence of 5.4 kbp (including two inverted terminal repeats (ITRs), the FLAG-tagged Mybpc3 cDNA under the control of the human TNNT2 promoter, a chimeric intron and the SV40 polyadenylation signal) does not affect the production of the AAV serotype 6 or 9. Titers of $1-7 \times 10^{12}$ vector genomes per mL were achieved and the vectors induced marked expression of the FLAG-Mybpc3 gene in isolated mouse cardiac myocytes and in the mouse heart in vivo. Thus, in a preferred embodiment, the gene therapy vector comprises a polynucleotide sequence having a size of at least 4.0 kbp, at least 4.5 kbp, at least 5 kbp, at least 5.1 kbp, at least 5.2 kbp, at least 5.3 kbp, at least 5.4 kbp, at least 5.5 kbp or at least 5.6 kbp. In one embodiment, the gene therapy vector comprises a polynucleotide sequence having a size of at least 4.5 kbp. It is particularly preferred that the gene therapy vector comprises a polynucleotide sequence having a size of at least 5 kbp. In a further embodiment the gene therapy vector comprises a polynucleotide sequence having a size of at least 5.3 kbp.

Moreover, the gene therapy vectors of the invention preferably combine the advantages of a highly efficient and pharmaceutically acceptable transfection vector, such as AAV, with a cardiomyocyte-/myocardium-specific expression of the encoded cardiac sarcomeric protein, through a cardiac-specific promoter. Therefore, it is preferred that the gene therapy vector is an AAV vector that comprises a cardiac-specific promoter which is operably linked to the nucleic acid sequence encoding the cardiac sarcomeric protein. In a first preferred embodiment, the AAV vector is an AAV serotype 6. In a second preferred embodiment, the AAV vector is an AAV serotype 8. In a third preferred embodiment, the AAV vector is an AAV serotype 9. It is particularly preferred that the cardiac-specific promoter in any of these embodiments is the human TNNT2 of SEQ ID NO:5 or a functional equivalent sequence having at least 80%, more preferably 90%, 95%, 96%, 97%, 98%, 99%, sequence identity thereto. For example, the gene therapy vector is an AAV 9 vector that comprises a cardiac-specific promoter which is operably linked to the nucleic acid sequence encoding the cardiac sarcomeric protein, wherein the cardiac-specific promoter in any of these embodiments is the human TNNT2 of SEQ ID NO:5 or a functional equivalent sequence having at least 80%, more preferably 90%, 95%, 96%, 97%, 98%, 99%, sequence identity thereto.

As outlined above, the cardiac sarcomeric protein that is encoded by the gene therapy vector is preferably cardiac myosin-binding protein C (cMyBP-C). As shown in the below examples, a gene therapy vector combining the advantages of an AAV vector, a cardiomyocyte-specific promoter and expression of cardiac myosin-binding protein C is highly efficient in the treatment of patients suffering from HCM.

Thus, in a preferred embodiment, the gene therapy vector is an AAV serotype 9 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding a cMyBP-C, preferably a murine cMyBP-C having the amino acid sequence depicted in SEQ ID NO:4 or a sequence having at least 80% sequence identity thereto, or the human cMyBP-C protein having the amino acid sequence depicted in SEQ ID NO:2 or a sequence having at least 80% sequence identity thereto. In a more preferred embodiment, the gene therapy vector is an AAV serotype 9 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding the human cMyBP-C protein having the amino acid sequence depicted in SEQ ID NO:2 or a sequence having at least 80% sequence identity thereto.

Thus, in another embodiment, the gene therapy vector is an AAV serotype 6 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding a cMyBP-C, preferably a murine cMyBP-C having the amino acid sequence depicted in SEQ ID NO:4 or a sequence having at least 80% sequence identity thereto, or the human cMyBP-C protein having the amino acid sequence depicted in SEQ ID NO:2 or a sequence having at least 80% sequence identity thereto. In a more preferred embodiment, the gene therapy vector is an AAV serotype 6 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding the human cMyBP-C protein having the amino acid sequence depicted in SEQ ID NO:2 or a sequence having at least 80% sequence identity thereto.

Thus, in another embodiment, the gene therapy vector is an AAV serotype 8 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding a cMyBP-C, preferably a murine cMyBP-C having the amino acid sequence depicted in SEQ ID NO:4 or a sequence having at least 80% sequence identity thereto, or the human cMyBP-C protein having the amino acid sequence depicted in SEQ ID NO:2 or a sequence having at least 80% sequence identity thereto. In a more preferred embodiment, the gene therapy vector is an AAV serotype 8 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding the human cMyBP-C protein having the amino acid sequence depicted in SEQ ID NO:2 or a sequence having at least 80% sequence identity thereto.

Recombinant viral vectors can be generated according to standard techniques. For example, recombinant adenoviral or adeno-associated viral vectors can be propagated in human 293 cells (which provide E1A and E1B functions in trans) to titers in the range of $10^7$-$10^{13}$ viral particles/mL. Prior to their in vivo application viral vectors may be desalted by gel filtration methods, such as sepharose columns, and purified by subsequent filtering. Purification reduces potential deleterious effects in the subject to which the vectors are administered. The administered virus is substantially free of wild-type and replication-competent virus. The purity of the virus can be proven by suitable methods, such as sodium dodecyl sulfate-polyacrylamide gel electrophoresis (SDS-PAGE) followed by silver staining. This is applicable for both AAV and adenoviral vectors.

As described in the below examples, transduction of the gene therapy vectors of the invention into the subject to be treated can be achieved by systemic application, e.g., by intravenous, intraarterial or intraperitoneal delivery of a vector in analogy to what has been shown in animal models (Katz et al., 2012, Gene Ther 19:659-669. In a preferred embodiment, the gene therapy vectors are for use in the described method of treating or preventing hypertrophic cardiomyopathy, wherein the gene therapy vector is administered systemically.

Alternatively, the gene therapy vectors of the invention can be delivered by direct administration to the heart tissue, e.g. by intracoronary administration. In a preferred embodiment, the gene therapy vectors are administered as a single dose by antegrade epicardial coronary artery infusion over a 10-minute period in a cardiac catheterization laboratory after angiography (percutaneous intracoronary delivery without vessel balloon occlusion) with the use of standard 5F or 6F guide or diagnostic catheters (Jaski et al., 2009, J Card Fail 15:171-181).

In another preferred embodiment, tissue transduction of the myocardium is achieved by catheter-mediated intramyocardial delivery (Gao et al., 2011, Hum Gene Ther 22:979-84). Importantly, this latter form of delivery can also be used to transfer vector-free cDNA coupled or not to transduction-enhancing carriers into myocardium. Cell-derived exosomes or microparticles with cardiac tropism can also be used to transport the vectors of the invention (Lee et al., 2012, Hum Mol Genet 21:R125-134). A suitable dose of AAV for humans would be in the range of about $1 \times 10^{10}$ to $1 \times 10^{14}$ virus particles, and in particular about $1 \times 10^{12}$.

Apart from viral vectors, non-viral expression constructs may also be used for introducing a gene encoding a functional cardiac sarcomeric protein or a functioning variant or fragment thereof into a cell or a human subject. Non-viral expression vectors which permit the in vivo expression of protein in the target cell include, for example, vectors such as pBK-CMV, pcDNA3.1, and pZeoSV (Invitrogen, Stratagene). Suitable methods for the transfer of non-viral vectors into target cells are, for example, the lipofection method, the calcium-phosphate co-precipitation method, the DEAE-dextran method and direct DNA introduction methods using micro-glass tubes and the like. Prior to the introduction of the vector, the cardiac muscle cells may be treated with a permeabilization agent, such as phosphatidylcholine, streptolysins, sodium caprate, decanoylcarnitine, tartaric acid, lysolecithin, Triton X-100, and the like.

Alternatively, isolated cells that have been removed from a subject, for example, by a biopsy procedure, may be transfected with the vector in an ex vivo procedure. The cells can then be re-implanted into or otherwise administered to a subject, preferably into the subject from whom they were obtained. In another aspect, the invention thus relates to an isolated cell, such as a cardiomyocyte or a stem cell, which has been transduced with the gene therapy vector of the invention. After transduction of the vector, the cell expresses the cardiac sarcomeric protein that was encoded by the vector. The cell preferably is a cardiac cell, such as a cardiomyocyte, or a cardiomyocyte derived from induced pluripotent stem cell (iPSC). The cell may also be a stem cell, preferably an embryonal or pluripotent adult stem cell, more preferably an endogenous cardiac stem cells (eCSCs) or an iPSC derived from fibroblasts (Okita et al., 2007, Nature 448:313-7; Yu et al., 207, Science 318:1917-20; Maekawa et al., 2011, Nature 474: 225-229), from keratinocytes (Aasen et al., 2008, Nat Biotech 11:1276-1284; Aasen & Belmonte, 2010, Nat Protocol 5:371-382) or from blood cells (Staerk et al., 2010, Stem Cell Stem 7: 20-24; Seki et al., 2012, Nat Protocol 7:718-728).

It is furthermore preferred that the cell is a human cell. The likelihood of rejection of transplanted cells is reduced when the subject from whom the cell is explanted is genetically similar to the subject to whom the cell is administered. Therefore, the cell of the invention is preferably an autologous cell that is transduced with the gene therapy vector of the invention ex vivo. After transduction of the autologous cell, the cell is reintroduced into the subject by appropriate administration means, such as transplantation or infusion.

The cell is preferably for use in a method of treating or preventing HCM in a subject, wherein mutations in the gene encoding said cardiac sarcomeric protein are associated with HCM and the subject carries a gene mutation that impairs the function of said cardiac sarcomeric protein.

The invention further relates to a pharmaceutical composition comprising the gene therapy vector of the invention. In a preferred embodiment, the composition is for use in a method of treating or preventing HCM in a subject having a dysfunctional cardiac sarcomeric protein.

Methods for the preparation of pharmaceutical compositions that contain gene therapy vectors are well known by those working in the field of pharmaceutics. Typically, such compositions are prepared either as liquid solutions or suspensions. The pharmaceutical composition of the invention can include commonly used pharmaceutically acceptable excipients, such as diluents and carriers. In particular, the composition comprises a pharmaceutically acceptable carrier, e.g., water, saline, Ringer's Solutions, or dextrose solution. Further examples of suitable carriers are described in standard textbooks, for example, in "Remington's Pharmaceutical Sciences", Mack Pub. Co., New Jersey (1991). In addition to the carrier, the composition may also contain emulsifying agents, pH buffering agents, stabilizers, dyes and the like.

The pharmaceutical composition will comprise a therapeutically effective gene dose. A therapeutically effective gene dose is one that is capable of preventing or treating cardiomyopathy in a subject, without being toxic to the subject. Prevention or treatment of cardiomyopathy can be assessed as a change in a phenotypic characteristic associated with cardiomyopathy, such change being effective to prevent or treat cardiomyopathy. Phenotypic characteristics associated with cardiomyopathy are for example left ventricular (LV) hypertrophy, reduced fractional shortening, interstitial fibrosis as well as diastolic and systolic dysfunction. A therapeutically effective gene dose typically elicits a positive change in the phenotype of HCM, i.e. a change that approximates the phenotype of the subject suffering from HCM to the phenotype of a healthy subject which does not carry a HCM gene mutation. Thus, a therapeutically effective gene dose is typically one that, when administered in a physiologically tolerable composition, is sufficient to improve or prevent the pathogenic heart phenotype in the treated subject.

In yet another aspect, the invention relates to methods for treating or preventing HCM in a subject by introducing a gene therapy vector for expressing an exogenous nucleic acid sequence in a subject, said vector comprising:
(a) a nucleic acid sequence encoding a cardiac sarcomeric protein as defined elsewhere herein, and
(b) a cardiomyocyte-specific promoter which is operably linked to said nucleic acid sequence,
wherein mutations in the gene encoding said cardiac sarcomeric protein are associated with HCM and said subject carries a gene mutation that impairs the function of said cardiac sarcomeric protein.

BRIEF DESCRIPTION OF THE FIGURES

FIG. 7 (FIG. 7.1 shows graphs/blots A-C; FIG. 7.2 shows graphs/blots D-E): Long-term Mybpc3 gene therapy in Mybpc3-targeted knock-in mice. Different doses of adeno-associated virus serotype 9 (AAV9)-Mybpc3 ($1\times10^{11}$, $3\times10^{11}$, $1\times10^{12}$ and $3\times10^{12}$ vector genomes (vg)/mouse) or PBS were administered to 1-day-old Mybpc3-targeted knock-in (KI) mice, before the appearance of the cardiac disease phenotype. All data were obtained after 34 weeks. (A) Analysis of systolic (=dP/dtmax) and diastolic (=dP/dtmin) function and determination of the heart weight to body weight ratio (HW/BW) were performed in 34-week-old WT, KI treated with PBS and KI mice treated with the highest dose of $3 \times 10^{12}$ vg. (B) RT-PCR for evaluation of the mRNA levels of exogenous FLAG-tagged Mybpc3 (upper panel) and total Mybpc3 (lower panel). RNA was extracted from ventricular tissues and pooled in each group (n=5-10/group). The size of the PCR-amplified bands is shown on the left side. (C) Total Mybpc3 mRNA level determined by RT-qPCR performed in 34-week-old WT, KI treated with PBS and KI mice treated with the highest dose of $3 \times 10^{12}$ vg. (D) Western blot for evaluation of the protein levels of exogenous FLAG-tagged cMyBP-C (upper panels) and total cMyBP-C (lower panels). Ventricular protein extracts from each group were pooled for the analysis. Blots were stained with antibodies directed against the FLAG epitope or total cMyBP-C (upper part in each condition). An antibody directed against GAPDH was used as loading control (lower parts in each condition). (E) Quantification of cMyBP-C protein level normalized to GAPDH and related to WT.

EXAMPLES

Example 1

Consequences of a G>A Transition in Homozygous Mybpc3-targeted Knock-in Mice

For both ex vivo and in vivo studies, a knock-in mouse carrying a G>A transition in the Mybpc3 gene (Mybpc3-targeted knock-in; KI) has been developed by gene targeting using the Cre/lox system (Vignier et al., 2009, Circ Res 105:239-248). Briefly, a 8105 bp-fragment containing the 5' part of mouse Mybpc3 gene, which covers 1747 bp upstream of exon 1 up to exon 15, was obtained by long-range PCR or cloning from a FIX II genomic library derived from a 129/Svj mouse strain, and then cloned into the pBluescript® II KS+ vector (Stratagene). The G>A transition on the last nucleotide of exon 6 was obtained by site-directed mutagenesis (Stratagene) on a 258 bp PCR fragment, which was then cloned into the Eco47RI/Nsi I sites.

The phenotype of KI mice appeared normal and they were viable for up to two years (Vignier et al., 2009, Circ Res, 105:239-248). Echocardiography was performed on wild-type (WT) and homozygous KI mice using the Vevo 2100 System (VisualSonics, Toronto, Canada). Mice were anesthetized with isofluorane (1-2%) and fixed to a warming platform in a supine position. B-mode images were obtained using a MS400 transducer for adult mice and a MS550 transducer for neonatal mice. Images were obtained in a parasternal short and long axis view and dimensions of the left ventricle were measured in a short axis view in diastole and systole. KI mice exhibited left ventricular hypertrophy, reduced fractional shortening and interstitial fibrosis compared to WT mice at 3-4 months after birth (Vignier et al., 2009, Circ Res, 105:239-248).

Figure 1:
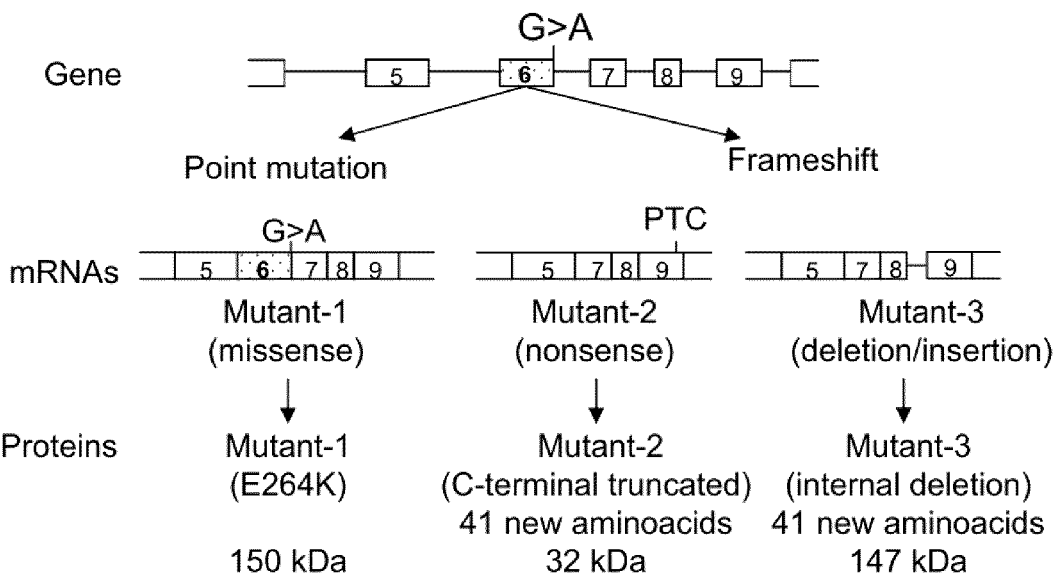
FIG. 1: Cardiac molecular analysis in Mybpc3-targeted knock-in (KI) and wild-type (WT) mice. (A) The G>A transition in the Mybpc3 gene was obtained using the Cre/lox system and resulted in three different mutant mRNAs in KI mice. (B) Total Mybpc3 mRNA level in WT and homozygous KI mouse ventricular tissue. (C) cMyBP-C protein level in WT and KI ventricular tissue, determined by Western blot using a specific antibody. Number of mice is indicated in the bars.
Figure 1:
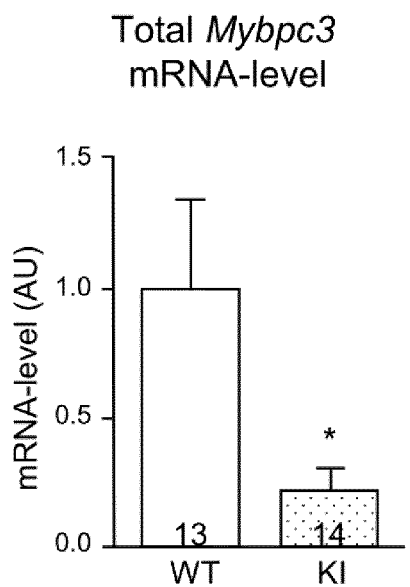
Figure 1:
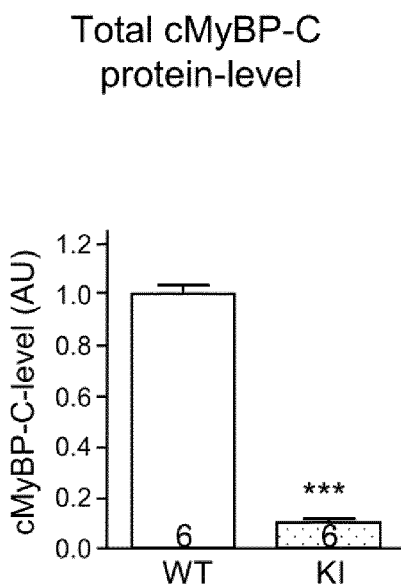

The G>A transition resulted in three different mutant mRNAs (see FIG. 1A). Mutant 1 (missense) contains the G>A transition and produces an E264K mutant protein of about 150 kDa. Mutant 2 (nonsense) is a result from the skipping of exon 6, which leads to a frameshift and a premature termination codon (PTC) in exon 9. The expected protein is 32 kDa. Mutant 3 also results from the skipping of exon 6 and a partial retention of intron 8, which restores the reading frame. In this case, a 147 kDa-mutant protein is produced. None of these mutants encodes a functional protein.

RNA or protein was extracted from ventricular tissue of homozygous KI and WT mice. Total RNA was isolated from ventricular tissue (30 mg) using the SV Total RNA Isolation System Kit (Promega) according to the manufacturer's instructions. RNA concentration, purity and quality were determined using the NanoDrop® ND-1000 spectrophotometer (Thermo Scientific). Reverse transcription (RT) was performed from 150-200 ng RNA using oligo-dT primers (SuperScript®-III kit, Life Technologies). Quantitative polymerase chain reaction (qPCR) was performed using primers #1 (forward: 5'-GGA TTA CAA GGA TGA CGA CGA-3'; SEQ ID NO:9) and #2 (reverse: 5'-TCC AGA GTC CCA GCA TCT TC-3'; SEQ ID NO:10) and SYBR green. The level of total Mybpc3 mRNA was 80% lower in homozygous KI mice than in wild WT mice (FIG. 1B).

Crude protein extract was obtained from about 15 mg of ventricular tissue homogenized in 5% SDS, 50 mM Tris-HCl, pH 7.5, 250 mM sucrose, 75 mM urea, 1 mM DTT at 4° C. and centrifuged at 13000 rpm for 2 min. The supernatant was collected and its concentration was determined using the BCA Protein Assay Kit (Pierce). Proteins were loaded on 10%-acrylamide/bisacrylamide (29:1) gels and electrotransferred on a 0.45 µm pore size nitrocellulose membrane (Invitrogen). Membranes were stained with a polyclonal antibody directed against cMyBP-C(C0-C1 1:1, 000). The secondary antibody was coupled to HRP (Sigma). Signal was revealed with SuperSignal® West Pico chemiluminescent substrate (Pierce) and acquired with a Chemi-Imager™ 5500 (Alpha Innotech). Quantification of the signal was done using the NIH Image 1.63 software. Homozygous Mybpc3-targeted knock-in mice expressed only low levels of mutant proteins (FIG. 1C).

The results show that the presence of low levels of cMyBP-C proteins (=haploinsufficiency), including mutant polypeptides (=poison-polypeptides) results in left ventricular hypertrophy and dysfunction, which are hallmarks of HCM.

Example 2

Generation of a FLAG-Mybpc3-containing Vector

Figure 2:
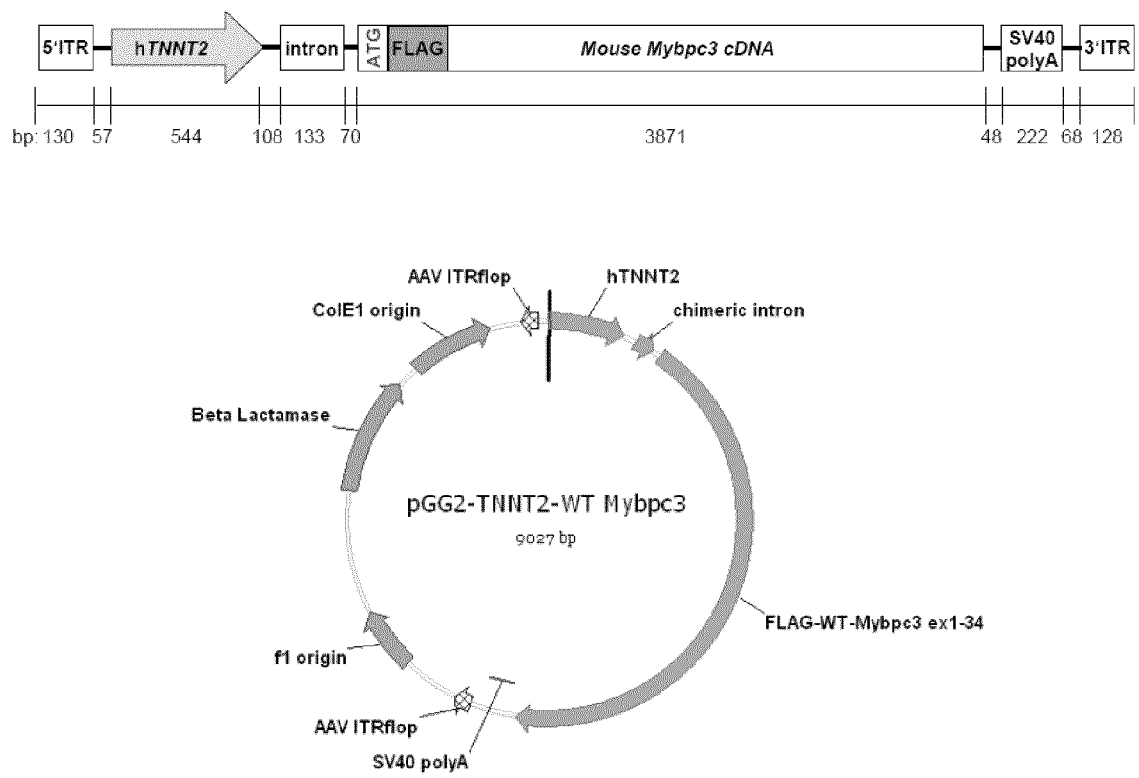
FIG. 2: Schematic linear (upper panel) and circular (lower panel) representations of the pGG2 vector expressing FLAG-tagged mouse Mybpc3 under the control of the human cardiac troponin T promoter (hTNNT2).

The vector pGG2-hTNNT2-WT-Mybpc3 was constructed by first amplifying the full-length FLAG-tagged mouse Mybpc3 cDNA (GenBank accession number NM_008653.2) including exons 1-34 by RT-PCR from mouse ventricular RNA using the forward primer #3 (5'-TTC GAC CTC GAG ATG GAT TAC AAG GAT GAC GAC GAT AAG CCT GGT GTG ACT GTT CTC AA-3'; SEQ ID NO:11) containing the XhoI restriction site and the FLAG sequence and reverse primer #4 (5'-TTC GAC GGA TCC CTG GTC ACT GAG GAA CTC G-3'; SEQ ID NO:12) containing BamHI restriction site. The human cardiac troponin T (hTNNT2) 5' region from base −502 to +42 (GenBank accession number NG_007556.1; SEQ ID NO:5) was originally amplified from a human cDNA library by PCR using forward primer #5 (5'-AAA AAA ACG CGT CTC AGT CCA TTA GGA GCC AGT AGC-3'; SEQ ID NO:13) and reverse primer #6 (5'-CCC CCC CAA GCT TCT GCC GAC AGA TCC TGG AGG CG-3'; SEQ ID NO:14) enabling cloning with MluI/HindIII restriction enzymes in a plasmid containing a renilla luciferase reporter gene (pdsTNNT2(−502 +42)-Rluc) and the chimeric (□-globin/Ig) intron, which has been shown to increase gene expression (Dominguez et al., 2011, Hum Mol Genet 20, 681-93). For generation of the pGG2-hTNNT2-WT-Mybpc3 plasmid the hTNNT2 promoter and the chimeric intron (SEQ ID NO:7;

FIG. 2) were excised with the restriction enzymes EcoRI and NheI and ligated into the pGG2 plasmid vector containing the SV polyA signal (SEQ ID NO:6). Together the vector has a size of 9027 bp (FIG. 2), including 5.4 kbp of insert between two ITRs (FIG. 2), which exceeds the packaging capacity of adeno-associated virus (AAV; Wu et al., 2010, Mol Ther 18:80-86).

AAV6 and AAV9 pseudotyped vectors were produced with the two (AAV6; Muller et al., 2006, Cardiovasc Res 70:70-78) or the three (AAV9; Kaya et al., 2011, Cardiovasc Res 91:116-123) plasmids transfection method. AAV6 pseudotyped vectors were generated by co-transfection of HEK293T cells with the pGG2-hTNNT2-WT-Mybpc3 transfer plasmid and the AAV packaging plasmid pDP6rs, which provides the AAV2 rep and AAV6 cap genes and adenoviral helper functions (Grimm et al., 2003, Mol Ther, 7:839-850). AAV9 pseudotyped vectors were generated by triple-transfection of pGG2-hTNNT2-WT-Mybpc3 transfer plasmid with p5E18-VD2-9 and pDGdeltaVP encoding adenoviral helper functions (Kaya et al., 2011, Cardiovasc Res 91:116-23). Generation of recombinant AAV6 and AAV9 particles was carried out as described previously (Grieger et al., 2006, Nat Protoc 1:1412-1428), with some modifications. Plasmids were transfected into 293T HEK cells in cell stacks or in plates with a diameter of 15 cm using polyethylenimine (PEI) as described before (Hauswirth et al., 2000, Methods Enzymol 316:743-761). The HEK293T-AAV cells were cultivated in DMEM, High Glucose supplemented with 10% (v/v) heat-inactivated fetal calf serum, 0.1 mM MEM non-essential amino acids, 2 mM L-glutamine, 100 UI/ml penicillin and 100 µg/ml streptomycin. Tissue culture reagents were obtained from Life technologies. Cells were harvested after 72 h, washed three times with phosphate-buffered saline (PBS). After three freeze-thaw cycles, benzonase (Merck; 250 U/ml) was added for 1 h at 37° C. Cell debris was pelleted and vector-containing lysates were purified using iodixanol step gradients (Hauswirth et al., 2000, Methods Enzymol 316:743-761).

The genomic titers of DNase-resistant AAV particles were determined by qPCR using the SYBR Green qPCR Master MIX 2 (Fermentas) and an ABI PRISM® 7900HT cycler (Applied Biosystem) as reported before (Veldwijk et al., 2002, Mol Ther 6:272-278). Vectors were quantified using primers #7 (forward: 5'-CTC AGT CCA TTA GGA GCC AGT-3'; SEQ ID NO:15) and #8 (reverse: 5'-AAG GCA ACC TCC AAG ACA CT-3; SEQ ID NO:16) specific for TNNT2 promoter sequence. Real-time PCR was performed in a total volume of 10 µl with 0.3 µM for each primer. The pdsAAV-TNNT2-eGFP plasmid was used as a copy number standard. A standard curve for quantification was generated by serial dilutions of the respective plasmid DNA. The cycling conditions were as follows: 50° C./2 min, 95° C./10 min, followed by 35 cycles of 95° C./15 sec and 60° C./60 sec. Calculations were done using the SDS 2.4 software (Applied Biosystem).

Example 3

Evaluation of Mybpc3 mRNA and cMyBP-C Protein Levels and Localisation After Gene Transfer in Cardiac Myocytes Isolated from Mybpc3-targeted Neonatal KI Mice Neonatal mouse cardiac myocytes were isolated from neonatal mouse hearts as previously described (Vignier et al., 2009, Circ Res 105:239-248). Cardiac myocytes were immediately transduced with AAV6-FLAG-Mybpc3 under the control of hTNNT2 at a multiplicity of infection (MOI) of 3000 for 30 min at 37° C. in suspension prior to plating ($4.4 \times 10^5$ cells/well). Cardiac myocytes were kept in culture for 7 days at 37° C. and 10% $CO_2$ prior to harvesting.

HEK293 cells were plated at a density of $2 \times 10^5$ cells in 12-well dishes in DMEM (10% FCS, 1% penicillin-streptomycin) and incubated at 37° C. with 7% $CO_2$ until the recommended confluence of 50-70% was reached. The transient transfection of FLAG-Mybpc3 plasmid into adherent HEK293 cells was performed using the TurboFect transfection reagent (Fermentas) according to the manufacturer's protocol.

Figure 3:
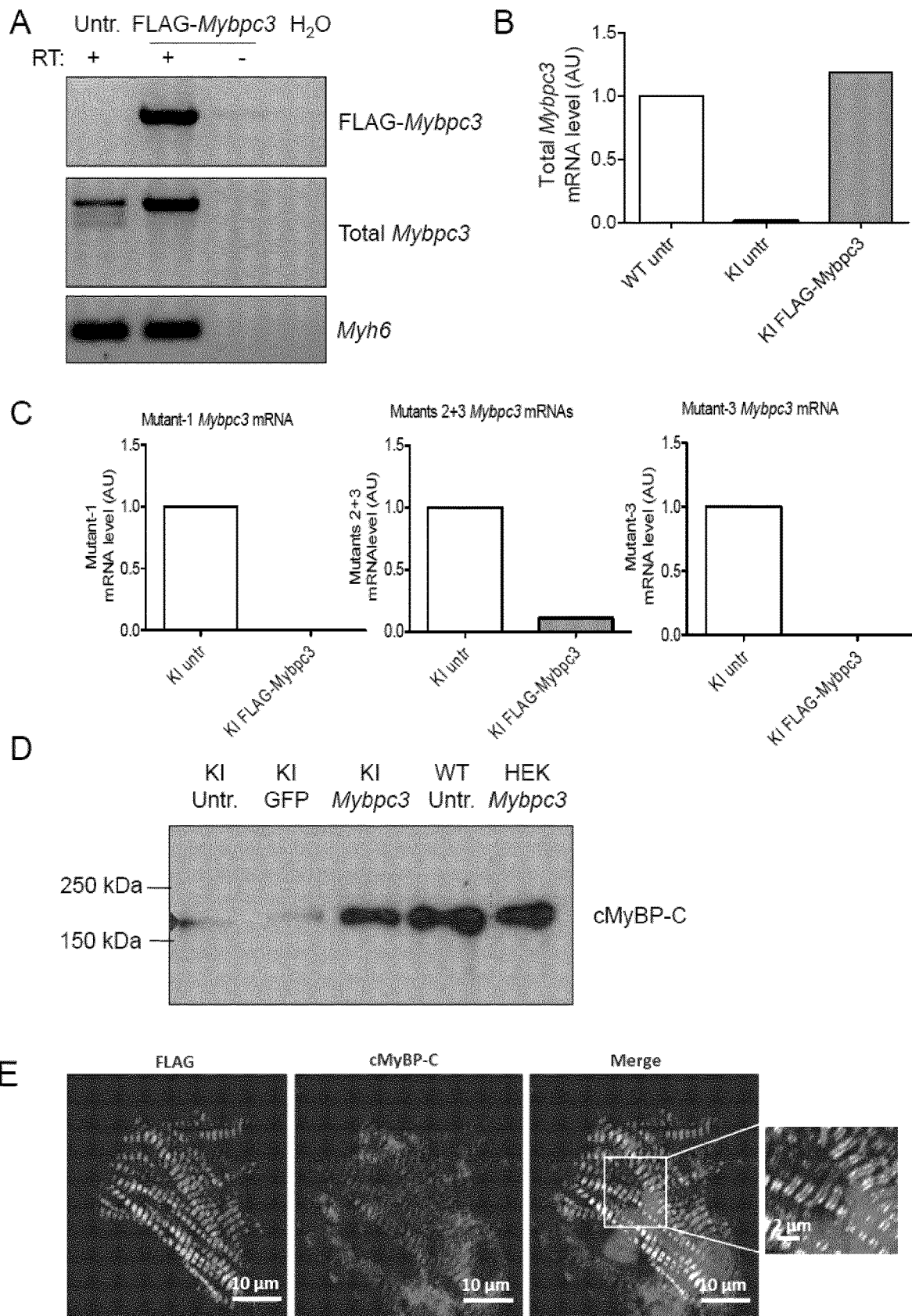
FIG. 3: AAV6-mediated FLAG-Mybpc3 gene transfer using adeno-associated virus serotype 6 in cardiac myocytes isolated from Mybpc3-targeted knock-in (KI) neonatal mice. (A) RT-PCR of FLAG-Mybpc3 (exogenous Mybpc3 mRNA), total Mybpc3 (endogenous and exogenous Mybpc3 mRNAs) and Myh6 (encoding α-myosin-heavy chain) mRNAs performed in KI ventricular RNA. "–RT" indicates no reverse transcriptase during the cDNA reaction. (B) RT-qPCR of total Mybpc3 evaluated in cardiac myocytes isolated from wild-type (WT) and KI neonatal mice, which were transduced (KI FLAG-Mybpc3) or untransduced (KI untr) with AAV6-FLAG-Mybpc3. (C) RT-qPCR detecting the different mutant Mybpc3 mRNAs. (D) Western blot performed with an anti-cMyBP-C antibody on protein lysates extracted from WT cardiac myocytes, KI cardiac myocytes, or from HEK293 (HEK) cells, which were transduced with GFP (GFP), or with FLAG-Mybpc3 (Mybpc3) or not transduced (untr.). (E) Immunofluorescence analysis of FLAG-Mybpc3-transduced KI neonatal mouse cardiomyocytes (NMCMs). Cardiac myocytes were fixed 7 days after transduction (MOI 3,000) and double-stained with anti-FLAG (FLAG) and anti-cMyBP-C (cMyBP-C) antibodies. Nuclei were stained with DRAQ5™. The merge picture including its higher magnification is shown on the right panel. Scale bars are indicated.

Total RNA was isolated from cultured cardiac myocytes using the SV Total RNA Isolation System Kit (Promega) according to the manufacturer's instructions. RNA concentration, purity and quality were determined using the Nano-Drop® ND-1000 spectrophotometer (Thermo Scientific). RT was performed from 150-200 ng RNA using oligo-dT primers (SuperScript®-III kit, Life Technologies). As a control for genomic contamination a reaction without RT was performed. Touch-down PCR amplifications (65° C.-60° C.) were performed using AmpliTaq® Gold Polymerase (Applied Biosystems) in a total volume of 20 µl for 35 cycles with different primer pairs:

FLAG-Mybpc3 mRNA was amplified using forward primer #9 (5'-GGA TTA CAA GGA TGA CGA CGA-3'; SEQ ID NO:17) and reverse primer #10 (5'-TCC AGA GTC CCA GCA TCT TC-3'; SEQ ID NO:18); total Mybpc3 mRNA was amplified with forward primer #11 (5'-CCT GGT GTG ACT GTT CTC AA-3'; SEQ ID NO:19) and reverse primer #12 (5'-TCC AGA GTC CCA GCA TCT TC-3'; SEQ ID NO:20); Myh6 mRNA (encoding α-myosin heavy chain) was amplified with forward primer #13 (5'-CTC AAG CTC ATG GCT ACA CTC TTC TC-3'; SEQ ID NO:21) and reverse primer #14 (5'-AGA GCA GAC ACT GTT TGG AAG GA-3'; SEQ ID NO:22). PCR products were visualized on 1.5% agarose gels (FIG. 3A). In untransduced cells (Untr.), only mutant mRNAs were detected (total Mybpc3 panel). In contrast, after AAV6-FLAG-Mybpc3 gene transfer in KI cardiac myocytes, FLAG-Mybpc3 mRNA was detected (FLAG-Mybpc3 panel) and was associated with a reduced level of mutant mRNAs (total Mybpc3 panel). The level of Myh6 did not differ between the groups (Myh6 panel). Quantitative PCR using forward primer #15 (5'-GAT GCG AGC CCT GAT GAC-3'; SEQ ID NO:23) and reverse primer #16 (5'-GAC TTG AGA CAC TTT CTT CC-3'; SEQ ID NO:24) and SYBR green demonstrated further that the level of total Mybpc3 mRNA in KI cardiac myocytes transduced with AAV6-FLAG-Mybpc3 reached the level found in WT cardiac myocytes (FIG. 3B). Moreover, quantitative PCR using specific hydrolysing Taqman probes were performed to determine the level of the different mutant mRNAs: Mutant-1 was revealed with probe #1 (5'-VIC-CTC ACT GTC CAT AAG G-MGB-3'; SEQ ID NO:25), mutants 2+3 with probe #2 (5'-FAM-CCA GCA AGA GGC CA-MGB-3'; SEQ ID NO:26) and mutant 3 with probe #3 (5'-FAM-TCG GAG AAC CAG CCC CTG CTA GCT C-TAMRA-3'; SEQ ID NO:27). This shows that mutant-1 and mutant-3 mRNA are completely absent, whereas levels of mutant-2 mRNA are markedly reduced in KI cardiac myocytes from KI transduced with AAV6-FLAG-Mybpc3 (FIG. 3C).

Crude proteins from transduced cultured cardiac myocytes or transfected HEK293 cells were extracted in lysis buffer (30 mM Tris base pH 8.8, 5 mM EDTA, 30 mM NaF, 3% SDS, 10% glycerol) and protein concentration was determined by Bradford protein assay (BioRad). Total proteins (cardiac myocytes 30 μg/lane, HEK293 2.5 μg/lane) were separated on 10% SDS-polyacrylamide (29:1) minigels (BioRad) and transferred on PVDF membranes by electroblotting. Membranes were stained overnight with the primary antibody directed against the MyBP-C motif of cMyBP-C (1:1,000). After incubation with anti-rabbit (1:6,000, Sigma) peroxidase-conjugated secondary antibodies, proteins were visualized using Super Signal® West Dura detection reagent (Thermo Scientific) and signals were detected with the ChemiGenius[2] Bio Imaging System. Western blot analysis shows a specific cMyBP-C band in all lanes. Furthermore, the cMyBP-C levels in AAV6-FLAG-Mybpc3-transduced KI cardiac myocytes reached the levels found in untransduced WT cardiac myocytes (FIG. 3D).

Figure 4:
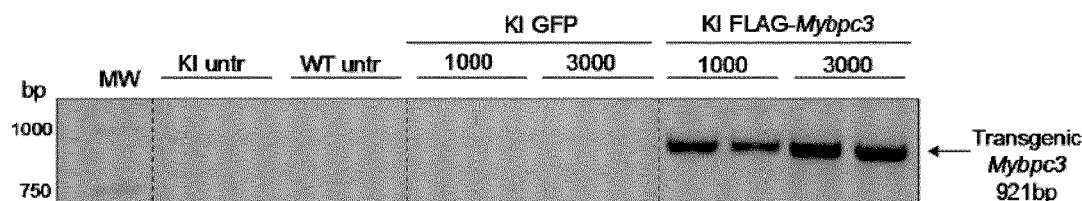
FIG. 4: AAV6-mediated FLAG-Mybpc3 gene transfer in engineered heart tissue (EHT) derived from Mybpc3-targeted knock-in (KI) cardiac cells. (A) RT-PCR from EHT RNA performed using specific primers to detect only FLAG-Mybpc3 mRNA. (B) RT-PCR of total Mybpc3 mRNA. (C) Spontaneous contractile activity of EHT determined at days 7, 9, 14 and 19 of culture. Data are expressed as mean±SEM. *P<0.05 and **P<0.01 vs. GFP; #P<0.05 and ##P<0.01 vs Ctrl.
Figure 4:
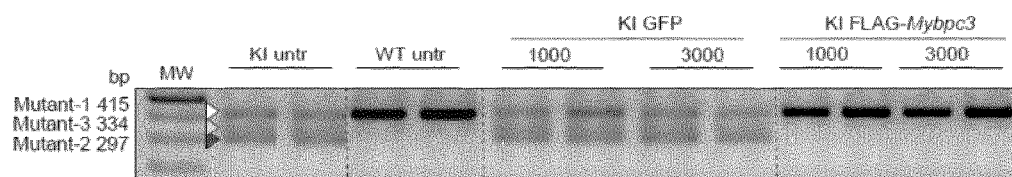
Figure 4:
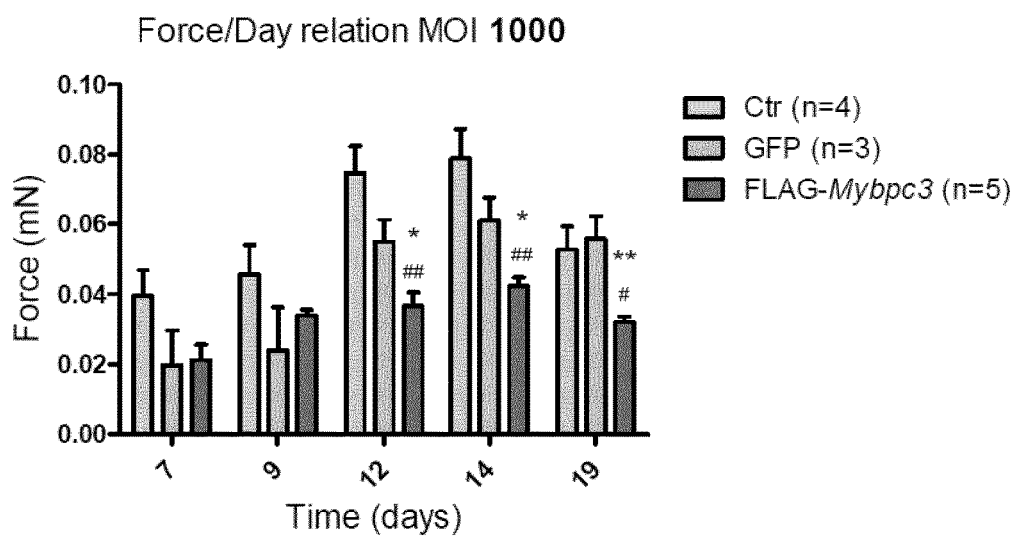

Immunofluorescence analysis was performed in order to examine the localization of the transgenic FLAG-tagged cMyBP-C protein (FIG. 4D). KI cardiac myocytes transduced with AAV6-TNNT2-FLAG-WT-Mybpc3 (MOI 3,000) were analyzed by confocal microscopy after fixation of the cells and staining with antibodies directed against the FLAG epitope and total full-length cMyBP-C protein. Immunofluorescence of transduced cardiac myocytes using the anti-cMyBP-C antibody showed the classic striation pattern of total cMyBP-C protein located in doublets in the A-band of the sarcomere (FIG. 4D, cMyBP-C). Furthermore, FLAG-positive signal (FIG. 4D; FLAG) colocalized with cMyBP-C protein striation, confirming the correct sarcomeric incorporation of the transgenic FLAG-tagged cMyBP-C protein.

These data demonstrate that Mybpc3 gene transfer in KI cardiac myocytes rescues cMyBP-C haploinsufficiency and at the same time prevents transcription of mutant alleles and accumulation of toxic mutant cMyBP-C proteins.

Example 4

Expression of Endogenous Mutant and Exogenous Wild-type Mybpc3 after Gene Transfer in Engineered Heart Tissues Derived from Mybpc3-targeted KI Neonatal Hearts Hearts derived from wild-type (WT) and Mybpc3-targeted knock-in (KI) neonatal mice were taken (postnatal day 0-1) for cell isolation using a trypsin/collagenase overnight digestion (Laugwitz et al., 2005, Nature 433:647-653; Moretti et al., 2006, Cell 127:1151-65). To generate engineered heart tissue (EHT), a reconstitution mix was prepared on ice as follows (final concentration): Unpurified $6.8 \times 10^6$ cells/ml, 5 mg/ml bovine fibrinogen (stock solution: 200 mg/ml plus aprotinin, 0.5 μg/mg fibrinogen in NaCl 0.9%, Sigma F4753), 100 μl/ml Matrigel (BD Bioscience 356235). 2×DMEM was added to match the volumes of fibrinogen and thrombin stock (100 U/ml, Sigma Aldrich T7513) to ensure isotonic conditions. Casting molds were prepared as previously described (Hansen et al., 2010, Circ Res 107:35-44).

AAV6-FLAG-Mybpc3 or AAV6-FLAG-GFP, or a control without virus was added directly into the EHT master mix before casting, at a MOI of 1000 or 3000. The volume of 2×DMEM was adapted to the volume of virus to maintain isotonic conditions. For each EHT a 97-μl-reconstitution mix was mixed briefly with 3 μl thrombin and pipetted into the agarose slot. For fibrinogen polymerization, the constructs were placed in a 37° C., 7% $CO_2$ humidified cell culture incubator for 2 h. The racks were transferred to 24-well plates filled with culture medium. EHTs were kept in a 37° C., 7% $CO_2$ humidified cell culture incubator. Cell culture medium was changed after 48 h and consisted of DMEM (Biochrom F0415), 10% horse serum (Gibco 26050), 2% chick embryo extract, 1% Penicillin/Streptomycin (Gibco 15140), insulin (10 μg/ml, Sigma-Aldrich I9278) and aprotinin (33 μg/ml, Sigma Aldrich A1153). On day 5 of the EHT culture, cytosine β-D-arabinofuranoside (25 μg/ml, Sigma-Aldrich C1768) was added to the culture medium for 48 h. Spontaneous contractile activity of EHTs was monitored from day 7 to day 19 via video-optical recording (Hansen, et al., 2010, Circ Res 107, 35-44). Contraction graphs were automatically recorded and evaluated. The CTMV software (Pforzheim, Germany) was used to measure spontaneous contractions of murine EHTs as recently published (Hansen et al., 2010, Circ Res 107:35-44; Stöhr et al., 2013, J Mol Cell Cardiol 63:189-98). For this purpose, the 24-well plate was placed in a cell incubator unit with control of $CO_2$, humidity and temperature, and a glass roof for monitoring purposes. A Basler camera (Type A 602f-2) was placed above the cell culture unit in a PC-controlled manner. During measuring time the distance between the ends of the muscle strip was recorded during contractions. The force was calculated according to a recently published equation (Vandenburgh et al., 2008, Muscle Nerve, 37:438-47) based on post geometry, elastic modulus of Sylgard 184 (Dow Corning) and delta of post distance (post deflection). Squares in recorded contraction graphs indicated the identified peaks, which were taken for frequency, average force, contraction and relaxation times (T1, T2, respectively) calculation. T1 and T2 were determined at 10% of peak maximum. At the end of the experiments, EHTs were removed from posts, and total RNA was extracted.

FLAG-Mybpc3 mRNA was amplified as described in the Example 3 and detected only in transduced EHTs, and its level increased with increasing MOI (FIG. 4A). In addition, PCR amplification of all types of Mybpc3 mRNAs (Total Mybpc3, as described in Example 3) revealed that (FIG. 4B): i) the different mutant mRNAs were detected at a similar level in both untransduced KI-EHT and in EHT transduced with AAV6-GFP; ii) FLAG-Mybpc3 gene transfer in KI EHTs lead to a single type of mRNA. The level of this mRNA did not differ from the level detected in WT-EHT. This shows that gene transfer of FLAG-Mybpc3 repaired the mRNA haploinsufficiency and reduced the content of mutant mRNAs in EHT derived from KI neonatal cardiac cells.

Spontaneous contractile activity of EHTs was monitored from day 7 to day 19 of culture via video optical recording (FIG. 4C). In all groups, maximum force was reached at 14 days. The developed force is higher in KI (about 65 μN) than in WT EHTs (about 40 μN, data not shown), indicating hypercontractility. The developed force was significantly lower after Mybpc3 gene transfer in KI EHT than in other groups (FIG. 4C), reaching levels previously found in WT EHTs.

Together, these data show that gene transfer of FLAG-Mybpc3 in EHT derived from KI neonatal cardiac cells rescues both the molecular phenotype (no haploinsufficiency and no mutant mRNAs) and the function (absence of hypercontractility).

Example 5

Expression of Endogenous Mutant and Exogenous Wild-type Mybpc3 after Gene Transfer in Mybpc3-targeted KI Neonatal Mice All experimental in vivo studies were in accordance with the guidelines for the care and use of laboratory animals published by the NIH (Publication No. 85-23, revised 1985) as well as the German Law for the Protection of Animals and accepted by the Ministry of Science and Public Health of the City State of Hamburg, Germany (Nr. 69/10).

AAV9-FLAG-Mybpc3 ($5\times10^{12}$ vector genomes (vg)) or PBS as a control were administered in 3-day-old mice via temporal vein injection using a 30-G needle (Sands and Barker, 1999, Lab Anim Sci, 49:328-330) as described previously (Dominguez et al., 2011, Hum Mol Genet 20:681-693). All mice recovered quickly from the injection. The cardiac phenotype was evaluated every week from 3 weeks of age by echocardiography (see details in Example 1). The mice were sacrificed at 7 weeks of age and different organs were extracted. RNA and proteins were extracted. FLAG-Mybpc3 and total Mybpc3 mRNAs in ventricles, liver and skeletal muscle were evaluated by RT-PCR as described in Example 3 (FIG. 5A).

Figure 5:
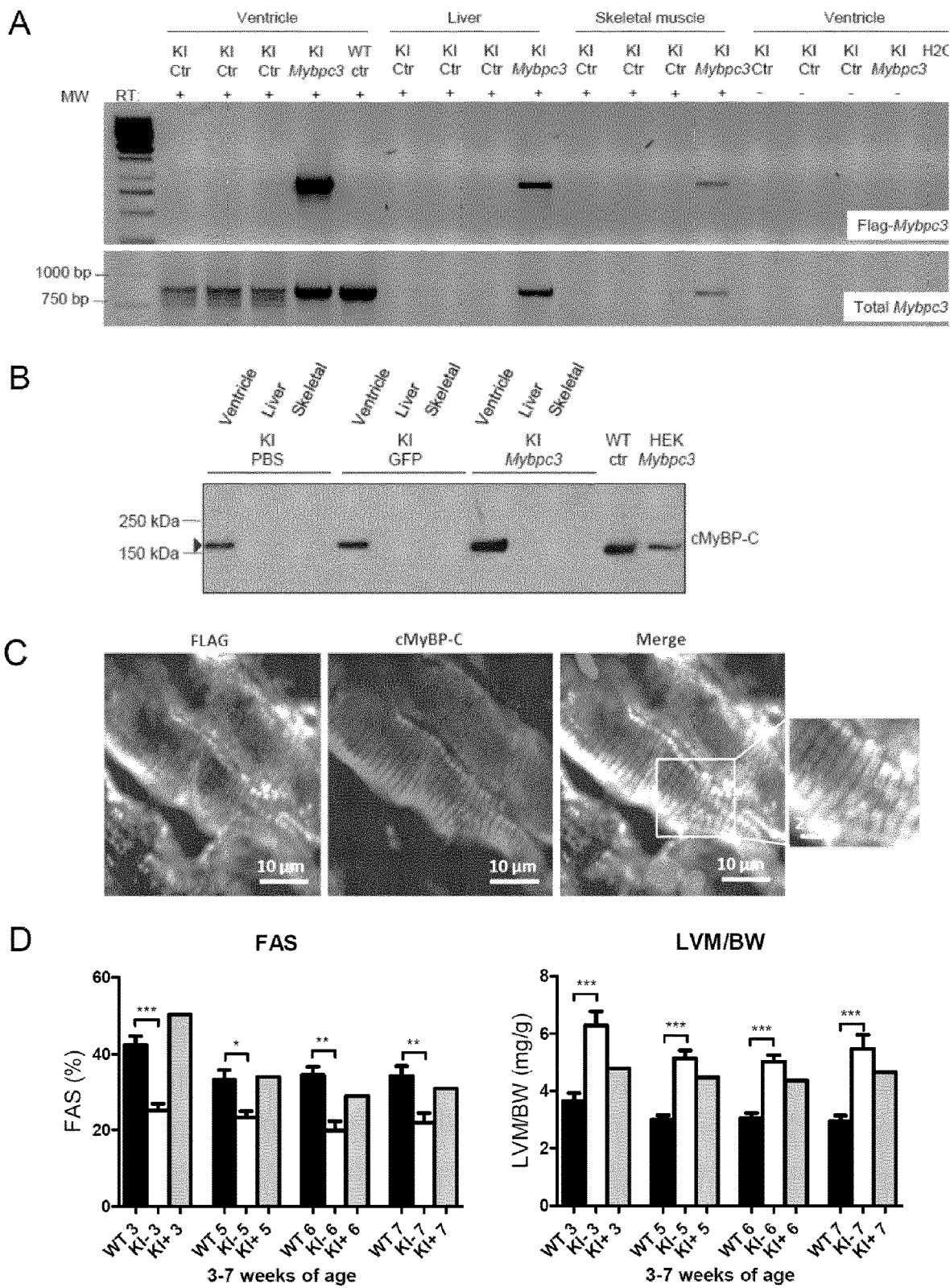
FIG. 5: AAV9-mediated FLAG-Mybpc3 gene transfer in neonatal Mybpc3-targeted knock-in mouse. (A) RT-PCR of FLAG-tagged and total Mybpc3 mRNAs were evaluated by RT-PCR in ventricles, liver and skeletal muscle. Ctr: PBS administration. (B) cMyBP-C protein determination in Western blot of proteins extracted from ventricles, liver and skeletal muscle. (C) Immunofluorescence analysis of myocardial sections of AAV9-FLAG-Mybpc3-transduced KI mouse. AAV9-FLAG-Mybpc3 was administered into the temporal vein of 1-day-old KI mice for 7 weeks. Cryosections (10-μm thickness) were stained with antibodies directed against FLAG and cMyBP-C. The merge picture, including its higher magnification is shown on the right panel. Immunofluorescence analysis was performed by confocal microscopy with a 40x-oil objective. Scale bars are indicated. (D) Fractional area shortening (FAS) and left ventricular mass-to-body weight (LVM/BW) ratio were determined by echocardiography in wild-type (WT), PBS-treated knock-in (KI−) and KI injected with AAV9-FLAG-Mybpc3 (KI+). Evaluations were performed at 3, 5, 6 and 7 weeks of age. Data are expressed as mean±SEM. *P<0.05, P<0.01 and *P<0.001 vs. WT mice.

The level of FLAG-Mybpc3 mRNA was much higher in the ventricles than in other organs (FIG. 5A, upper FLAG-Mybpc3 panel). In the ventricles, the different mutant Mybpc3 mRNAs were amplified in the control KI mice (FIG. 5A, lower total Mybpc3 panel), whereas a major unique band was detected in wild-type control mouse and in the KI mouse transduced with AAV9-FLAG-Mybpc3 (FIG. 5A, total Mybpc3 panel). A band was also detected in liver and skeletal muscle after FLAG-Mybpc3 gene transfer, although at a lower level than in the ventricles.

Western blot analyses was performed as described in Example 3 using an antibody directed against cMyBP-C and revealed that the cMyBP-C protein level after AAV9-FLAG-Mybpc3 gene transfer is higher than in PBS- or AAV9-GFP-injected KI mice and reached the level found in WT mouse (FIG. 5B). cMyBP-C protein was not detected in the liver and skeletal muscle after Mybpc3 gene transfer (FIG. 5B), due to the cardiac-specificity of the vector.

In order to examine the localization of the exogenously expressed FLAG-tagged cMyBP-C protein, immunofluorescence analysis was performed on ventricular cryosections of the KI mouse injected with AAV9-FLAG-Mybpc3 for 7 weeks using antibodies directed against FLAG epitope and total cMyBP-C protein. The staining showed the classic striation pattern of the cMyBP-C protein located in doublets in the A-band of the sarcomere (FIG. 5C; cMyBP-C), which entirely co-stained with the FLAG signal (FIG. 5C; FLAG). Nuclei were stained with DRAQ5™. Taken together, the overexpressed cMyBP-C protein was properly incorporated within the sarcomere and the majority of FLAG-positive-striated cardiomyocytes were co-stained with total cMyBP-C protein, suggesting that exogenous cMyBP-C protein replaced the endogenous mutant ones.

Echocardiographic analyses were performed as described in Example 1 above. Fractional area shortening (FAS) and left ventricular mass-to-body weight (LVM/BW) ratio were examined in wild-type (WT), PBS-injected knock-in (KI−) mice and KI mice injected with AAV9-FLAG-Mybpc3 (KI+) at 3, 5, 6 and 7 weeks of age. Evaluation of the cardiac function by echocardiography showed a rescue of the fractional area shortening (FAS) and a reduction of the left ventricular mass-to-body weight (LVM/BW) ratio after FLAG-Mybpc3 gene transfer (FIG. 5D).

Together, these data showed that a single administration of AAV9-FLAG-Mybpc3 in neonatal KI mice rescues the molecular phenotype (no cMyBP-C haploinsufficiency and no mutant polypeptides) and the functional phenotype (no left ventricular hypertrophy and dysfunction).

Example 6

Expression of Exogenous Wild-type Myc-MYBPC3 in Human Cardiac Myocytes Derived from Induced-pluripotent Stem Cells Induced pluripotent stem cells (iPSC) were generated by reprogramming of fibroblasts expanded from a skin biopsy of a human control individual. Cardiac myocyte differentiation was adapted from a protocol from the group of Gordon Keller (Yang L et al., 2008, Nature 22:524-8).

After differentiation, human cardiac myocytes were plated at a density of $2\times10^5$ cells/well in a 12-well plate for RNA and protein analysis, or $2.5\times10^4$ cells/chamber in a four chamber dish (35-mm diameter) for immunofluorescence analysis. Cardiac myocytes were transduced for 8 days with a myc-tagged MYBPC3 adenovirus encoding human myc-cMyBP-C (DNA sequence: SEQ ID NO:29 followed by SEQ ID NO:1) at different MOI.

Construction of the myc-tagged human MYBPC3 plasmid was described previously (Flavigny J et al., 1999, J Mol Biol 294, 443-456; Sarikas et al., 2005, Cardiovasc Res 66:33-44). Briefly, an ATG plus 30-nucleotide sequence (SEQ ID NO:29) encoding the myc epitope (SEQ ID NO:30) was inserted behind the CMV promoter (SEQ ID NO:31) and before the human MYBPC3 cDNA (SEQ ID NO:1). The insert encodes a myc-tagged human cMyBP-C (SEQ ID NO:32). Recombinant adenovirus were generated by cloning the insert (myc-tagged human MYBPC3 cDNA) into the shuttle vector pAdTrack-CMV and subsequent cotransformation of this plasmid with pAdEasy-1 into *Escherichia coli* as described previously (He T et al., 1998 Proc Natl Acad Sci U S A 95, 2509-2514). Expression of cMyBP-C is driven by the constitutively active CMV promoter (SEQ ID NO:31).

Figure 6:
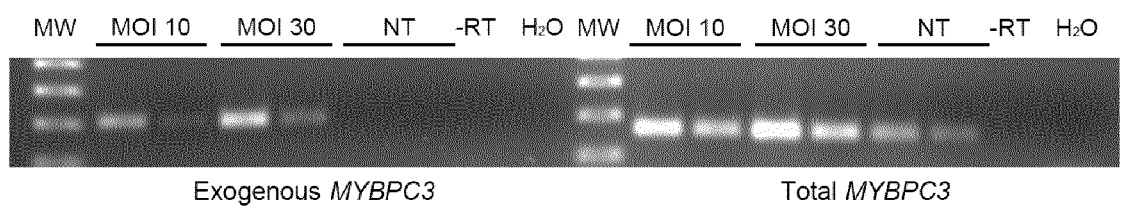
FIG. 6: Expression of exogenous human myc-MYBPC3 in human cardiac myocytes. Human cardiac myocytes were derived from human induced-pluripotent stem cells (iPSC) and transduced with adenovirus (MOI of 10 or 30) encoding myc-tagged human MYBPC3. (A) RT-PCR of exogenous myc-MYBPC3 in iPSC-derived human cardiac myocytes. Exogenous MYBPC3 mRNA was amplified with specific primers; total MYBPC3 mRNA amplified with primers that recognized both exogenous and endogenous MYBPC3. (B) Exogenous myc-cMyBP-C protein levels in human cardiac myocytes derived from iPSC. Western blot analysis was performed using antibody directed either the myc tag sequence (=exogenous myc-cMyBP-C) or against the CO-C1 domains of cMyBP-C (=total cMyBP-C). Positive control (+) corresponds to a sample of murine cardiac myocytes transduced with the same adenovirus. (C) Localization of exogenous human myc-cMyBP-C in human cardiac myocytes derived from iPSC, analysed by immunofluorescence; cMyBP-C: anti-cMyBP-C antibody; myc: anti-myc antibody, i.e. exogenous cMyBP-C. Scale bars are indicated in the figure. Abbreviations: NT, not transduced; MOI, multiplicity of infection; –RT, no reverse transcriptase.
Figure 6:
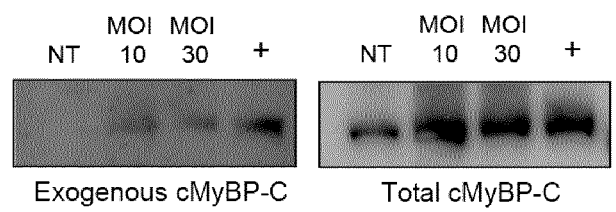
Figure 6:
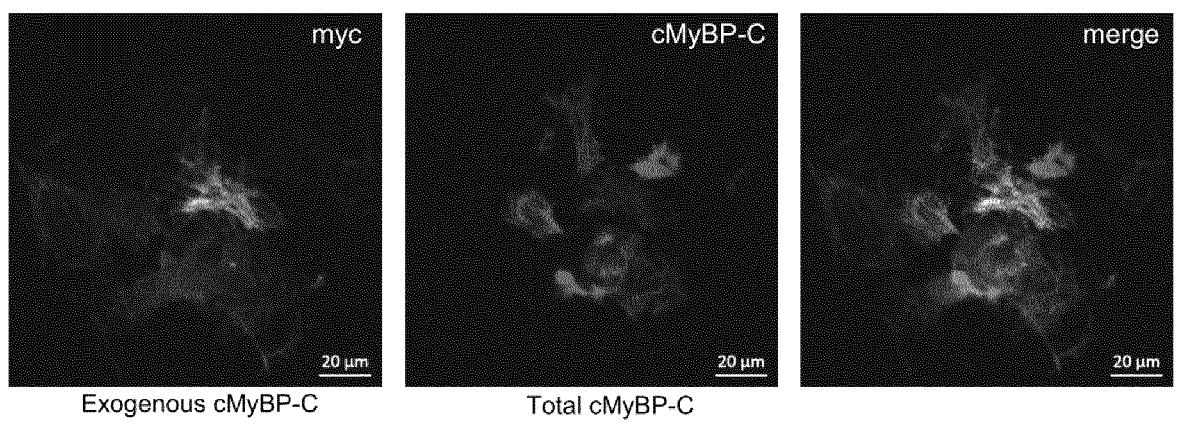

The evaluation of the transcription of the different MYBPC3 mRNAs (exogenous myc-MYBPC3 and total MYBPC3) in human cardiac myocytes was performed by RT-PCR as described before (FIG. 6A). Exogenous MYBPC3 mRNA was amplified with specific primers (Forward primer in the myc sequence, 5'-GCA AAA GCT TAT TAG CGA GGA A-3' (SEQ ID NO:33) and reverse primer in exon 2, 5'-CAG GCC GTA CTT GTT GCT G-3' (SEQ ID NO:34)), and total MYBPC3 mRNA with primers that recognized both exogenous and endogenous MYBPC3 (Forward primer in exon 1, 5'-GGG GAA GAA GCC AGT CTC AG-3' (SEQ ID NO:35) and reverse primer in exon 2, 5'-CAG GCC GTA CTT GTT GCT G-3' (SEQ ID NO:34)). The level of Myc-MYBPC3 mRNA increased with increasing virus dose (FIG. 6A, left panel). No Myc-MYBPC3 mRNA was detected in non-transduced cells (NT) and in negative controls lacking reverse transcriptase (−RT).

Western blot analysis was performed as described before using antibodies directed either against the C0-C1 domains of cMyBP-C (FIG. 6B, total cMyBP-C, kindly given by collaborator) or against the myc tag (FIG. 6B, exogenous myc-cMyBP-C (rabbit polyclonal Sigma; catalog # C3956). The positive control (+) was a sample of murine cardiac myocytes transduced with the same virus. The level of total cMyBP-C was slightly increased after adenoviral gene transfer, whereas the myc-tagged cMyBP-C protein was absent in non-transduced (NT) sample and its level increased with increasing MOI (FIG. 6B).

Localization of exogenous myc-cMyBP-C in human cardiac myocytes derived from iPSC was analysed by immunofluorescence. Human cardiac myocytes were stained with anti-cMyBP-C antibody (FIG. 6C, cMyBP-C), which showed expected sarcomeric striations. Exogenous cMyBP-C was stained with the anti-myc antibody (FIG. 6C, myc). The anti-myc antibody binds to the myc tag, which is located at the N-terminus of the protein. It was observed that exogenous myc-tagged cMyBP-C was correctly incorporated into the sarcomere of human iPSC-derived cardiac myocytes as a doublet in the A band.

These data showed for the first time expression of exogenous human myc-MYBPC3 in human cardiac myocytes derived from iPSC. Expression of exogenous human myc-MYBPC3 resulted in a stable human cMyBP-C protein, which is incorporated into the sarcomere. Thus, overexpression of MYBPC3 cDNA may be used for gene therapy in human hypertrophic cardiomyopathy.

Example 7

Long-term Mybpc3 Gene Therapy Restored Mybpc3 mRNA Level and Partially Prevented Cardiac Hypertrophy and Dysfunction in Mybpc3-targeted Knock-in Mice Different doses of adeno-associated virus serotype 9 (AAV9)-Mybpc3 ($1 \times 10^{11}$, $3 \times 10^{11}$, $1 \times 10^{12}$ and $3 \times 10^{12}$ vector genomes (vg)/mouse) or PBS were administered into the temporal vein of 1-day-old Mybpc3-targeted knock-in (KI) mice, before the appearance of the cardiac disease phenotype. After 34 weeks, mice were subjected to in vivo hemodynamics and tissue analysis. WT mice were used as controls.

Analyses of systolic (=dP/dtmax) and diastolic (=dP/dtmin) function and determination of the heart weight to body weight ratio (HW/BW) were performed in 34-week-old WT, KI treated with PBS and KI mice treated with the highest dose of $3 \times 10^{12}$ vg (FIG. 7.1 A). Compared to WT, the slight reduction in systolic function, the marked reduction in diastolic function and the marked increase in HW/BW ratio were prevented by Mybpc3 gene therapy in KI mice.

Further, RT-PCR was performed for evaluation of the mRNA levels of exogenous FLAG-tagged Mybpc3 (FIG. 7.1 B, upper panel) and total Mybpc3 (lower panel). RNA was extracted from ventricular tissues and pooled in each group (n=5-10/group). The size of the PCR-amplified bands is shown on the left side of FIG. 7.1 B. This shows that the expression of Mybpc3 (both exogenous alone and total) increased in a AAV9-Mybpc3 dose-dependent manner. Importantly and conversely, the expression of mutant mRNAs (as represented by the amplicons for mutant-1, mutant-2 and mutant-3) decreased in a AAV9-Mybpc3 dose-dependent manner.

Moreover, total Mybpc3 mRNA level was determined by RT-qPCR performed in 34-week-old WT, KI treated with PBS and KI mice treated with the highest dose of $3 \times 10^{12}$ vg (FIG. 7.1 C). Compared to WT, the marked reduction in Mybpc3 mRNA level was fully prevented by Mybpc3 gene therapy in KI mice.

Western blot analysis was performed for evaluation of the protein levels of exogenous FLAG-tagged cMyBP-C (FIG. 7.2 D, upper panels) and total cMyBP-C (lower panels). Ventricular protein extracts from each group were pooled for the analysis. Blots were stained with antibodies directed against the FLAG epitope or total cMyBP-C (upper part in each condition). An antibody directed against GAPDH was used as loading control (lower parts in each condition). As for the Mybpc3 mRNA, this shows that the protein level of cMyBP-C (both exogenous alone and total) increased in a AAV9-Mybpc3 dose-dependent manner.

cMyBP-C protein level was quantified, normalized to GAPDH and related to WT (FIG. 7.2 E). Compared to WT, the marked reduction in cMyBP-C protein level was significantly prevented by Mybpc3 gene therapy in KI mice.

Taken together, these data showed that long-term Mybpc3 gene therapy not only restored the level of Mybpc3 WT in KI mice but also prevented the transcription of mutant Mybpc3 mRNAs. Both partially significantly prevented the development of left ventricular hypertrophy and diastolic dysfunction, which are the key features of hypertrophic cardiomyopathy.

The invention claimed is:

1. A method of treating hypertrophic cardiomyopathy in a human subject, said method comprising:
   administering to said subject, by intravenous injection or infusion or by direct administration to the heart, a gene therapy vector for expressing an exogenous nucleic acid sequence comprising:
   (a) a nucleic acid sequence encoding a functional cardiac sarcomeric protein, wherein said cardiac sarcomeric protein is cardiac myosin binding protein C (cMyBP-C), and
   (b) a cardiomyocyte-specific promoter which is operably linked to said nucleic acid sequence,
   wherein said gene therapy vector is an adeno-associated virus vector, wherein said subject carries a mutation in a gene encoding said cardiac sarcomeric protein which expresses a level of non-functional mutant versions of said protein and causes said hypertrophic cardiomyopathy, and wherein after said administering, said exogenous nucleic acid sequence expresses said functional cardiac sarcomeric protein in the subject and the level of non-functional mutant versions of said protein is reduced in the subject.

2. The method of claim 1, wherein said cardiomyocyte-specific promoter is the human cardiac troponin T promoter (hTNNT2).

3. The method of claim 2, wherein the hTNNT2 promoter comprises the sequence of SEQ ID NO:5.

4. The method of claim 1, wherein said cMyBP-C protein comprises the sequence of SEQ ID NO:2.

5. The method of claim 1, wherein said vector is formulated for administration into the myocardium by intravenous or intracardiac injection or infusion.

* * * * *

SEQUENCE LISTING

```
<160> NUMBER OF SEQ ID NOS: 35

<210> SEQ ID NO 1
<211> LENGTH: 4200
<212> TYPE: DNA
<213> ORGANISM: Homo sapiens

<400> SEQUENCE: 1
catggtgagt gcctggtgtg acgtctctca ggatgcctga gccggggaag aagccagtct      60
cagcctttag caagaagcca cggtcagtgg aagtggccgc aggcagccct gccgtgttcg     120
aggccgagac agagcgggca ggagtgaagg tgcgctggca gcgcggaggc agtgacatca     180
gcgccagcaa caagtacggc ctggccacag agggcacacg gcatacgctg acagtgcggg     240
aagtgggccc tgccgaccag ggatcttacg cagtcattgc tggctcctcc aaggtcaagt     300
tcgacctcaa ggtcatagag gcagagaagg cagagcccat gctggcccct gcccctgccc     360
ctgctgaggc cactggagcc cctggagaag ccccggcccc agccgctgag ctgggagaaa     420
gtgccccaag tcccaaaggg tcaagctcag cagctctcaa tggtcctacc cctggagccc     480
ccgatgaccc cattggcctc ttcgtgatgc ggccacagga tggcgaggtg accgtgggtg     540
gcagcatcac cttctcagcc cgcgtggccg gcgccagcct cctgaagccg cctgtggtca     600
```

```
agtggttcaa gggcaaatgg gtggacctga gcagcaaggt gggccagcac ctgcagctgc      660
acgacagcta cgaccgcgcc agcaaggtct atctgttcga gctgcacatc accgatgccc      720
agcctgcctt cactggcagc taccgctgtg aggtgtccac caaggacaaa tttgaatgct      780
ccaacttcaa tctcactgtc cacgaggcca tgggcaccgg agacctggac ctcctatcag      840
ccttccgccg cacgagcctg gctggaggtg gtcggcggat cagtgatagc catgaggaca      900
ctgggattct ggacttcagc tcactgctga aaagagaga cagtttccgg accccgaggg      960
actcgaagct ggaggcacca gcagaggagg acgtgtggga gatcctacgg caggcacccc     1020
catctgagta cgacgcatc gccttccagt acggcgtcac tgacctgcgc ggcatgctaa      1080
agaggctcaa gggcatgagg cgcgatgaga agaagagcac agcctttcag aagaagctgg     1140
agccggccta ccaggtgagc aaaggccaca agatccggct gaccgtggaa ctggctgacc     1200
atgacgctga ggtcaaatgg ctcaagaatg ccaggagat ccagatgagc ggcagcaagt      1260
acatctttga gtccatcggt gccaagcgta ccctgaccat cagccagtgc tcattggcgg     1320
acgacgcagc ctaccagtgc gtggtgggtg gcgagaagtg tagcacggag ctctttgtga     1380
aagagccccc tgtgctcatc acgcgccct tggaggacca gctggtgatg gtggggcagc      1440
gggtggagtt tgagtgtgaa gtatcggagg aggggcgca agtcaaatgg ctgaaggacg      1500
gggtggagct gacccgggag gagaccttca ataccggtt caagaaggac gggcagagac     1560
accacctgat catcaacgag gccatgctgg aggacgcggg gcactatgca ctgtgcacta     1620
gcgggggcca ggcgctgcgt gagctcattg tgcaggaaaa gaagctggag gtgtaccaga     1680
gcatcgcaga cctgatggtg ggcgcaaagg accaggcggt gttcaaatgt gaggtctcag     1740
atgagaatgt tcggggtgtg tggctgaaga atgggaagga gctggtgccc gacagccgca     1800
taaaggtgtc ccacatcggg cgggtccaca aactgaccat tgacgacgtc acacctgccg     1860
acgaggctga ctacagcttt gtgcccgagg gcttcgcctg caacctgtca gccaagctcc     1920
acttcatgga ggtcaagatt gacttcgtac ccaggcagga acctcccaag atccacctgg     1980
actgcccagg ccgcatacca gacaccattg tggttgtagc tggaaataag ctacgtctgg     2040
acgtccctat ctctggggac cctgctccca ctgtgatctg gcagaaggct atcacgcagg     2100
ggaataaggc cccagccagg ccagcccag atgccccaga ggacacaggt gacagcgatg      2160
agtgggtgtt tgacaagaag ctgctgtgtg agaccgaggg ccgggtccgc gtggagacca     2220
ccaaggaccg cagcatcttc acggtcgagg gggcagagaa ggaagatgag ggcgtctaca     2280
cggtcacagt gaagaaccct gtgggcgagg accaggtcaa cctcacagtc aaggtcatcg     2340
acgtgccaga cgcacctgcg gcccccaaga tcagcaacgt gggagaggac tcctgcacag     2400
tacagtggga gccgcctgcc tacgatgcg ggcagcccat cctgggctac atcctggagc      2460
gcaagaagaa gaagagctac cggtggatgc agctgaactt cgacctgatt caggagctga     2520
gtcatgaagc gcgcgcatg atcgagggcg tggtgtacga gatgcgcgtc tacgcggtca     2580
acgccatcgg catgtccagg cccagccctg cctccagcc cttcatgcct atcggtcccc      2640
ccagcgaacc cacccacctg gcagtagagg acgtctctga caccacggtc tccctcaagt     2700
ggcggccccc agagcgcgtg ggagcaggag gcctggatgg ctacagcgtg gagtactgcc     2760
cagagggctg ctcagagtgg gtggctgccc tgcaggggct gacagagcac acatcgatac     2820
tggtgaagga cctgcccacg ggggcccggc tgcttttccg agtgcgggca cacaatatgg     2880
cagggcctgg agcccctgtt accaccacgg agccggtgac agtgcaggag atcctgcaac     2940
```

```
ggccacggct tcagctgccc aggcacctgc gccagaccat tcagaagaag gtcggggagc    3000
ctgtgaacct tctcatccct ttccagggca gccccggcc tcaggtgacc tggaccaaag     3060
aggggcagcc cctggcaggc gaggaggtga gcatccgcaa cagccccaca gacaccatcc    3120
tgttcatccg ggccgctcgc cgcgtgcatt caggcactta ccaggtgacg gtgcgcattg    3180
agaacatgga ggacaaggcc acgctggtgc tgcaggttgt tgacaagcca agtcctcccc    3240
aggatctccg ggtgactgac gcctggggtc ttaatgtggc tctggagtgg aagccacccc    3300
aggatgtcgg caacacggaa ctctgggggt acacagtgca gaaagccgac aagaagacca    3360
tggagtggtt caccgtcttg gagcattacc gccgcaccca ctgcgtggtg ccagagctca    3420
tcattggcaa tggctactac ttccgcgtct tcagccagaa tatggttggc tttagtgaca    3480
gagcggccac caccaaggag cccgtcttta tccccagacc aggcatcacc tatgagccac    3540
ccaactataa ggccctggac ttctccgagg ccccaagctt cacccagccc ctggtgaacc    3600
gctcggtcat cgcgggctac actgctatgc tctgctgtgc tgtccggggt agccccaagc    3660
ccaagatttc ctggttcaag aatggcctgg acctgggaga agacgcccgc ttccgcatgt    3720
tcagcaagca gggagtgttg actctggaga ttagaaagcc ctgcccctt gacggggca     3780 tctatgtctg cagggccacc aacttacagg gcgaggcacg tgtgagtgc cgcctggagg     3840 tgcgagtgcc tcagtgacca ggctggctcc tggggatggc caggtacaac cggatgccag    3900
ccccgtgcca ggagcctgga gggaagttgg ggaaaccct ccctactgtt ggatgtatgt     3960
gtgacaagtg tgtctcctgt gctgcgatgg gggatcagca gggcagttgt cgggcagtcc    4020
tgagtgggtg ttgcacagac tggtccacag ggctcctgaa ggaagcccct ggatctttgg    4080
ggtaaaagga gggtggcctc aagaaacaat gtctggggac aggcctttct ggcctgctat    4140
gtcttcccaa tgtttattgg gcaataaaag ataagtgcag tcacagagaa ctcactcttc    4200

<210> SEQ ID NO 2
<211> LENGTH: 1274
<212> TYPE: PRT
<213> ORGANISM: Homo sapiens

<400> SEQUENCE: 2

Met Pro Glu Pro Gly Lys Lys Pro Val Ser Ala Phe Ser Lys Lys Pro
1               5                   10                  15

Arg Ser Val Glu Val Ala Ala Gly Ser Pro Ala Val Phe Glu Ala Glu
            20                  25                  30

Thr Glu Arg Ala Gly Val Lys Val Arg Trp Gln Arg Gly Gly Ser Asp
        35                  40                  45

Ile Ser Ala Ser Asn Lys Tyr Gly Leu Ala Thr Glu Gly Thr Arg His
    50                  55                  60

Thr Leu Thr Val Arg Glu Val Gly Pro Ala Asp Gln Gly Ser Tyr Ala
65                  70                  75                  80

Val Ile Ala Gly Ser Ser Lys Val Lys Phe Asp Leu Lys Val Ile Glu
                85                  90                  95

Ala Glu Lys Ala Glu Pro Met Leu Ala Pro Ala Pro Ala Pro Ala Glu
            100                 105                 110

Ala Thr Gly Ala Pro Gly Glu Ala Pro Ala Ala Glu Leu Gly
        115                 120                 125

Glu Ser Ala Pro Ser Pro Lys Gly Ser Ser Ala Ala Leu Asn Gly
    130                 135                 140

Pro Thr Pro Gly Ala Pro Asp Asp Pro Ile Gly Leu Phe Val Met Arg
145                 150                 155                 160
```

```
Pro Gln Asp Gly Glu Val Thr Val Gly Gly Ser Ile Thr Phe Ser Ala
            165                 170                 175

Arg Val Ala Gly Ala Ser Leu Leu Lys Pro Pro Val Val Lys Trp Phe
        180                 185                 190

Lys Gly Lys Trp Val Asp Leu Ser Ser Lys Val Gly Gln His Leu Gln
    195                 200                 205

Leu His Asp Ser Tyr Asp Arg Ala Ser Lys Val Tyr Leu Phe Glu Leu
210                 215                 220

His Ile Thr Asp Ala Gln Pro Ala Phe Thr Gly Ser Tyr Arg Cys Glu
225                 230                 235                 240

Val Ser Thr Lys Asp Lys Phe Asp Cys Ser Asn Phe Asn Leu Thr Val
            245                 250                 255

His Glu Ala Met Gly Thr Gly Asp Leu Asp Leu Leu Ser Ala Phe Arg
        260                 265                 270

Arg Thr Ser Leu Ala Gly Gly Arg Arg Ile Ser Asp Ser His Glu
    275                 280                 285

Asp Thr Gly Ile Leu Asp Phe Ser Ser Leu Leu Lys Lys Arg Asp Ser
    290                 295                 300

Phe Arg Thr Pro Arg Asp Ser Lys Leu Glu Ala Pro Ala Glu Glu Asp
305                 310                 315                 320

Val Trp Glu Ile Leu Arg Gln Ala Pro Pro Ser Glu Tyr Glu Arg Ile
            325                 330                 335

Ala Phe Gln Tyr Gly Val Thr Asp Leu Arg Gly Met Leu Lys Arg Leu
        340                 345                 350

Lys Gly Met Arg Arg Asp Glu Lys Lys Ser Thr Ala Phe Gln Lys Lys
    355                 360                 365

Leu Glu Pro Ala Tyr Gln Val Ser Lys Gly His Lys Ile Arg Leu Thr
    370                 375                 380

Val Glu Leu Ala Asp His Asp Ala Glu Val Lys Trp Leu Lys Asn Gly
385                 390                 395                 400

Gln Glu Ile Gln Met Ser Gly Ser Lys Tyr Ile Phe Glu Ser Ile Gly
            405                 410                 415

Ala Lys Arg Thr Leu Thr Ile Ser Gln Cys Ser Leu Ala Asp Asp Ala
        420                 425                 430

Ala Tyr Gln Cys Val Val Gly Gly Glu Lys Cys Ser Thr Glu Leu Phe
    435                 440                 445

Val Lys Glu Pro Pro Val Leu Ile Thr Arg Pro Leu Glu Asp Gln Leu
    450                 455                 460

Val Met Val Gly Gln Arg Val Glu Phe Glu Cys Glu Val Ser Glu Glu
465                 470                 475                 480

Gly Ala Gln Val Lys Trp Leu Lys Asp Gly Val Glu Leu Thr Arg Glu
            485                 490                 495

Glu Thr Phe Lys Tyr Arg Phe Lys Lys Asp Gly Gln Arg His His Leu
        500                 505                 510

Ile Ile Asn Glu Ala Met Leu Glu Asp Ala Gly His Tyr Ala Leu Cys
    515                 520                 525

Thr Ser Gly Gly Gln Ala Leu Ala Glu Leu Ile Val Gln Glu Lys Lys
    530                 535                 540

Leu Glu Val Tyr Gln Ser Ile Ala Asp Leu Met Val Gly Ala Lys Asp
545                 550                 555                 560

Gln Ala Val Phe Lys Cys Glu Val Ser Asp Glu Asn Val Arg Gly Val
            565                 570                 575
```

-continued

```
Trp Leu Lys Asn Gly Lys Glu Leu Val Pro Asp Ser Arg Ile Lys Val
            580                 585                 590
Ser His Ile Gly Arg Val His Lys Leu Thr Ile Asp Asp Val Thr Pro
        595                 600                 605
Ala Asp Glu Ala Asp Tyr Ser Phe Val Pro Glu Gly Phe Ala Cys Asn
    610                 615                 620
Leu Ser Ala Lys Leu His Phe Met Glu Val Lys Ile Asp Phe Val Pro
625                 630                 635                 640
Arg Gln Glu Pro Pro Lys Ile His Leu Asp Cys Pro Gly Arg Ile Pro
                645                 650                 655
Asp Thr Ile Val Val Ala Gly Asn Lys Leu Arg Leu Asp Val Pro
            660                 665                 670
Ile Ser Gly Asp Pro Ala Pro Thr Val Ile Trp Gln Lys Ala Ile Thr
        675                 680                 685
Gln Gly Asn Lys Ala Pro Ala Arg Pro Ala Pro Asp Ala Pro Glu Asp
    690                 695                 700
Thr Gly Asp Ser Asp Glu Trp Val Phe Asp Lys Lys Leu Leu Cys Glu
705                 710                 715                 720
Thr Glu Gly Arg Val Arg Val Glu Thr Thr Lys Asp Arg Ser Ile Phe
                725                 730                 735
Thr Val Glu Gly Ala Glu Lys Glu Asp Glu Gly Val Tyr Thr Val Thr
            740                 745                 750
Val Lys Asn Pro Val Gly Glu Asp Gln Val Asn Leu Thr Val Lys Val
        755                 760                 765
Ile Asp Val Pro Asp Ala Pro Ala Ala Pro Lys Ile Ser Asn Val Gly
    770                 775                 780
Glu Asp Ser Cys Thr Val Gln Trp Glu Pro Pro Ala Tyr Asp Gly Gly
785                 790                 795                 800
Gln Pro Ile Leu Gly Tyr Ile Leu Glu Arg Lys Lys Lys Ser Tyr
                805                 810                 815
Arg Trp Met Arg Leu Asn Phe Asp Leu Ile Gln Glu Leu Ser His Glu
            820                 825                 830
Ala Arg Arg Met Ile Glu Gly Val Val Tyr Glu Met Arg Val Tyr Ala
        835                 840                 845
Val Asn Ala Ile Gly Met Ser Arg Pro Ser Pro Ala Ser Gln Pro Phe
    850                 855                 860
Met Pro Ile Gly Pro Pro Ser Glu Pro Thr His Leu Ala Val Glu Asp
865                 870                 875                 880
Val Ser Asp Thr Thr Val Ser Leu Lys Trp Arg Pro Pro Glu Arg Val
                885                 890                 895
Gly Ala Gly Gly Leu Asp Gly Tyr Ser Val Glu Tyr Cys Pro Glu Gly
            900                 905                 910
Cys Ser Glu Trp Val Ala Ala Leu Gln Gly Leu Thr Glu His Thr Ser
        915                 920                 925
Ile Leu Val Lys Asp Leu Pro Thr Gly Ala Arg Leu Leu Phe Arg Val
    930                 935                 940
Arg Ala His Asn Met Ala Gly Pro Gly Ala Pro Val Thr Thr Thr Glu
945                 950                 955                 960
Pro Val Thr Val Gln Glu Ile Leu Gln Arg Pro Arg Leu Gln Leu Pro
                965                 970                 975
Arg His Leu Arg Gln Thr Ile Gln Lys Lys Val Gly Glu Pro Val Asn
            980                 985                 990
Leu Leu Ile Pro Phe Gln Gly Lys  Pro Arg Pro Gln Val  Thr Trp Thr
```

```
             995                1000               1005
Lys  Glu  Gly  Gln  Pro  Leu  Ala  Gly  Glu  Glu  Val  Ser  Ile  Arg  Asn
     1010                1015               1020

Ser  Pro  Thr  Asp  Thr  Ile  Leu  Phe  Ile  Arg  Ala  Ala  Arg  Arg  Val
     1025               1030                1035

His  Ser  Gly  Thr  Tyr  Gln  Val  Thr  Val  Arg  Ile  Glu  Asn  Met  Glu
     1040               1045                1050

Asp  Lys  Ala  Thr  Leu  Val  Leu  Gln  Val  Val  Asp  Lys  Pro  Ser  Pro
     1055               1060                1065

Pro  Gln  Asp  Leu  Arg  Val  Thr  Asp  Ala  Trp  Gly  Leu  Asn  Val  Ala
     1070               1075                1080

Leu  Glu  Trp  Lys  Pro  Pro  Gln  Asp  Val  Gly  Asn  Thr  Glu  Leu  Trp
     1085               1090                1095

Gly  Tyr  Thr  Val  Gln  Lys  Ala  Asp  Lys  Lys  Thr  Met  Glu  Trp  Phe
     1100               1105                1110

Thr  Val  Leu  Glu  His  Tyr  Arg  Arg  Thr  His  Cys  Val  Val  Pro  Glu
     1115               1120                1125

Leu  Ile  Ile  Gly  Asn  Gly  Tyr  Tyr  Phe  Arg  Val  Phe  Ser  Gln  Asn
     1130               1135                1140

Met  Val  Gly  Phe  Ser  Asp  Arg  Ala  Ala  Thr  Thr  Lys  Glu  Pro  Val
     1145               1150                1155

Phe  Ile  Pro  Arg  Pro  Gly  Ile  Thr  Tyr  Glu  Pro  Pro  Asn  Tyr  Lys
     1160               1165                1170

Ala  Leu  Asp  Phe  Ser  Glu  Ala  Pro  Ser  Phe  Thr  Gln  Pro  Leu  Val
     1175               1180                1185

Asn  Arg  Ser  Val  Ile  Ala  Gly  Tyr  Thr  Ala  Met  Leu  Cys  Cys  Ala
     1190               1195                1200

Val  Arg  Gly  Ser  Pro  Lys  Pro  Lys  Ile  Ser  Trp  Phe  Lys  Asn  Gly
     1205               1210                1215

Leu  Asp  Leu  Gly  Glu  Asp  Ala  Arg  Phe  Arg  Met  Phe  Ser  Lys  Gln
     1220               1225                1230

Gly  Val  Leu  Thr  Leu  Glu  Ile  Arg  Lys  Pro  Cys  Pro  Phe  Asp  Gly
     1235               1240                1245

Gly  Ile  Tyr  Val  Cys  Arg  Ala  Thr  Asn  Leu  Gln  Gly  Glu  Ala  Arg
     1250               1255                1260

Cys  Glu  Cys  Arg  Leu  Glu  Val  Arg  Val  Pro  Gln
     1265               1270
```

<210> SEQ ID NO 3
<211> LENGTH: 4163
<212> TYPE: DNA
<213> ORGANISM: Mus musculus

<400> SEQUENCE: 3

```
agtccctcct tgggtggcct gcttgatgcc tggtgtgact gttctcaaga tgccggagcc    60
agggaagaaa ccagtgtcag ccttcaacaa gaagccaagg tcagcggagg tgaccgctgg   120
cagtgctgcc gtgttcgagg ctgagacgga gcggtcaggc gtgaaggtgc ggtggcagcg   180
ggatggcagc gacatcaccg ccaatgacaa gtatggtttg gcagcagagg gcaagcgaca   240
cacactgaca gtgcgggatg cgagccctga tgaccagggt tcctacgcgg tcattgcagg   300
ctccctcaaag gtcaagtttg acctcaaggt cacagagcca gcccctccag agaaggcaga   360
atctgaagtt gctccaggag cccccaaaga agtccctgct ccagccactg agttggaaga   420
aagtgtctca gtcctgaagg gtcagtctc ggtaacccag gatggctcag ctgcagagca   480
```

```
tcagggagcc cctgatgacc ctattggcct ctttctgatg cgaccacagg atggtgaggt      540
gaccgtgggc ggcagcattg tcttctcagc ccgagtggct ggggccagcc tcctgaaacc      600
gcctgtggtc aagtggttca agggcaagtg ggtggacctg agcagcaaag tgggccagca      660
cctgcagctg catgacagct atgacagagc cagcaaggtc tacttgtttg agttgcacat      720
cacagatgct cagaccactt ctgctggggg ctaccgctgt gaggtgtcta ccaaggacaa      780
atttgacagc tgtaacttca acctcactgt ccatgaggcc attggttctg agacctgga      840 cctcagatca gctttccgac gcacgagcct ggcgggagca ggtcggagaa ccagtgacag      900
ccatgaagat gctgggactc tggactttag ttccctgctg aagaagagag acagtttccg      960
gagggactca agctggagg cacctgctga agaagacgtg tgggagatcc tgagacaggc     1020
accgccgtca gaatatgagc gcatcgcctt ccagcacgga gtcacagacc ttcgaggcat     1080
gctgaagagg ctcaagggca tgaagcagga tgaaaagaag agcacagcct tcagaagaa      1140 gctggagcct gcctaccagg taaacaaggg ccacaagatt cggcttactg tggaactggc     1200
tgatccggac gccgaagtca gtggcttaa gaatggacag agatccaga tgagtggcag      1260 caagtacatc ttcgagtccg tcggtgccaa gcgcaccctg accatcagcc agtgctcact     1320
ggctgacgac gcagcctacc agtgtgtggt ggggggcgag aagtgcagca cggagctctt     1380
tgtcaaagag cccccggtgc tgatcactcg gtccctggaa gaccagctgg tgatggtggg     1440
tcagcgggtg gagtttgagt gtgaggtctc agaagaaggg gcccaagtca aatggctgaa     1500
ggatggggtt gagctgacac gtgaggagac cttcaaatac cggttcaaga agatgggcg      1560 gaaacaccac ttgatcatca atgaagcaac cctggaggat gcaggacact atgcagtacg     1620
cacaagtgga ggccagtcac tggctgagct cattgtgcaa gagaagaagt tggaggtata     1680
ccaaagcatc gcggacctgg cagtgggagc caaggaccag gctgtgttta agtgtgaggt     1740
ttcagatgag aatgtacgcg gcgtgtggct gaagaatggg aaggaactgg tgcctgacaa     1800
ccgcataaag gtgtcccata taggccgggt ccacaaactg accattgacg atgtcacacc     1860
tgctgatgag gctgactaca gctttgtccc tgaagggttt gcctgcaacc tgtctgccaa     1920
gctccacttc atggaggtca agattgactt tgtgcctagg caggaacctc ccaagatcca     1980
cttggattgt cccggcagca caccagacac cattgtggtt gttgctggga acaagttacg     2040 cctgatgtc cctatttctg gagaccctgc tcccactgtg gtctggcaga agactgtaac     2100 acagggaag aaggcctcaa ctgggccaca ccctgatgcc ccagaagatg ctggtgctga     2160
tgaggagtgg gtgtttgata agaagctgtt gtgtgagact gagggccggg tccgggtgga     2220
gaccaccaaa gaccgcagcg tctttacagt cgaagggca gagaaggaag atgaaggtgt      2280
ctacacagtc acagtaaaga accccgtggg cgaggaccag gtcaacctca cagtcaaggt     2340
catcgatgtc ccagatgctc ctgcggcccc taagatcagc aacgtgggcg aggactcctg     2400
cactgtgcag tgggaaccgc ctgcctatga tggcgggcag ccggtcctgg atacatcct      2460 ggagcgcaag aagaaaaaga gctacaggtg gatgaggctc aactttgatc tgctgcggga     2520
gctgagccac gaggcgaggc gcatgatcga gggtgtagcc tatgagatgc gagtctacgc     2580
agtcaatgcc gtgggaatgt ccaggcccag ccctgcctct cagcccttca tgcctattgg     2640
gccccctggc gaaccaaccc acttggctgt ggaggatgtg tcagacacca ctgtctcact     2700
caagtggcgg cccccagagc gcgtgggggc cggtggcctg acggatacag cgtggagta     2760 ctgccaggag ggatgctccg agtggacacc tgctctgcag gggctgacag agcgcacatc     2820
```

```
gatgctggtg aaggacctac ccactggggc acggctgctg ttccgagtac gggcacacaa    2880
tgtggcaggt cctggaggcc ctatcgtcac caaggagcct gtgacagtgc aggagatact    2940
gcaacgacca cggctccaac tgcccagaca cctgcgccag accatccaga agaaagttgg    3000
ggagcctgtg aacctcctca tcccttccca gggcaaaccc cggcctcagg tgacctggac    3060
caaagagggg cagcccctgg caggtgagga ggtgagcatc cggaacagcc ccacagacac    3120
gatcttgttc atccgagctg cccgccgcac ccactcgggc acctaccagg tgacagttcg    3180
cattgagaac atggaggaca aggcaacgct gatcctgcag attgtggaca agccaagtcc    3240
tccccaggat atccggatcg ttgagacttg gggtttcaat gtggctctgg agtggaagcc    3300
accccaagat gatggcaata cagagatctg gggttatact gtacagaaag ctgacaagaa    3360
gaccatggag tggttcacgg ttttggaaca ctaccgacgc actcactgtg tggtatcaga    3420
gcttatcatt ggcaatggct actacttccg ggtcttcagc cataacatgg tgggttccag    3480
tgacaaagct gccgccacca aggagccagt ctttattcca agaccaggca tcacatatga    3540
gccacccaaa tacaaggccc tggacttctc tgaggcccca agcttcaccc agcccttggc    3600
aaatcgctcc atcattgcag gctataatgc catcctctgc tgtgctgtcc gaggtagtcc    3660
taagcccaag atttcctggt tcaagaatgg cctggatctg ggagaagatg ctcgcttccg    3720
catgttctgc aagcagggag tattgaccct ggagatcagg aaaccctgcc cctatgatgg    3780
tggtgtctat gtctgcaggg ccaccaactt gcagggcgag gcacagtgtg agtgccgcct    3840
ggaggtgcga gttcctcagt gaccaggatg gctccccaga gatggctagg tacaaatgga    3900
tgccaggctg tgtaccagac cggaagggag ttggaggagc cccttttctg ctactgcat    3960 gtgtgtgtgc aactgtgcat cctggaagga ctggccagca gtgacaccag gcaggtctgc    4020
tgggttctga gaaactgac cctaaggata atgttaatac tgggagcata agtgtgtgg    4080 gcttcagaag tggtgactgg ggacaggccc ttttggctgg ctcattgtgt aggagcaata    4140
aaagatctgt gccattcctg ggg                                            4163
```

<210> SEQ ID NO 4
<211> LENGTH: 1278
<212> TYPE: PRT
<213> ORGANISM: Mus musculus

<400> SEQUENCE: 4

```
Met Pro Gly Val Thr Val Leu Lys Met Pro Glu Pro Gly Lys Lys Pro
1               5                   10                  15

Val Ser Ala Phe Asn Lys Lys Pro Arg Ser Ala Glu Val Thr Ala Gly
            20                  25                  30

Ser Ala Ala Val Phe Glu Ala Glu Thr Glu Arg Ser Gly Val Lys Val
        35                  40                  45

Arg Trp Gln Arg Asp Gly Ser Asp Ile Thr Ala Asn Asp Lys Tyr Gly
    50                  55                  60

Leu Ala Ala Glu Gly Lys Arg His Thr Leu Thr Val Arg Asp Ala Ser
65                  70                  75                  80

Pro Asp Asp Gln Gly Ser Tyr Ala Val Ile Ala Gly Ser Ser Lys Val
                85                  90                  95

Lys Phe Asp Leu Lys Val Thr Glu Pro Ala Pro Glu Lys Ala Glu
            100                 105                 110

Ser Glu Val Ala Pro Gly Ala Pro Lys Glu Val Pro Ala Pro Ala Thr
        115                 120                 125

Glu Leu Glu Glu Ser Val Ser Ser Pro Glu Gly Ser Val Ser Val Thr
```

```
            130                 135                 140
Gln Asp Gly Ser Ala Ala Glu His Gln Gly Ala Pro Asp Pro Ile
145                 150                 155                 160

Gly Leu Phe Leu Met Arg Pro Gln Asp Gly Glu Val Thr Val Gly Gly
                165                 170                 175

Ser Ile Val Phe Ser Ala Arg Val Ala Gly Ala Ser Leu Leu Lys Pro
                180                 185                 190

Pro Val Val Lys Trp Phe Lys Gly Lys Trp Val Asp Leu Ser Ser Lys
            195                 200                 205

Val Gly Gln His Leu Gln Leu His Asp Ser Tyr Asp Arg Ala Ser Lys
            210                 215                 220

Val Tyr Leu Phe Glu Leu His Ile Thr Asp Ala Gln Thr Thr Ser Ala
225                 230                 235                 240

Gly Gly Tyr Arg Cys Glu Val Ser Thr Lys Asp Lys Phe Asp Ser Cys
                245                 250                 255

Asn Phe Asn Leu Thr Val His Glu Ala Ile Gly Ser Gly Asp Leu Asp
                260                 265                 270

Leu Arg Ser Ala Phe Arg Arg Thr Ser Leu Ala Gly Ala Gly Arg Arg
            275                 280                 285

Thr Ser Asp Ser His Glu Asp Ala Gly Thr Leu Asp Phe Ser Ser Leu
            290                 295                 300

Leu Lys Lys Arg Asp Ser Phe Arg Arg Asp Ser Lys Leu Glu Ala Pro
305                 310                 315                 320

Ala Glu Glu Asp Val Trp Glu Ile Leu Arg Gln Ala Pro Pro Ser Glu
                325                 330                 335

Tyr Glu Arg Ile Ala Phe Gln His Gly Val Thr Asp Leu Arg Gly Met
                340                 345                 350

Leu Lys Arg Leu Lys Gly Met Lys Gln Asp Glu Lys Lys Ser Thr Ala
            355                 360                 365

Phe Gln Lys Lys Leu Glu Pro Ala Tyr Gln Val Asn Lys Gly His Lys
            370                 375                 380

Ile Arg Leu Thr Val Glu Leu Ala Asp Pro Asp Ala Glu Val Lys Trp
385                 390                 395                 400

Leu Lys Asn Gly Gln Glu Ile Gln Met Ser Gly Ser Lys Tyr Ile Phe
                405                 410                 415

Glu Ser Val Gly Ala Lys Arg Thr Leu Thr Ile Ser Gln Cys Ser Leu
                420                 425                 430

Ala Asp Asp Ala Ala Tyr Gln Cys Val Val Gly Gly Glu Lys Cys Ser
            435                 440                 445

Thr Glu Leu Phe Val Lys Glu Pro Pro Val Leu Ile Thr Arg Ser Leu
            450                 455                 460

Glu Asp Gln Leu Val Met Val Gly Gln Arg Val Glu Phe Glu Cys Glu
465                 470                 475                 480

Val Ser Glu Glu Gly Ala Gln Val Lys Trp Leu Lys Asp Gly Val Glu
                485                 490                 495

Leu Thr Arg Glu Glu Thr Phe Lys Tyr Arg Phe Lys Lys Asp Gly Arg
                500                 505                 510

Lys His His Leu Ile Ile Asn Glu Ala Thr Leu Glu Asp Ala Gly His
            515                 520                 525

Tyr Ala Val Arg Thr Ser Gly Gly Gln Ser Leu Ala Glu Leu Ile Val
            530                 535                 540

Gln Glu Lys Lys Leu Glu Val Tyr Gln Ser Ile Ala Asp Leu Ala Val
545                 550                 555                 560
```

-continued

Gly Ala Lys Asp Gln Ala Val Phe Lys Cys Glu Val Ser Asp Glu Asn
                565                 570                 575

Val Arg Gly Val Trp Leu Lys Asn Gly Lys Glu Leu Val Pro Asp Asn
            580                 585                 590

Arg Ile Lys Val Ser His Ile Gly Arg Val His Lys Leu Thr Ile Asp
        595                 600                 605

Asp Val Thr Pro Ala Asp Glu Ala Asp Tyr Ser Phe Val Pro Glu Gly
    610                 615                 620

Phe Ala Cys Asn Leu Ser Ala Lys Leu His Phe Met Glu Val Lys Ile
625                 630                 635                 640

Asp Phe Val Pro Arg Gln Glu Pro Pro Lys Ile His Leu Asp Cys Pro
                645                 650                 655

Gly Ser Thr Pro Asp Thr Ile Val Val Ala Gly Asn Lys Leu Arg
            660                 665                 670

Leu Asp Val Pro Ile Ser Gly Asp Pro Ala Pro Thr Val Val Trp Gln
        675                 680                 685

Lys Thr Val Thr Gln Gly Lys Lys Ala Ser Thr Gly Pro His Pro Asp
    690                 695                 700

Ala Pro Glu Asp Ala Gly Ala Asp Glu Glu Trp Val Phe Asp Lys Lys
705                 710                 715                 720

Leu Leu Cys Glu Thr Glu Gly Arg Val Arg Val Glu Thr Thr Lys Asp
                725                 730                 735

Arg Ser Val Phe Thr Val Glu Gly Ala Glu Lys Glu Asp Glu Gly Val
            740                 745                 750

Tyr Thr Val Thr Val Lys Asn Pro Val Gly Glu Asp Gln Val Asn Leu
        755                 760                 765

Thr Val Lys Val Ile Asp Val Pro Asp Ala Pro Ala Ala Pro Lys Ile
    770                 775                 780

Ser Asn Val Gly Glu Asp Ser Cys Thr Val Gln Trp Glu Pro Pro Ala
785                 790                 795                 800

Tyr Asp Gly Gly Gln Pro Val Leu Gly Tyr Ile Leu Glu Arg Lys Lys
                805                 810                 815

Lys Lys Ser Tyr Arg Trp Met Arg Leu Asn Phe Asp Leu Leu Arg Glu
            820                 825                 830

Leu Ser His Glu Ala Arg Arg Met Ile Glu Gly Val Ala Tyr Glu Met
        835                 840                 845

Arg Val Tyr Ala Val Asn Ala Val Gly Met Ser Arg Pro Ser Pro Ala
    850                 855                 860

Ser Gln Pro Phe Met Pro Ile Gly Pro Pro Gly Glu Pro Thr His Leu
865                 870                 875                 880

Ala Val Glu Asp Val Ser Asp Thr Thr Val Ser Leu Lys Trp Arg Pro
                885                 890                 895

Pro Glu Arg Val Gly Ala Gly Gly Leu Asp Gly Tyr Ser Val Glu Tyr
            900                 905                 910

Cys Gln Glu Gly Cys Ser Glu Trp Thr Pro Ala Leu Gln Gly Leu Thr
        915                 920                 925

Glu Arg Thr Ser Met Leu Val Lys Asp Leu Pro Thr Gly Ala Arg Leu
    930                 935                 940

Leu Phe Arg Val Arg Ala His Asn Val Ala Gly Pro Gly Pro Ile
945                 950                 955                 960

Val Thr Lys Glu Pro Val Thr Val Gln Glu Ile Leu Gln Arg Pro Arg
                965                 970                 975

Leu Gln Leu Pro Arg His Leu Arg Gln Thr Ile Gln Lys Val Gly
        980                 985                 990

Glu Pro Val Asn Leu Leu Ile Pro Phe Gln Gly Lys Pro Arg Pro Gln
        995                 1000                1005

Val Thr Trp Thr Lys Glu Gly Gln Pro Leu Ala Gly Glu Glu Val
    1010                1015                1020

Ser Ile Arg Asn Ser Pro Thr Asp Thr Ile Leu Phe Ile Arg Ala
    1025                1030                1035

Ala Arg Arg Thr His Ser Gly Thr Tyr Gln Val Thr Val Arg Ile
    1040                1045                1050

Glu Asn Met Glu Asp Lys Ala Thr Leu Ile Leu Gln Ile Val Asp
    1055                1060                1065

Lys Pro Ser Pro Pro Gln Asp Ile Arg Ile Val Glu Thr Trp Gly
    1070                1075                1080

Phe Asn Val Ala Leu Glu Trp Lys Pro Pro Gln Asp Asp Gly Asn
    1085                1090                1095

Thr Glu Ile Trp Gly Tyr Thr Val Gln Lys Ala Asp Lys Lys Thr
    1100                1105                1110

Met Glu Trp Phe Thr Val Leu Glu His Tyr Arg Arg Thr His Cys
    1115                1120                1125

Val Val Ser Glu Leu Ile Ile Gly Asn Gly Tyr Tyr Phe Arg Val
    1130                1135                1140

Phe Ser His Asn Met Val Gly Ser Ser Asp Lys Ala Ala Ala Thr
    1145                1150                1155

Lys Glu Pro Val Phe Ile Pro Arg Pro Gly Ile Thr Tyr Glu Pro
    1160                1165                1170

Pro Lys Tyr Lys Ala Leu Asp Phe Ser Glu Ala Pro Ser Phe Thr
    1175                1180                1185

Gln Pro Leu Ala Asn Arg Ser Ile Ile Ala Gly Tyr Asn Ala Ile
    1190                1195                1200

Leu Cys Cys Ala Val Arg Gly Ser Pro Lys Pro Lys Ile Ser Trp
    1205                1210                1215

Phe Lys Asn Gly Leu Asp Leu Gly Glu Asp Ala Arg Phe Arg Met
    1220                1225                1230

Phe Cys Lys Gln Gly Val Leu Thr Leu Glu Ile Arg Lys Pro Cys
    1235                1240                1245

Pro Tyr Asp Gly Gly Val Tyr Val Cys Arg Ala Thr Asn Leu Gln
    1250                1255                1260

Gly Glu Ala Gln Cys Glu Cys Arg Leu Glu Val Arg Val Pro Gln
    1265                1270                1275

<210> SEQ ID NO 5
<211> LENGTH: 544
<212> TYPE: DNA
<213> ORGANISM: Homo sapiens

<400> SEQUENCE: 5
ctcagtccat taggagccag tagcctggaa gatgtcttta ccccagcat cagttcaagt      60 ggagcagcac ataactcttg ccctctgcct tccaagattc tggtgctgag acttatggag    120
tgtcttggag gttgccttct gcccccaac cctgctccca gctggccctc ccaggcctgg     180
gttgctggcc tctgctttat caggattctc aagagggaca gctggtttat gttgcatgac    240
tgttccctgc atatctgctc tggttttaaa tagcttatct gagcagctgg aggaccacat    300
gggcttatat ggcgtggggt acatgttcct gtagccttgt ccctggcacc tgccaaaata    360

```
gcagccaaca ccccccaccc ccaccgccat cccccctgccc cacccgtccc ctgtcgcaca      420
ttcctccctc cgcagggctg gctcaccagg ccccagccca catgcctgct taaagccctc      480
tccatcctct gcctcaccca gtccccgctg agactgagca gacgcctcca ggatctgtcg      540
gcag                                                                   544
```

<210> SEQ ID NO 6
<211> LENGTH: 222
<212> TYPE: DNA
<213> ORGANISM: Artificial Sequence
<220> FEATURE:
<223> OTHER INFORMATION: polyadenylation signal

<400> SEQUENCE: 6

```
cagacatgat aagatacatt gatgagtttg gacaaaccac aactagaatg cagtgaaaaa       60
aatgctttat ttgtgaaatt tgtgatgcta ttgctttatt tgtaaccatt ataagctgca      120
ataaacaagt taacaacaac aattgcattc attttatgtt tcaggttcag ggggagatgt      180
gggaggtttt ttaaagcaag taaaacctct acaaatgtgg ta                        222
```

<210> SEQ ID NO 7
<211> LENGTH: 133
<212> TYPE: DNA
<213> ORGANISM: Artificial Sequence
<220> FEATURE:
<223> OTHER INFORMATION: chimeric intron

<400> SEQUENCE: 7

```
gtaagtatca aggttacaag acaggtttaa ggagaccaat agaaactggg cttgtcgaga       60
cagagaagac tcttgcgttt ctgataggca cctattggtc ttactgacat ccactttgcc      120
tttctctcca cag                                                         133
```

<210> SEQ ID NO 8
<211> LENGTH: 9026
<212> TYPE: DNA
<213> ORGANISM: Artificial Sequence
<220> FEATURE:
<223> OTHER INFORMATION: vector construct

<400> SEQUENCE: 8

```
ctagaattca cgcgtctcag tccattagga gccagtagcc tggaagatgt ctttaccccc       60
agcatcagtt caagtggagc agcacataac tcttgccctc tgccttccaa gattctggtg      120
ctgagactta tggagtgtct tggaggttgc cttctgcccc caacccctgc tcccagctgg      180
ccctcccagg cctgggttgc tggcctctgc tttatcagga ttctcaagag ggacagctgg      240
tttatgttgc atgactgttc cctgcatatc tgctctggtt ttaaatagct tatctgagca      300
gctggaggac cacatgggct tatatggcgt ggggtacatg ttcctgtagc cttgtccctg      360
gcacctgcca aaatagcagc caacaccccc caccccacc gccatccccc tgccccaccc      420
gtcccctgtc gcacattcct ccctccgcag ggctggctca ccaggcccca gcccacatgc      480
ctgcttaaag ccctctccat cctctgcctc acccagtccc cgctgagact gagcagacgc      540
ctccaggatc tgtcggcaga agctttattg cggtagttta tcacagttaa attgctaacg      600
cagtcagtgc ttctgacaca acagtctcga acttaagctg cagaagttgg tcgtgaggca      660
ctgggcaggt aagtatcaag gttacaagac aggtttaagg agaccaatag aaactgggct      720
tgtcgagaca gagaagactc ttgcgtttct gataggcacc tattggtctt actgacatcc      780
```

```
actttgcctt tctctccaca ggtgtccact cccagttcaa ttacagctct taaggctaga      840
gtacttaata cgactcacta taggctagcc tcgagatgga ttacaaggat gacgacgata      900
agcctggtgt gactgttctc aagatgccgg agccagggaa gaaaccagtg tcagccttca      960
acaagaagcc aaggtcagcg gaggtgaccg ctggcagtgc tgccgtgttc gaggctgaga     1020
cggagcggtc aggcgtgaag gtgcggtggc agcgggatgg cagcgacatc accgccaatg     1080
acaagtatgg tttggcagca gagggcaagc gacacacact gacagtgcgg gatgcgagcc     1140
ctgatgacca gggttcctac gcggtcattg caggctcctc aaaggtcaag tttgacctca     1200
aggtcacaga gccagcccct ccagagaagg cagaatctga agttgctcca ggagccccca     1260
aagaagtccc tgctccagcc actgagttgg aagaaagtgt ctcaagtcct gaaggtcagt     1320
ctcggtaacc caggatggct cagctgcaga gcatcaggga gcccctgatg accctattgg     1380
cctctttctg atgcgaccac aggatggtga ggtgaccgtg ggcggcagca ttgtcttctc     1440
agcccgagtg gctggggcca gcctcctgaa accgcctgtg gtcaagtggt tcaagggcaa     1500
gtgggtggac ctgagcagca aagtgggcca gcacctgcag ctgcatgaca gctatgacag     1560
agccagcaag gtctacttgt ttgagttgca catcacagat gctcagacca cttctgctgg     1620
gggctaccgc tgtgaggtgt ctaccaagga caaatttgac agctgtaact tcaacctcac     1680
tgtccatgag gccattggtt ctggagacct ggacctcaga tcagctttcc gacgcacgag     1740
cctggcggga gcaggtcgga gaaccagtga cagccatgaa gatgctggga ctctggactt     1800
tagttccctg ctgaagaaga gagacagttt ccggagggac tcaaagctgg aggcacctgc     1860
tgaagaagac gtgtgggaga tcctgagaca ggcaccgccg tcagaatatg agcgcatcgc     1920
cttccagcac ggagtcacag accttcgagg catgctgaag aggctcaagg gcatgaagca     1980
ggatgaaaag aagagcacag cctttcagaa gaagctggaa cctgcctacc aggtaaacaa     2040
gggccacaag attcggctta ctgtggaact ggctgatccg gacgccgaag tcaagtggct     2100
taagaatgga caggagatcc agatgagtgg cagcaagtac atcttcgagt ccgtcggtgc     2160
caagcgcacc ctgaccatca gccagtgctc actggctgac gacgcagcct accagtgtgt     2220 ggtgggggc gagaagtgca gcacggagct ctttgtcaaa gagcccccgg tgctgatcac     2280
tcggtccctg gaagaccagc tggtgatggt gggtcagcgg gtggagtttg agtgtgaggt     2340
ctcagaagaa gggcccaag tcaaatggct gaaggatggg gttgagctga cacgtgagga     2400
gaccttcaaa taccggttca gaaagatggg gcggaaacac cacttgatca tcaatgaagc     2460
aaccctggag gatgcaggac actatgcagt acgcacaagt ggaggccagt cactggctga     2520
gctcattgtg caagagaaga gttggaggt ataccaaagc atcgcggacc tggcagtggg     2580
agccaaggac caggctgtgt ttaagtgtga ggtttcagat gagaatgtac gcggcgtgtg     2640
gctgaagaat gggaaggaac tggtgcctga caaccgcata aaggtgtccc atataggccg     2700
ggtccacaaa ctgaccattg acgatgtcac acctgctgat gaggctgact acagcttgt     2760 ccctgaaggg tttgcctgca acctgtctgc caagctccac ttcatggagg tcaagattga     2820
ctttgtgcct aggcaggaac ctcccaagat ccacttggat tgtcccggca gcacaccaga     2880
caccattgtg gttgttgctg gaacaagtt acgcctggat gtccctattt ctggagaccc     2940
tgctcccact gtggtctggc agaagactgt aacacagggg aagaaggcct caactgggcc     3000
acaccctgat gccccagaag atgctggtgc tgatgaggag tgggtgtttg ataagaagct     3060
gttgtgtgag actgagggcc gggtccgggt ggagaccacc aaagaccgca gcgtcttttac     3120 agtcgaaggg gcagagaagg aagatgaagg tgtctacaca gtcacagtaa agaaccccgt     3180
```

```
gggcgaggac caggtcaacc tcacagtcaa ggtcatcgat gtcccagatg ctcctgcggc   3240
ccctaagatc agcaacgtgg gcgaggactc ctgcactgtg cagtgggaac cgcctgccta   3300
tgatggcggg cagccggtcc tgggatacat cctggagcgc aagaagaaaa agagctacag   3360
gtggatgagg ctcaactttg atctgctgcg ggagctgagc cacgaggcga ggcgcatgat   3420
cgagggtgta gcctatgaga tgcgagtcta cgcagtcaat gccgtgggaa tgtccaggcc   3480
cagccctgcc tctcagccct tcatgcctat tgggcccct ggcgaaccaa cccacttggc    3540
tgtggaggat gtgtcagaca ccactgtctc actcaagtgg cggcccccag agcgcgtggg   3600
ggccggtggc ctggacggat acagcgtgga gtactgccag gagggatgct ccagtggac     3660 acctgctctg caggggctga cagagcgcac atcgatgctg gtgaaggacc tacccactgg   3720
ggcacggctg ctgttccgag tacgggcaca caatgtggca ggtcctggag ccctatcgt    3780 caccaaggag cctgtgacag tgcaggagat actgcaacga ccacggctcc aactgcccag   3840
acacctgcgc cagaccatcc agaagaaagt tggggagcct gtgaacctcc tcatcccttt   3900
ccagggcaaa ccccggcctc aggtgacctg gaccaaagag gggcagcccc tggcaggtga   3960
ggaggtgagc atccggaaca gccccacaga cacgatcttg ttcatccgag ctgcccgccg   4020
cacccactcg ggcacctacc aggtgacagt tcgcattgag aacatggagg acaaggcaac   4080
gctgatcctg cagattgtgg acaagccaag tcctccccag gatatccgga tcgttgagac   4140
ttggggtttc aatgtggctc tggagtggaa gccacccca gatgatggca atacagagat    4200
ctggggttat actgtacaga aagctgacaa gaagaccatg gagtggttca cggttttgga   4260
acactaccga cgcactcact gtgtggtatc agagcttatc attggcaatg ctactactt    4320 ccgggtcttc agccataaca tggtgggttc cagtgacaaa gctgccgcca ccaaggagcc   4380
agtctttatt ccaagaccag gcatcacata tgagccaccc aaatacaagg ccctggactt   4440
ctctgaggcc ccaagcttca cccagcccct ggcaaatcgc tccatcattg caggctataa   4500
tgccatcctc tgctgtgctg tccgaggtag tcctaagccc aagatttcct ggttcaagaa   4560
tggcctggat ctgggagaag atgctcgctt ccgcatgttc tgcaagcagg agtattgac    4620 cctggagatc aggaaaccct gccctatga tggtggtgtc tatgtctgca gggccaccaa    4680
cttgcagggc gaggcacagt gtgagtgccg cctggaggtg cgagttcctc agtgaccagg   4740
gatccgtcga cgcggccgct tcccttagt gagggttaat gcttcgagca gacatgataa    4800
gatacattga tgagtttgga caaaccacaa ctagaatgca gtgaaaaaaa tgctttattt   4860
gtgaaatttg tgatgctatt gctttatttg taaccattat aagctgcaat aaacaagtta   4920
acaacaacaa ttgcattcat tttatgtttc aggttcaggg ggagatgtgg gaggtttttt   4980
aaagcaagta aaacctctac aaatgtggta aaatccgata agggactaga gcatggctac   5040
gtagataagt agcatggcgg gttaatcatt aactacaagg aaccctagt gatggagttg    5100 gccactccct ctctgcgcgc tcgctcgctc actgaggccg ggcgaccaa ggtcgcccga    5160 cgcccgggct ttgcccggc ggcctcagtg agcgagcgag cgcgccagct ggcgtaatag    5220
cgaagaggcc cgcaccgatc gcccttccca cagttgcgc agcctgaatg gcgaatggcg    5280
attccagacg attgagcgtc aaaatgtagg tatttccatg agcgttttc cgttgcaatg    5340 gctggcggta atattgttct ggatattacc agcaaggccg atagtttgag ttcttctact   5400
caggcaagtg atgttattac taatcaaaga agtattgcga caacggttaa tttgcgtgat   5460
ggacagactc ttttactcgg tggcctcact gattataaaa acacttctca ggattctggc   5520
```

```
gtaccgttcc tgtctaaaat ccctttaatc ggcctcctgt ttagctcccg ctctgattct    5580
aacgaggaaa gcacgttata cgtgctcgtc aaagcaacca tagtacgcgc cctgtagcgg    5640
cgcattaagc gcggcgggtg tggtggttac gcgcagcgtg accgctacac ttgccagcgc    5700
cctagcgccc gctcctttcg ctttcttccc ttcctttctc gccacgttcg ccggctttcc    5760
ccgtcaagct ctaaatcggg ggctcccttt agggttccga tttagtgctt tacggcacct    5820
cgaccccaaa aaacttgatt agggtgatgg ttcacgtagt gggccatcgc cctgatagac    5880 ggttttcgc cctttgacgt tggagtccac gttctttaat agtggactct tgttccaaac    5940
tggaacaaca ctcaacccta tctcggtcta ttcttttgat ttataaggga ttttgccgat    6000
ttcggcctat tggttaaaaa atgagctgat ttaacaaaaa tttaacgcga attttaacaa    6060
aatattaacg tctacaattt aaatatttgc ttatacaatc ttcctgtttt tggggctttt    6120
ctgattatca accggggtac atatgattga catgctagtt ttacgattac cgttcatcga    6180
ttctcttgtt tgctccagac tctcaggcaa tgacctgata gcctttgtag agacctctca    6240
aaaatagcta ccctctccgg catgaattta tcagctagaa cggttgaata tcatattgat    6300
ggtgatttga ctgtctccgg cctttctcac ccgtttgaat ctttacctac acattactca    6360
ggcattgcat ttaaaatata tgagggtct aaaaattttt atccttgcgt tgaaataaag    6420
gcttctcccg caaaagtatt acagggtcat aatgtttttg gtacaaccga tttagcttta    6480
tgctctgagg ctttattgct taattttgct aattctttgc cttgcctgta tgatttattg    6540
gatgttggaa tcgcctgatg cggtattttc tccttacgca tctgtgcggt atttcacacc    6600
gcatatggtg cactctcagt acaatctgct ctgatgccgc atagttaagc cagccccgac    6660
acccgccaac acccgctgac gcgccctgac gggcttgtct gctcccggca tccgcttaca    6720
gacaagctgt gaccgtctcc gggagctgca tgtgtcagag gttttcaccg tcatcaccga    6780
aacgcgcgag acgaaagggc ctcgtgatac gcctatttt ataggttaat gtcatgataa    6840
taatggtttc ttagacgtca ggtggcactt ttcggggaaa tgtgcgcgga accectattt    6900 gtttatttt ctaaatacat tcaaatatgt atccgctcat gagacaataa ccctgataaa    6960
tgcttcaata atattgaaaa aggaagagta tgagtattca aatttccgt gtcgccctta    7020 ttccctttt tgcggcattt tgccttcctg ttttgctca cccagaaacg ctggtgaaag    7080
taaaagatgc tgaagatcag ttgggtgcac gagtgggtta catcgaactg gatctcaaca    7140
gcggtaagat ccttgagagt tttcgccccg aagaacgttt tccaatgatg agcacttta    7200 aagttctgct atgtggcgcg gtattatccc gtattgacgc cgggcaagag caactcggtc    7260
gccgcataca ctattctcag aatgacttgg ttgagtactc accagtcaca gaaaagcatc    7320
ttacggatgg catgacagta agagaattat gcagtgctgc cataaccatg agtgataaca    7380
ctgcggccaa cttacttctg acaacgatcg gaggaccgaa ggagctaacc gcttttttgc    7440
acaacatggg ggatcatgta actcgcettg atcgttggga accggagctg aatgaagcca    7500
taccaaacga cgagcgtgac accacgatgc ctgtagcaat ggcaacaacg ttgcgcaaac    7560
tattaactgg cgaactactt actctagctt cccggcaaca attaatagac tggatggagg    7620
cggataaagt tgcaggacca cttctgcgct cggcccttcc ggctggctgg tttattgctg    7680
ataaatctgg agccggtgag cgtgggtctc gcggtatcat tgcagcactg gggccagatg    7740
gtaagccctc ccgtatcgta gttatctaca cgacggggag tcaggcaact atggatgaac    7800
gaaatagaca gatcgctgag ataggtgcct cactgattaa gcattggtaa ctgtcagacc    7860
aagtttactc atatatactt tagattgatt taaaacttca tttttaattt aaaaggatct    7920
```

-continued

```
aggtgaagat ccttttgat aatctcatga ccaaaatccc ttaacgtgag ttttcgttcc    7980
actgagcgtc agacccgta gaaaagatca aaggatcttc ttgagatcct ttttttctgc    8040
gcgtaatctg ctgcttgcaa acaaaaaaac caccgctacc agcggtggtt tgtttgccgg    8100
atcaagagct accaactctt tttccgaagg taactggctt cagcagagcg cagataccaa    8160
atactgtcct tctagtgtag ccgtagttag gccaccactt caagaactct gtagcaccgc    8220
ctacatacct cgctctgcta atcctgttac cagtggctgc tgccagtggc gataagtcgt    8280
gtcttaccgg gttggactca agacgatagt taccggataa ggcgcagcgg tcgggctgaa    8340
cggggggttc gtgcacacag cccagcttgg agcgaacgac ctacaccgaa ctgagatacc    8400
tacagcgtga gctatgagaa agcgccacgc ttcccgaagg gagaaaggcg gacaggtatc    8460
cggtaagcgg cagggtcgga acaggagagc gcacgaggga gcttccaggg ggaaacgcct    8520
ggtatcttta tagtcctgtc gggtttcgcc acctctgact tgagcgtcga ttttgtgat    8580 gctcgtcagg gggcggagc ctatggaaaa acgccagcaa cgcggccttt ttacggttcc    8640
tggccttttg ctggcctttt gctcacatgt tctttcctgc gttatcccct gattctgtgg    8700
ataaccgtat taccgccttt gagtgagctg ataccgctcg ccgcagccga acgaccgagc    8760
gcagcgagtc agtgagcgag gaagcggaag agcgcccaat acgcaaaccg cctctccccg    8820
cgcgttggcc gattcattaa tgcagcagct gcgcgctcgc tcgctcactg aggccgcccg    8880
ggcaaagccc gggcgtcggg cgacctttgg tcgcccggcc tcagtgagcg agcgagcgcg    8940
cagagaggga gtggccaact ccatcactag gggttccttg tagttaatga ttaacccgcc    9000
atgctactta tctacgtagc catgct                                          9026
```

<210> SEQ ID NO 9
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 9

```
ggattacaag gatgacgacg a                                                21
```

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10

```
tccagagtcc cagcatcttc                                                  20
```

<210> SEQ ID NO 11
<211> LENGTH: 59
<212> TYPE: DNA
<213> ORGANISM: Artificial Sequence
<220> FEATURE:
<223> OTHER INFORMATION: oligonucleotide primer

<400> SEQUENCE: 11

```
ttcgacctcg agatggatta caaggatgac gacgataagc ctggtgtgac tgttctcaa      59
```

<210> SEQ ID NO 12
<211> LENGTH: 30
<212> TYPE: DNA

<213> ORGANISM: Artificial Sequence
<220> FEATURE:
<223> OTHER INFORMATION: oligonucleotide primer

<400> SEQUENCE: 12
ttcgacggat ccctggtcac tgaggaactc                            30

<210> SEQ ID NO 13
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 13
aaaaaaacgc gtctcagtcc attaggagcc agtagc                     36

<210> SEQ ID NO 14
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 14 ccccccaag cttctgccga cagatcctgg aggcg                       35

<210> SEQ ID NO 15
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 15
ctcagtccat taggagccag t                                     21

<210> SEQ ID NO 16
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 16
aaggcaacct ccaagacact                                       20

<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 17
ggattacaag gatgacgacg a                                     21

<210> SEQ ID NO 18
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 18
tccagagtcc cagcatcttc                                       20

```
<210> SEQ ID NO 19
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 19
cctggtgtga ctgttctcaa                                              20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 20
tccagagtcc cagcatcttc                                              20

<210> SEQ ID NO 21
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 21
ctcaagctca tggctacact cttctc                                       26

<210> SEQ ID NO 22
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 22
agagcagaca ctgtttggaa gga                                          23

<210> SEQ ID NO 23
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 23
gatgcgagcc ctgatgac                                                18

<210> SEQ ID NO 24
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 24
gacttgagac actttcttcc                                              20

<210> SEQ ID NO 25
<211> LENGTH: 16
<212> TYPE: DNA
<213> ORGANISM: Artificial Sequence
<220> FEATURE:
```

```
<223> OTHER INFORMATION: oligonuleotide probe

<400> SEQUENCE: 25
ctcactgtcc ataagg                                                       16

<210> SEQ ID NO 26
<211> LENGTH: 14
<212> TYPE: DNA
<213> ORGANISM: Artificial Sequence
<220> FEATURE:
<223> OTHER INFORMATION: oligonuleotide probe

<400> SEQUENCE: 26
ccagcaagag gcca                                                         14

<210> SEQ ID NO 27
<211> LENGTH: 25
<212> TYPE: DNA
<213> ORGANISM: Artificial Sequence
<220> FEATURE:
<223> OTHER INFORMATION: oligonuleotide probe

<400> SEQUENCE: 27
tcggagaacc agcccctgct agctc                                             25

<210> SEQ ID NO 28
<211> LENGTH: 3895
<212> TYPE: DNA
<213> ORGANISM: homo sapiens

<400> SEQUENCE: 28
atgcctgagc cggggaagaa gccagtctca gcttttagca agaagccacg gtcagtggaa        60
gtggccgcag gcagccctgc cgtgttcgag gccgagacag agcgggcagg agtgaaggtg       120
cgctggcagc gcggaggcag tgacatcagc gccagcaaca agtacggcct ggccacagag       180
ggcacacggc atacgctgac agtgcgggaa gtgggccctg ccgaccaggg atcttacgca       240
gtcattgctg gctcctccaa ggtcaagttc gacctcaagg tcatagaggc agagaaggca       300
gagcccatgc tggcccctgc ccctgcccct gctgaggcca ctggagcccc tggagaagcc       360
ccggccccag ccgctgagct gggagaaagt gccccaagtc ccaaagggtc aagctcagca       420
gctctcaatg gtcctacccc tgagccccca tgatgacccca ttggcctctt cgtgatgcgg       480
ccacaggatg gcgaggtgac cgtggaggcc atgggcaccg agacctgga cctcctatca       540 gccttccgcc gcacgagcct ggctggaggt ggtcggcgga tcagtgatag ccatgaggac       600
actgggattc tggacttcag ctcactgctg aaaaagagag acagtttccg gaccccgagg       660
gactcgaagc tggaggcacc agcagaggag gacgtgtggg agatcctacg gcaggcaccc       720
ccatctgagt acgagcgcat cgccttccag tacggcgtca ctgacctgcg cggcatgcta       780
aagaggctca agggcatgag gcgcgatgag aagaagagca cagcctttca gaagaagctg       840
gagccggcct accaggtgag caaaggccac aagatccggc tgaccgtgga actggctgac       900
catgacgctg aggtcaaatg gctcaagaat ggccaggaga tccagatgag cggcagcaag       960
tacatctttg agtccatcgg tgccaagcgt accctgacca tcagccagtg ctcattggcg      1020
gacgacgcag cctaccagtg cgtggtgggt ggcgagaagt gtagcacgga gctctttgtg      1080
aaagagcccc ctgtgctcat cacgcgcccc ttggaggacc agctggtgat ggtggggcag      1140
cgggtggagt ttgagtgtga agtatcggag gaggggcgc aagtcaaatg gctgaaggac      1200
ggggtggagc tgacccggga ggagaccttc aaataccggt tcaagaagga cgggcagaga      1260
```

```
caccacctga tcatcaacga ggccatgctg gaggacgcgg ggcactatgc actgtgcact    1320
agcgggggcc aggcgctggc tgagctcatt gtgcaggaaa agaagctgga ggtgtaccag    1380
agcatcgcag acctgatggt gggcgcaaag gaccaggcgg tgttcaaatg tgaggtctca    1440
gatgagaatg ttcggggtgt gtggctgaag aatgggaagg agctggtgcc cgacagccgc    1500
ataaaggtgt cccacatcgg gcgggtccac aaactgacca ttgacgacgt cacacctgcc    1560
gacgaggctg actacagctt tgtgcccgag ggcttcgcct gcaacctgtc agccaagctc    1620
cacttcatgg aggtcaagat tgacttcgta cccaggcagg aacctcccaa gatccacctg    1680
gactgcccag gccgcatacc agacaccatt gtggttgtag ctggaaataa gctacgtctg    1740
gacgtcccta tctctgggga ccctgctccc actgtgatct ggcagaaggc tatcacgcag    1800
gggaataagg ccccagccag gccagcccca gatgccccag aggacacagg tgacagcgat    1860
gagtgggtgt ttgacaagaa gctgctgtgt gagaccgagg gccgggtccg cgtggagacc    1920
accaaggacc gcagcatctt cacggtcgag ggggcagaga aggaagatga gggcgtctac    1980
acggtcacag tgaagaaccc tgtgggcgag gaccaggtca acctcacagt caaggtcatc    2040
gacgtgccag acgcacctgc ggcccccaag atcagcaacg tgggagagga ctcctgcaca    2100
gtacagtggg agccgcctgc ctacgatggc gggcagccca tcctgggcta catcctggag    2160
cgcaagaaga gaagagcta ccggtggatg cggctgaact tcgacctgat tcaggagctg    2220
agtcatgaag cgcggcgcat gatcgagggc gtggtgtacg agatgcgcgt ctacgcggtc    2280
aacgccatcg gcatgtccag gcccagccct gcctcccagc ccttcatgcc tatcggtccc    2340
cccagcgaac ccacccacct ggcagtagag gacgtctctg acaccacggt ctccctcaag    2400
tggcggcccc cagagcgcgt gggagcagga ggcctggatg ctacagcgt ggagtactgc    2460 ccagagggct gctcagagtg ggtggctgcc ctgcaggggc tgacagagca cacatcgata    2520
ctggtgaagg acctgcccac gggggcccgg ctgcttttcc gagtgcgggc acacaatatg    2580
gcagggcctg gagcccctgt taccaccacg gagccggtga cagtgcagga gatcctgcaa    2640
cggccacggc ttcagctgcc caggcaccty cgccagacca ttcagaagaa ggtcggggag    2700
cctgtgaacc ttctcatccc tttccagggc aagccccggc tcaggtgac ctggaccaaa    2760 gaggggcagc cctggcagg cgaggaggtg agcatccgca acagccccac agacaccatc    2820
ctgttcatcc gggccgctcg ccgcgtgcat tcaggcactt accaggtgac ggtgcgcatt    2880
gagaacatgg aggacaaggc cacgctggtg ctgcaggttg ttgacaagcc aagtcctccc    2940
caggatctcc gggtgactga cgcctggggt cttaatgtgg ctctggagtg gcaagccaccc    3000 caggatgtcg gcaacacgga gctctggggg tacacagtgc agaaagccga caagaagacc    3060
atggagtggt tcaccgtctt ggagcattac cgccgcaccc actgcgtggt gcagagctc    3120 atcattggca atggctacta cttccgcgtc ttcagccaga atatggttgg ctttagtgac    3180
agagcggcca ccaccaagga gcccgtcttt atccccagac caggcatcac ctatgagcca    3240
cccaactata aggccctgga cttctccgag gccccaagct tcacccagcc cctggtgaac    3300
cgctcggtca tcgcgggcta cactgctatg ctctgctgtg ctgtccgggg tagccccaag    3360
cccaagattt cctggttcaa gaatggcctg gacctggag aagacgcccg cttccgcatg    3420
ttcagcaagc agggagtgtt gactctggag attagaaagc cctgcccctt tgacggggc    3480 atctatgtct gcagggccac caacttacag ggcgaggcac ggtgtgagtg ccgcctggag    3540
gtgcgagtgc ctcagtgacc aggctggctc ctggggatgg ccaggtacaa ccggatgcca    3600
```

```
gccccgtgcc aggagcctgg agggaagttg gggaaacccc tccctactgt tggatgtatg    3660
tgtgacaagt gtgtctcctg tgctgcgatg ggggatcagc agggcagttg tcgggcagtc    3720
ctgagtgggt gttgcacaga ctggtccaca gggctcctga aggaagcccc tggatctttg    3780
gggtaaaagg agggtggcct caagaaacaa tgtctgggga caggcctttc tggcctgcta    3840
tgtcttccca atgtttattg ggcaataaaa gataagtgca gtcacagaga actca         3895
```

<210> SEQ ID NO 29
<211> LENGTH: 30
<212> TYPE: DNA
<213> ORGANISM: artificial
<220> FEATURE:
<223> OTHER INFORMATION: DNA sequence encoding Myc

<400> SEQUENCE: 29

```
gagcaaaagc ttattagcga ggaagatctg                                      30
```

<210> SEQ ID NO 30
<211> LENGTH: 10
<212> TYPE: PRT
<213> ORGANISM: artificial
<220> FEATURE:
<223> OTHER INFORMATION: Myc-tag protein sequence

<400> SEQUENCE: 30

Glu Gln Lys Leu Ile Ser Glu Glu Asp Leu
1               5                   10

<210> SEQ ID NO 31
<211> LENGTH: 576
<212> TYPE: DNA
<213> ORGANISM: Human cytomegalovirus

<400> SEQUENCE: 31

```
tagtaatcaa ttacggggtc attagttcat agcccatata tggagttccg cgttacataa     60
cttacggtaa atggcccgcc tggctgaccg cccaacgacc cccgcccatt gacgtcaata    120
atgacgtatg ttcccatagt aacgccaata gggactttcc attgacgtca atgggtggag    180
tatttacggt aaactgccca cttggcagta catcaagtgt atcatatgcc aagtacgccc    240
cctattgacg tcaatgacgg taaatggccc gcctggcatt atgcccagta catgacctta    300
tgggactttc ctacttggca gtacatctac gtattagtca tcgctattac catggtgatg    360
cggttttggc agtacatcaa tgggcgtgga tagcggtttg actcacgggg atttccaagt    420
ctccacccca ttgacgtcaa tgggagtttg ttttggcacc aaaatcaacg ggactttcca    480
aaatgtcgta acaactccgc cccattgacg caaatgggcg gtaggcgtgt acggtgggag    540
gtctatataa gcagagctgg tttagtgaac cgtcag                               576
```

<210> SEQ ID NO 32
<211> LENGTH: 1285
<212> TYPE: PRT
<213> ORGANISM: artificial
<220> FEATURE:
<223> OTHER INFORMATION: Myc-tagged human cMyBP-C protein

<400> SEQUENCE: 32

Met Glu Gln Lys Leu Ile Ser Glu Glu Asp Leu Asn Ser Pro Glu Pro
1               5                   10                  15

Gly Lys Lys Pro Val Ser Ala Phe Ser Lys Lys Pro Arg Ser Val Glu
            20                  25                  30

-continued

```
Val Ala Ala Gly Ser Pro Ala Val Phe Glu Ala Glu Thr Glu Arg Ala
         35                  40                  45

Gly Val Lys Val Arg Trp Gln Arg Gly Gly Ser Asp Ile Ser Ala Ser
 50                  55                  60

Asn Lys Tyr Gly Leu Ala Thr Glu Gly Thr Arg His Thr Leu Thr Val
 65                  70                  75                  80

Arg Glu Val Gly Pro Ala Asp Gln Gly Ser Tyr Ala Val Ile Ala Gly
                 85                  90                  95

Ser Ser Lys Val Lys Phe Asp Leu Lys Val Ile Glu Ala Glu Lys Ala
             100                 105                 110

Glu Pro Met Leu Ala Pro Ala Pro Ala Glu Ala Thr Gly Ala
         115                 120                 125

Pro Gly Glu Ala Pro Ala Pro Ala Ala Glu Leu Gly Glu Ser Ala Pro
 130                 135                 140

Ser Pro Lys Gly Ser Ser Ala Ala Leu Asn Gly Pro Thr Pro Gly
 145                 150                 155                 160

Ala Pro Asp Asp Pro Ile Gly Leu Phe Val Met Arg Pro Gln Asp Gly
                 165                 170                 175

Glu Val Thr Val Gly Gly Ser Ile Thr Phe Ser Ala Arg Val Ala Gly
             180                 185                 190

Ala Ser Leu Leu Lys Pro Pro Val Val Lys Trp Phe Lys Gly Lys Trp
         195                 200                 205

Val Asp Leu Ser Ser Lys Val Gly Gln His Leu Gln Leu His Asp Ser
 210                 215                 220

Tyr Asp Arg Ala Ser Lys Val Tyr Leu Phe Glu Leu His Ile Thr Asp
 225                 230                 235                 240

Ala Gln Pro Ala Phe Thr Gly Ser Tyr Arg Cys Glu Val Ser Thr Lys
                 245                 250                 255

Asp Lys Phe Asp Cys Ser Asn Phe Asn Leu Thr Val His Glu Ala Met
             260                 265                 270

Gly Thr Gly Asp Leu Asp Leu Leu Ser Ala Phe Arg Arg Thr Ser Leu
         275                 280                 285

Ala Gly Gly Gly Arg Arg Ile Ser Asp Ser His Glu Asp Thr Gly Ile
 290                 295                 300

Leu Asp Phe Ser Ser Leu Leu Lys Lys Ser Ser Ser Phe Arg Thr Pro
 305                 310                 315                 320

Arg Asp Ser Lys Leu Glu Ala Pro Ala Glu Glu Asp Val Trp Glu Ile
                 325                 330                 335

Leu Arg Gln Ala Pro Pro Ser Glu Tyr Glu Arg Ile Ala Phe Gln Tyr
             340                 345                 350

Gly Val Thr Asp Leu Arg Gly Met Leu Lys Arg Leu Lys Gly Met Arg
         355                 360                 365

Arg Asp Glu Lys Lys Ser Thr Ala Phe Gln Lys Lys Leu Glu Pro Ala
 370                 375                 380

Tyr Gln Val Ser Lys Gly His Lys Ile Arg Leu Thr Val Glu Leu Ala
 385                 390                 395                 400

Asp His Asp Ala Glu Val Lys Trp Leu Lys Asn Gly Gln Glu Ile Gln
                 405                 410                 415

Met Ser Gly Arg Tyr Ile Phe Glu Ser Ile Gly Ala Lys Arg Thr Leu
             420                 425                 430

Thr Ile Ser Gln Cys Ser Leu Ala Asp Asp Ala Ala Tyr Gln Cys Val
         435                 440                 445

Val Gly Gly Glu Lys Cys Ser Thr Glu Leu Phe Val Lys Glu Pro Pro
```

```
                450                 455                 460
Val Leu Ile Thr Arg Pro Leu Glu Asp Gln Leu Val Met Val Gly Gln
465                 470                 475                 480

Arg Val Glu Phe Glu Cys Glu Val Ser Glu Glu Gly Ala Gln Val Lys
                485                 490                 495

Trp Leu Lys Asp Gly Val Glu Leu Thr Arg Glu Thr Phe Lys Tyr
                500                 505                 510

Arg Phe Lys Lys Asp Gly Gln Arg His His Leu Ile Ile Asn Glu Ala
                515                 520                 525

Met Leu Glu Asp Ala Gly His Tyr Ala Leu Cys Thr Ser Gly Gly Gln
530                 535                 540

Ala Leu Ala Glu Leu Ile Val Gln Glu Lys Lys Leu Glu Val Tyr Gln
545                 550                 555                 560

Ser Ile Ala Asp Leu Met Val Gly Ala Lys Asp Gln Ala Val Phe Lys
                565                 570                 575

Cys Glu Val Ser Asp Glu Asn Val Arg Gly Val Trp Leu Lys Asn Gly
                580                 585                 590

Lys Glu Leu Val Pro Asp Ser Arg Ile Lys Val Ser His Ile Gly Arg
                595                 600                 605

Val His Lys Leu Thr Ile Asp Asp Val Thr Pro Ala Asp Glu Ala Asp
                610                 615                 620

Tyr Ser Phe Val Pro Glu Gly Phe Ala Cys Asn Leu Ser Ala Lys Leu
625                 630                 635                 640

His Phe Met Glu Val Lys Ile Asp Phe Val Pro Arg Gln Glu Pro Pro
                645                 650                 655

Lys Ile His Leu Asp Cys Pro Gly Arg Ile Pro Asp Thr Ile Val Val
                660                 665                 670

Val Ala Gly Asn Lys Leu Arg Leu Asp Val Pro Ile Ser Gly Asp Pro
                675                 680                 685

Ala Pro Thr Val Ile Trp Gln Lys Ala Ile Thr Gln Gly Asn Lys Ala
690                 695                 700

Pro Ala Arg Pro Ala Pro Asp Ala Pro Glu Asp Thr Gly Asp Ser Asp
705                 710                 715                 720

Glu Trp Val Phe Asp Lys Lys Leu Leu Cys Glu Thr Glu Gly Arg Val
                725                 730                 735

Arg Val Glu Thr Thr Lys Asp Arg Ser Ile Phe Thr Val Glu Gly Ala
                740                 745                 750

Glu Lys Glu Asp Glu Gly Val Tyr Thr Val Thr Val Lys Asn Pro Val
                755                 760                 765

Gly Glu Asp Gln Val Asn Leu Thr Val Lys Val Ile Asp Val Pro Asp
                770                 775                 780

Ala Pro Ala Ala Pro Lys Ile Ser Asn Val Gly Glu Asp Ser Cys Thr
785                 790                 795                 800

Val Gln Trp Glu Pro Pro Ala Tyr Asp Gly Gly Gln Pro Ile Leu Gly
                805                 810                 815

Tyr Ile Leu Glu Arg Lys Lys Lys Ser Tyr Arg Trp Met Arg Leu
                820                 825                 830

Asn Phe Asp Leu Ile Gln Glu Leu Ser His Glu Ala Arg Arg Met Ile
                835                 840                 845

Glu Gly Val Val Tyr Glu Met Arg Val Tyr Ala Val Asn Ala Ile Gly
                850                 855                 860

Met Ser Arg Pro Ser Pro Ala Ser Gln Pro Phe Met Pro Ile Gly Pro
865                 870                 875                 880
```

```
Pro Ser Glu Pro Thr His Leu Ala Val Glu Asp Val Ser Asp Thr Thr
            885                 890                 895
Val Ser Leu Lys Trp Arg Pro Pro Glu Arg Val Gly Ala Gly Gly Leu
            900                 905                 910
Asp Gly Tyr Ser Val Glu Tyr Cys Pro Glu Gly Cys Ser Glu Trp Val
            915                 920                 925
Ala Ala Leu Gln Gly Leu Thr Glu His Thr Ser Ile Leu Val Lys Asp
            930                 935                 940
Leu Pro Thr Gly Ala Arg Leu Leu Phe Arg Val Arg Ala His Asn Met
945                 950                 955                 960
Ala Gly Pro Gly Ala Pro Val Thr Thr Thr Glu Pro Val Thr Val Gln
            965                 970                 975
Glu Ile Leu Gln Arg Pro Arg Leu Gln Leu Pro Arg His Leu Arg Gln
            980                 985                 990
Thr Ile Gln Lys Lys Val Gly Glu Pro Val Asn Leu Leu Ile Pro Phe
            995                 1000                1005
Gln Gly Lys Pro Arg Pro Gln Val Thr Trp Thr Lys Glu Gly Gln
    1010                1015                1020
Pro Leu Ala Gly Glu Glu Val Ser Ile Arg Asn Ser Pro Thr Asp
    1025                1030                1035
Thr Ile Leu Phe Ile Arg Ala Ala Arg Arg Val His Ser Gly Thr
    1040                1045                1050
Tyr Gln Val Thr Val Arg Ile Glu Asn Met Glu Asp Lys Ala Thr
    1055                1060                1065
Leu Val Leu Gln Val Val Asp Lys Pro Ser Pro Pro Gln Asp Leu
    1070                1075                1080
Arg Val Thr Asp Ala Trp Gly Leu Asn Val Ala Leu Glu Trp Lys
    1085                1090                1095
Pro Pro Gln Asp Val Gly Asn Thr Glu Leu Trp Gly Tyr Thr Val
    1100                1105                1110
Gln Lys Ala Asp Lys Lys Thr Met Glu Trp Phe Thr Val Leu Glu
    1115                1120                1125
His Tyr Arg Arg Thr His Cys Val Val Pro Glu Leu Ile Ile Gly
    1130                1135                1140
Asn Gly Tyr Tyr Phe Arg Val Phe Ser Gln Asn Met Val Gly Phe
    1145                1150                1155
Ser Asp Arg Ala Ala Thr Thr Lys Glu Pro Val Phe Ile Pro Arg
    1160                1165                1170
Pro Gly Ile Thr Tyr Glu Pro Pro Asn Tyr Lys Ala Leu Asp Phe
    1175                1180                1185
Ser Glu Ala Pro Ser Phe Thr Gln Pro Leu Val Asn Arg Ser Val
    1190                1195                1200
Ile Ala Gly Tyr Thr Ala Met Leu Cys Cys Ala Val Arg Gly Ser
    1205                1210                1215
Pro Lys Pro Lys Ile Ser Trp Phe Lys Asn Gly Leu Asp Leu Gly
    1220                1225                1230
Glu Asp Ala Arg Phe Arg Met Phe Ser Lys Gln Gly Val Leu Thr
    1235                1240                1245
Leu Glu Ile Arg Lys Pro Cys Pro Phe Asp Gly Gly Ile Tyr Val
    1250                1255                1260
Cys Arg Ala Thr Asn Leu Gln Gly Glu Ala Arg Cys Glu Cys Arg
    1265                1270                1275
```

-continued

```
Leu Glu  Val Arg Val Pro Gln
    1280                1285

<210> SEQ ID NO 33
<211> LENGTH: 22
<212> TYPE: DNA
<213> ORGANISM: artificial
<220> FEATURE:
<223> OTHER INFORMATION: Forward primer for exogenous MYBPC3 (in myc
      sequence)

<400> SEQUENCE: 33
gcaaaagctt attagcgagg aa                                              22

<210> SEQ ID NO 34
<211> LENGTH: 19
<212> TYPE: DNA
<213> ORGANISM: artificial
<220> FEATURE:
<223> OTHER INFORMATION: Reverse primer for exogenous MYBPC3 (in exon 2)

<400> SEQUENCE: 34
caggccgtac ttgttgctg                                                  19

<210> SEQ ID NO 35
<211> LENGTH: 20
<212> TYPE: DNA
<213> ORGANISM: artificial
<220> FEATURE:
<223> OTHER INFORMATION: Forward primer for total MYBPC3 (in exon 1)

<400> SEQUENCE: 35
ggggaagaag ccagtctcag                                                 20
```